(12) United States Patent
Kalafut et al.

(10) Patent No.: US 9,302,044 B2
(45) Date of Patent: Apr. 5, 2016

(54) PATIENT-BASED PARAMETER GENERATION SYSTEMS FOR MEDICAL INJECTION PROCEDURES

(75) Inventors: John Kalafut, Pittsburgh, PA (US); Larry McCutchan, Allison Park, PA (US); Erin Cosgrove, Hampton Falls, NH (US)

(73) Assignee: Bayer HealthCare LLC, Whippany, NJ (US)

( * ) Notice: Subject to any disclaimer, the term of this patent is extended or adjusted under 35 U.S.C. 154(b) by 1097 days.

(21) Appl. No.: 12/519,213

(22) PCT Filed: Dec. 21, 2007

(86) PCT No.: PCT/US2007/026194
§ 371 (c)(1),
(2), (4) Date: Jun. 15, 2009

(87) PCT Pub. No.: WO2008/085421
PCT Pub. Date: Jul. 17, 2008

(65) Prior Publication Data
US 2010/0113887 A1    May 6, 2010

Related U.S. Application Data

(60) Provisional application No. 60/877,779, filed on Dec. 29, 2006, provisional application No. 60/976,002, filed on Sep. 28, 2007.

(51) Int. Cl.
*A61B 5/00*    (2006.01)
*A61M 5/172*    (2006.01)
(Continued)

(52) U.S. Cl.
CPC ............ *A61M 5/172* (2013.01); *G06F 19/3468* (2013.01); *A61B 6/507* (2013.01); *A61M 5/007* (2013.01); *A61M 2005/14208* (2013.01)

(58) Field of Classification Search
CPC .... G06F 19/3468; A61M 5/172; A61M 5/007
USPC ........................................................ 600/431
See application file for complete search history.

(56) References Cited

U.S. PATENT DOCUMENTS 3,349,713 A    10/1967    Fassbender
3,520,295 A    7/1970    Kelly
(Continued)

FOREIGN PATENT DOCUMENTS

CA    2045070 A1    2/1992
CA    2077712 A1    12/1993
(Continued)

OTHER PUBLICATIONS

Page 27 of PCT/US2005/042891.*
(Continued)

*Primary Examiner* — Jonathan Cwern
(74) *Attorney, Agent, or Firm* — James R. Stevenson; Henry E. Bartony, Jr.; Gregory L. Bradley

(57) ABSTRACT

A system includes a parameter generation system to determine parameters of at least one phase of an injection procedure based at least in part upon a type of the injection procedure. The parameter generator system determines the amount of a pharmaceutical that is to be delivered to a patient at least in part on the basis of the concentration of an agent in the pharmaceutical and at least on part on the basis of a function that depends upon and varies with a patient parameter. The patient parameter can, for example, be weight, body mass index, body surface area or cardiac output. The pharmaceutical can, for example, include a contrast enhancing agent for use in an imaging procedure.

19 Claims, 55 Drawing Sheets

| Weight [kg] | Loading Coeff [g/kg] | 370 contrast Load Vol | 320 contrast Load Vol | 300 contrast Load Vol | Dual Flow Contrast Load Vol |
|---|---|---|---|---|---|
| 40 | 0.45 | 49 | 56 | 60 | 8 |
| 50 | 0.4 | 54 | 63 | 67 | 10 |
| 67 | 0.375 | 68 | 79 | 84 | 13 |
| 85 | 0.367 | 84 | 97 | 104 | 17 |
| 102 | 0.35 | 96 | 112 | 111 | 20 |
| 118 | 0.31 | 99 | 114 | 122 | 24 |
| 125 | 0.3 | 101 | 117 | 125 | 25 |

(51) Int. Cl.
  *G06F 19/00* (2011.01)
  *A61M 5/00* (2006.01)
  *A61M 5/142* (2006.01)
  *A61B 6/00* (2006.01)

(56) References Cited

U.S. PATENT DOCUMENTS

| | | |
|---|---|---|
| 3,523,523 A | 8/1970 | Heinrich et al. |
| 3,623,474 A | 11/1971 | Heilman et al. |
| 3,701,345 A | 10/1972 | Heilman et al. |
| 3,755,655 A | 8/1973 | Senecal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Bredesen et al. |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | LeFevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,207,871 A | 6/1980 | Jenkins |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers De Beyl et al. |
| 4,552,130 A | 11/1985 | Kinoshita |
| 4,559,036 A | 12/1985 | Wunsch |
| 4,563,175 A | 1/1986 | LaFond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | DiGianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | DiGianfilippo et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |

(56) References Cited

U.S. PATENT DOCUMENTS

| | | |
|---|---|---|
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | MacVicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,174 A | 1/1994 | Plotkin et al. |
| 5,276,614 A | 1/1994 | Heuscher |
| 5,286,252 A | 2/1994 | Tuttle et al. |
| 5,287,273 A | 2/1994 | Kupfer et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,417,219 A | 5/1995 | Takamizawa et al. |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kampfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | DeVale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,881,124 A | 3/1999 | Giger et al. |
| 5,882,343 A | 3/1999 | Wilson et al. |
| 5,885,216 A | 3/1999 | Evans, III et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,344,030 B1 | 2/2002 | Duchon et al. |
| 6,381,486 B1 | 4/2002 | Mistretta et al. |
| 6,385,483 B1 | 5/2002 | Uber, III et al. |
| 6,387,098 B1 | 5/2002 | Cole et al. |
| 6,397,093 B1 | 5/2002 | Aldrich |

(56) References Cited

U.S. PATENT DOCUMENTS

| | | |
|---|---|---|
| 6,397,097 B1 | 5/2002 | Requardt |
| 6,397,098 B1 | 5/2002 | Uber, III et al. |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell Gisper Sauch et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans, III et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,866,654 B2 | 3/2005 | Callan et al. |
| 6,876,720 B2 | 4/2005 | Tsuyuki |
| 6,879,853 B2 | 4/2005 | Meaney et al. |
| 6,887,214 B1 | 5/2005 | Levin et al. |
| 6,889,074 B2 | 5/2005 | Uber, III et al. |
| 6,901,283 B2 | 5/2005 | Evans, III et al. |
| 6,970,735 B2 | 11/2005 | Uber, III et al. |
| 7,094,216 B2 | 8/2006 | Trombley, III et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,313,431 B2 | 12/2007 | Uber, III et al. |
| 7,326,186 B2 | 2/2008 | Trombley, III et al. |
| 7,713,239 B2 | 5/2010 | Uber, III et al. |
| 7,925,330 B2 * | 4/2011 | Kalafut et al. ............... 600/431 |
| 7,996,381 B2 | 8/2011 | Uber, III et al. |
| 8,346,342 B2 | 1/2013 | Kalafut |
| 8,486,017 B2 * | 7/2013 | Masuda et al. ............... 604/131 |
| 2001/0027265 A1 | 10/2001 | Prince |
| 2001/0056233 A1 | 12/2001 | Uber, III et al. |
| 2002/0010551 A1 | 1/2002 | Wang et al. |
| 2002/0026148 A1 | 2/2002 | Uber, III |
| 2002/0091349 A1 | 7/2002 | Reich |
| 2002/0099254 A1 | 7/2002 | Movahed |
| 2002/0123702 A1 | 9/2002 | Cho |
| 2002/0151854 A1 | 10/2002 | Duchon et al. |
| 2002/0165445 A1 | 11/2002 | Uber et al. |
| 2003/0015078 A1 | 1/2003 | Taylor |
| 2003/0036694 A1 | 2/2003 | Liu |
| 2003/0050556 A1 | 3/2003 | Uber et al. |
| 2003/0120171 A1 | 6/2003 | Diamantopoulos et al. |
| 2003/0135111 A1 | 7/2003 | Meaney et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2004/0008028 A1 | 1/2004 | Horger et al. |
| 2004/0010229 A1 | 1/2004 | Houde et al. |
| 2004/0011740 A1 | 1/2004 | Bernard et al. |
| 2004/0015078 A1 | 1/2004 | Evans, III et al. |
| 2004/0025452 A1 | 2/2004 | McLean |
| 2004/0044302 A1 | 3/2004 | Bernard et al. |
| 2004/0064040 A1 | 4/2004 | Masuda et al. |
| 2004/0064041 A1 | 4/2004 | Lazzaro et al. |
| 2004/0097806 A1 | 5/2004 | Hunter et al. |
| 2004/0097875 A1 | 5/2004 | Bae |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2005/0004517 A1 | 1/2005 | Courtney et al. |
| 2005/0053551 A1 | 3/2005 | Badiola |
| 2005/0112178 A1 | 5/2005 | Stern |
| 2005/0256441 A1 | 11/2005 | Lotan et al. |
| 2006/0013772 A1 | 1/2006 | LeWinter et al. |
| 2006/0052764 A1 | 3/2006 | Gelfand et al. |
| 2006/0074294 A1 | 4/2006 | Williams et al. |
| 2006/0079843 A1 | 4/2006 | Brooks et al. |
| 2006/0096388 A1 | 5/2006 | Gysling et al. |
| 2006/0184099 A1 | 8/2006 | Hong |
| 2006/0211989 A1 | 9/2006 | Rhinehart et al. |
| 2006/0235353 A1 | 10/2006 | Gelfand et al. |
| 2006/0235474 A1 | 10/2006 | Demarais |
| 2006/0239918 A1 | 10/2006 | Klotz et al. |
| 2006/0253064 A1 | 11/2006 | Gelfand et al. |
| 2006/0253353 A1 | 11/2006 | Weisberger |
| 2006/0270971 A1 | 11/2006 | Gelfand et al. |
| 2006/0271111 A1 | 11/2006 | Demarais et al. |

FOREIGN PATENT DOCUMENTS

| | | |
|---|---|---|
| CN | 1343107 | 4/2002 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0439711 | 5/1995 |
| EP | 0650739 A1 | 5/1995 |
| EP | 0702966 A2 | 3/1996 |
| EP | 1262206 A2 | 12/2002 |
| FR | 2493708 A1 | 5/1982 |
| FR | 2561949 A1 | 10/1985 |
| GB | 201800 A | 8/1923 |
| GB | 2207749 A | 2/1989 |
| GB | 2252656 A | 8/1992 |
| GB | 2328745 A | 3/1999 |
| JP | 50017781 A | 2/1975 |
| JP | 58015842 A | 1/1983 |
| JP | 59214432 A | 12/1984 |
| JP | 60194934 A | 10/1985 |
| JP | 60194935 A | 10/1985 |
| JP | 60253197 A | 12/1985 |
| JP | 62216199 A | 9/1987 |
| JP | 63040538 A | 2/1988 |
| JP | 63290547 A | 11/1988 |
| JP | 1207038 A | 8/1989 |
| JP | 2224647 A | 9/1990 |
| JP | 2234747 A | 9/1990 |
| JP | 3055040 A | 3/1991 |
| JP | 4115677 A | 4/1992 |
| JP | 5084296 A | 4/1993 |
| JP | 7178169 A | 7/1995 |
| JP | 10211198 A | 8/1998 |
| JP | 2002-507438 | 3/2002 |
| JP | 2003-102724 A | 4/2003 |
| JP | 2003-116843 | 4/2003 |
| JP | 2003-210456 | 7/2003 |
| JP | 2003-225234 | 8/2003 |
| JP | 2004-519304 | 7/2004 |

(56) References Cited

FOREIGN PATENT DOCUMENTS

| | | |
|---|---|---|
| JP | 2004298550 | 10/2004 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 0064353 A2 | 11/2000 |
| WO | 03015633 A1 | 2/2003 |
| WO | 2004012787 A2 | 2/2004 |
| WO | 2005004038 A1 | 1/2005 |
| WO | 2005016165 A1 | 2/2005 |
| WO | 2006042093 A1 | 4/2006 |
| WO | 2006055813 A2 | 5/2006 |
| WO | WO 2006058280 A2 * | 6/2006 |
| WO | 2008011401 A2 | 1/2008 |
| WO | 2008082937 A2 | 7/2008 |
| WO | 2008085421 A2 | 7/2008 |
| WO | 2009012023 A1 | 1/2009 |

OTHER PUBLICATIONS

Sablayrolles, J-L, "Cardiac CT: Experience from Daily Practice", Advance CT, A GE Healthcare Publication. Aug. 2004.
"Digital Injector for Angiography", Sias. (Sep. 7, 1993).
International Search Report and Written Opinion for counterpart PCT Application No. PCT/US2005/41913.
Fleischmann, Dominik, "Present and Future Trends in Multiple Detector-Row CT Applications; CT Angiography", Eur. Radiol. 12 (Suppl. 2) 2002.
Korosec, Frank, "Basic Principles of Phase-contrast, Time-of-flight, and Contrast-enhanced MR Angiography", 1999.
Baker, Aaron; et al. "Fluid Mechanics Analysis of a Spring-Loaded Jet Injector." IEEE Transactions on Biomedical Engineering, vol. 46, No. 2, Feb. 1999.
Cademartiri, F. and Luccichenti, G., et al. (2004) "Sixteen-Row Multislice Computed Tomography:Basic Concepts, Protocols, and Enhanced Clinical Application," Semin Ultrasound CT MR 25(1):2-16.
K.T. Bae, J.P. Heiken, and J.A. Brink, "Aortic and Hepatic Contrast Medium Enhancement at CT. Part I. Prediction and a Computer Model," Radiology, vol. 207, pp. 647-655, 1998.
K.T. T Bae, "Peak Contrast Enhancement in CT and MR Angiography: When Does It Occur and Why? Pharmacokinetic Study in a Porcine Model," Radiology, vol. 227, pp. 809-816, 2003.
K.T. Bae et al., "Multiphasic Injection Method for Uniform Prolonged Vascular Enhancement at CT Angiography: Pharmacokinetic Analysis and Experimental Porcine Method," Radiology, vol. 216, pp. 872-880, 2000.
D. Fleischmann and K. Hittmair, "Mathematical Analysis of Arterial Enhancement and Optimization of Bolus Geometry for CT Angiography Using the Discrete Fourier Transform," J Comput Assist Tomogr, vol. 23, pp. 474-484, 1999.
Fisher and Teo, "Optimal Insulin Infusion Resulting from a Mathematical Model of Blood Glucose Dyanamics", IEEE Trans Biomed Eng, vol. 36(4), pp. 479-486, 1989.
Jacobs, "Algorithm for Optimal Linear Model-Based Control with Application to Pharmacokinetic Model-Driven Drug Delivery", IEEE Trans Biomed Eng, vol. 37(1), pp. 107-109, 1990.
Wada and Ward, "The Hybrid Model: A New Pharmacokinetic Model for Computer-Controlled Infusion Pumps", IEEE Trans. Biomed. Eng, vol. 41(2), pp. 134-142, 1994.
Wada and Ward, "Open Loop Control of Multiple Drug Effects in Anesthesia", IEEE Trans. Biomed Eng, vol. 42(7), pp. 666-677, 1995.
Neatpisarnvanit and Boston, "Estimation of Plasma Insulin from Plasma Glucose", IEEE Trans Biomed Eng, vol. 49 (11), pp. 1253-1259, 2002.
Gentilini et al., "A New Paradigm for the Closed-Loop Intraoperative Administration of Analgesics in Humans", IEEE Tran Biomed Eng, vol. 49(4), pp. 289-2999, 2002.
Mahnken, A.H., Henzler, D, et al., "Determination of Cardiac Output with Multislice Spiral Computed Tomography: A Validation Study", Invest Radiol 39(8): 451-4, 2004.
Mahnken, A.H., Klotz, E., et al., "Measurement of Cardiac Output from a Test-Bolus Injection in Multislice Computed Tomography", Eur Radiol 13(11): 2498-504, 2003.
Garrett, J.S., Lanzer, P., et al., "Measurement of Cardiac Output by Cine Computed Tomography", Am J Cardiol 56 (10): 657-61, 1985.
Liebel-Flarsheim Company, Angiomat 6000 Digital Injection System Operator's Manual, 600950 Rev 1; (1990); pp. 1-1 to 9-6.
Guytan, Arthur. C., Circulatory Physiology: Cardiac Output and Its Regulation, Saunders, Philadelphia, (1973); p. 173.
"Infus O.R. Multi-Drug Syringe Pump with Smart Labels", Bard MedSystems Division Inc.; (2005); pp. 2693-2696.
Non-Final office Action mailed Mar. 12, 2013, in U.S. Appl. No. 13/655,525, John F. Kalafut et al., filed Oct. 19, 2012.
Non-Final Office Action mailed Feb. 15, 2012, in U.S. Appl. No. 12/519,040, John F. Kalafut, filed Jun. 12, 2009.
Flegal, K.M., et al., "Prevalence and trends in obesity among US adults," JAMA, 2002, vol. 288, Issue 14, pp. 1-4, 1999-2000.
Fleischmann, D., "Contrast Medium Injection Technique," In: U. Joseph Schoepf: "Multidetector—Row CT of the Thorax," pp. 47-59, Jan. 22, 2004.
Gardiner, G. A., et al., "Selective Coronary Angiography Using a Power Injector," AJR Am J Roentgenol., vol. 146, Issue 4, pp. 831-833, Apr. 1986.
Gembicki, F.W., "Vector Optimization for Control with Performance and Parameter Sensitivity Indices," PhD Thesis, Case Western Reserve University, 1974.
Gerlowski L.E. and Jain R.K., "Physiologically Based Pharmacokinetic Modeling: Principles and Applications," Journal of Pharmaceutical Sciences, vol. 72, pp. 1104-1125, Oct. 1983.
Goldfarb, S., "Contrast-induced nephropathy: Risk factors, pathophysiology, and prevention," Applied Radiology (online supplement), pp. 5-16, Aug. 2005.
Goss, J. E., et al., "Power injection of contrast media during percutaneous transluminal coronary artery angioplasty," Catheterization and Cardiovascular Diagnosis, vol. 16, pp. 195-198 1989.
Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109, Feb. 1992.
Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.
Hansen, P.C, Regularization tools: a MATLAB package for analysis and solution of discrete ill-posed problems, Numerical Algorithms, vol. 6, Issue 1, pp. 35, 1994.
Hansen, P.C., "The truncated SVD as a method for regularization," BIT Numerical Mathematics, vol. 27, Issue 4, pp. 534-555, 1987.
Non-Final Office Action mailed Dec. 17, 2008, in U.S. Appl. No. 11/691,823, John F. Kalafut et al., filed Mar. 27, 2007.
Harris P., H. D. "The Human Pulmonary Circulation," Edinburgh, Churchill Livingstone, (Appendix I), 1986.
Hayes, M.H., "Statistical Digital Signal Processing and Modeling," New York, New York: Wiley and Sons, pp. 154-177, 1996.
Heiken, J.P. et al., "Dynamic Contrast-Enhanced CT of the Liver: Comparison of Contrast Medium Injection Rates and Uniphasic and Biphasic Injection Protocols," Radiology, vol. 187, No. 2, May 1993, pp. 327-331.
International Preliminary Report on Patentability and International Search Report for International Patent Application No. PCT/US00/10842 issued May 22, 2001.
International Preliminary Report on Patentability and Written Opinion for International Patent Application No. PCT/US2007/026194 issued Jun. 30, 2009.

(56) References Cited

OTHER PUBLICATIONS

International Preliminary Report on Patentability and Written Opinion for International Patent Application No. PCT/US2007/087765 issued Jun. 30, 2009.
International Preliminary Report on Patentability and Written Opinion for International Patent Application No. PCT/US2008/067982 issued Jan. 19, 2010.
International Preliminary Report on Patentability and Written Opinion for International Patent Application No. PCT/US2009/047168 issued Jan. 5, 2011.
International Preliminary Report on Patentability and Written Opinion for International Patent Application No. PCT/US2011/041802 issued Dec. 28, 2012.
International Preliminary Report on Patentability and Wrtitten Opinion for International Patent Application No. PCT/US2005/042891 issued May 30, 2007.
International Preliminary Report on Patentability for International Application No. PCT/EP2005/007791, International Bureau of WIPO, Geneva, Switzerland, issued on May 22, 2007.
International Preliminary Report on Patentability for International Patent Application No. PCT/US2005/041913 issued May 22, 2007.
Krause, W., "Application of pharmacokinetics to computed tomography: injection rates and schemes: mono-, bi-, or multiphasic?," Investigative Radiology, vol. 31, Issue 2, pp. 91-100, Feb. 1996.
International Search Report for International Patent Application No. PCT/US00/10842 mailed Apr. 5, 2001.
International Search Report for International Patent Application No. PCT/US2007/026194 mailed Jun. 26, 2008.
International Search Report for International Patent Application No. PCT/US2007/087765 mailed Jun. 12, 2008.
International Search Report for International Patent Application No. PCT/US2008/067982 mailed Oct. 8, 2008.
International Search Report for International Patent Application No. PCT/US2009/047168 mailed Aug. 4, 2009.
International Search Report for International Patent Application No. PCT/US2011/041802 mailed Jan. 5, 2012.
International Search Report for International Patent Application No. PCT/US96/15680 mailed Jan. 28, 1997.
Ireland, M.A., et al., "Safety and Convenience of a Mechanical Injector Pump for Coronary Angiography," Catheterization and Cardiovascular Diagnosis, vol. 16, Issue 3, pp. 199-201, 1989.
iSTAT 1 System Manual, Abbott Laboratories, Rev. Aug. 14, 2006.
Non-Final Office Action mailed Apr. 26, 2013, in U.S Appl. No. 12/519,040, John F. Kalafut, filed Jun. 12, 2009.
Jo, S.H., et al. "Renal Toxicity Evaluation and Comparison Between Visipaque (Iodixanol) and Hexabrix (Ioxaglate) in Patients With Renal Insufficiency Undergoing Coronary Angiography," Journal of the American College of Cardiology, vol. 48, Issue 5, pp. 924-930, 2006.
MCT and MCT Plus Injection Systems Operation Manual KMP 810P, MEDRAD, Inc. 1991.
Koh, T.S., et al., "Assessment of Perfusion by Dynamic Contrast-Enhanced Imaging Using a Deconvolution Approach Based on Regression and Singular Value Decomposition," IEEE Transactions on Medical Imaging, vol. 23, Issue 12, pp. 1532-1542, Dec. 2004.
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Parker, K.J. and Tuthill T.A., "A Particulate Contrast Agent With Potential for Ultrasound Imaging of Liver," Ultrasound in Medicine & Biology vol. 13, Issue 9, pp. 555-566, Sep. 1987.
European Search Report mailed Feb. 21, 2012 in European Patent Application No. 11001045.1.
European Search Report mailed Jan. 30, 2003 in European Patent Application No. 02020247.9.
European Search Report mailed Jun. 17, 1996 in European Patent Application No. 95202547.6.
PHYSBE a classic model of the human circulatory system available from The Math Works, Inc. of Natick, Massachusetts, accessed at www.mathworks.com/products/demos/simulink/physbe, May 31, 2005, pp. 11.
Mark V/Mark V Plus Injector Operation Manual KMP 805P Rev. B. MEDRAD, Inc, 1990.
Krieger, R. A., C02-Power-Assisted Hand-Held Syringe: Better Visualization during Diagnostic and Interventional, vol. 19, Issue 2, pp. 123-128, Feb. 1990.
McCullough. P.A. et al., "Contrast-Induced Nephropathy (ON) Consensus Working Panel: Executive Summary," Reviews in Cardiovascular Medicine, vol. 7, Issue 4, pp. 177-197, 2006.
McClellan, J.H., "Parametric Signal Modeling," Chapter 1 in Advanced Topics in Signal Processing, Pentice-Hall, Englewood Cliffs, NJ, 1988.
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
Sung, C.K., et al. "Urine Attenuation Ratio: A Mew CT Indicator of Renal Artery Stenosis," AJR Am J Roentgenol, vol. 187, pp. 532-540, Aug. 2006.
Supplementary European Search Report mailed Apr. 15, 2011 in European Patent Application No. 07867951.1.
Final Office Action mailed Jun. 19, 2013, in U.S. Appl. No. 13/186,983, John F. Kalafut et al., filed Jul. 20, 2011.
Supplementary European Search Report mailed Aug. 19, 2010 in European Patent Application No. 05852259.0.
Final Office Action mailed May 10, 2013, in U.S. Appl. No. 12/611,172, John F. Kalafut et al., filed Nov. 3, 2009.
Supplementary European Search Report mailed Dec. 9, 1998 in European Patent Application No. EP 96936079.0.
Final Office Action mailed Oct. 1, 2009, in U.S. Appl. No. 11/691,823, John F. Kalafut et al., filed Mar. 27, 2007.
Final Office Action mailed Oct. 2, 2012, in U.S. Appl. No. 12/519,040, John F. Kalafut, filed Jun. 12, 2009.
Supplementary European Search Report mailed Jul. 23, 2013 in European Patent Application No. 08771789.8.
Tyco's Complaint and Jury Demand, Civil Case No. 06-763, U.S.D.C. (S.D.Ohio), *Tyco Healthcare Group LP, Mallinckrodt Inc. and Liebel-Flarsheim Company v. Medrad, Inc.*
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
European Search Report and Opinion mailed on Nov. 21, 2013 from EP No. 13004902.6.
Office Action mailed Jan. 3, 2014 in U.S. Appl. No. 11/691,823.
Search Report and Supplementary European Search Report for EP05849688 dated Mar. 21, 2014.
US 5,840,021, 12/1997, (withdrawn).
"Disposable Low-Cost Catheter Tip Sensor Measures Blood Pressure during Surgery," Sensor, Jul. 1989.
"The Solution for Your IV Formulas," Valley Lab. Inc., E-39-15, 3399, 3400, 2646.
Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.
Angiography, Catheterization and Cardiovascular Diagnosis, vol. 19, pp. 123-128, 1990.
Awai, K., et al., "Aortic and hepatic enhancement and tumor-to-liver contrast: analysis of the effect of different concentrations of contrast material at multi-detector row helical CT.," Radiology, vol. 224, Issue 3, pp. 757-763, 2002.
Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.
Bae, K.T., et al., "Uniform vascular contrast enhancement and reduced contrast medium volume achieved by using exponentially decelerated contrast material injection method," Radiology, vol. 231, Issue 3, pp. 732-736, 2004.
Becker, C.R., et al., "Optimal contrast application for cardiac 4-detector-row computed tomography," Investigative Radiology, vol. 38, Issue 11, pp. 690-694, Nov. 2003.

(56) References Cited

OTHER PUBLICATIONS

Blomley, M.J.K. and Dawson, P., "Bolus Dynamics: Theoretical and Experimental Aspects," The Brit. J. of Radiology, 70, pp. 351-359, 1997.

Buckley, D.L., et al., "Measurement of single kidney function using dynamic contrast-enhanced MRI: comparison of two models in human subjects," Journal of Magnetic Resonance Imaging, vol. 24, Issue 5, pp. 117-123, Nov. 2006.

Cademartiri, F., et al., "Intravenous contrasts material administration at 16-detector row helical CT coronary angiography: test bolus versus bolus-tracking technique," Radiology, vol. 233, Issue 3, pp. 817-823, Dec. 2004.

Non-Final Office Action mailed Nov. 5, 2012, in U.S. Appl. No. 13/186,983, John F. kalafut et al., filed Jul. 20, 2011.

Non-Final Office Action mailed Sep. 17, 2012, in U.S. Appl. No. 12/611,172, John F. Kalafut et al., filed Nov. 3, 2009.

Dardik, H. et al., "Remote Hydraulic Syringe Actuator," Arch. Surg., vol. 115, Issue 1, Jan. 1980.

Dawson, P. and M. Blomley, "The value of mathematical modelling in understanding contrast enhancement in CT with particular reference to the detection of hypovascular liver metastases," European Journal of Radiology, vol. 41, Issue 3, pp. 222-236, Mar. 2002.

Østergaard, L., et al., "High resolution measurement of cerebral blood flow using intravascular tracer bolus passages. Part 1: Mathematical approach and statistical analysis," Magnetic Resonance in Medicine, vol. 36, Issue 5, pp. 715-725, 1996.

Østergaard, L., et al., "High resolution measurement of cerebral blood flow using intravascular tracer bolus passages. Part II: Experimental comparison and preliminary results," Magn Reson Med, vol. 36, Issue 5, pp. 726-736, 1996.

Gerlowski, L., et al., "Physiologically Based Pharmacokinetic Modeling: Principles and Application", Journal of Pharmaceutical Sciences, vol. 72, Issue 10, pp. 1103-1127, Oct. 31, 1983.

Non-Final Office Action mailed Jul. 15, 2014 in related U.S. Appl. No. 11/691,823.

Non-Final Office Action mailed Dec. 12, 2014, in U.S. Appl. No. 13/186,983.

Non-Final Office Action mailed Apr. 23, 2014, in U.S. Appl. No. 12/519,040, John F. Kalafut et al., filed Dec. 29, 2006.

The Supplementary European Search Report from dated Jul. 24, 2015 related EP Application No. EP12876629.

* cited by examiner if peak_enhancement$_{test}$ > 160 HU
ratio = 30/70
else if 120 < peak_enhancement$_{test}$ <= 160
ratio = 50/50
else if peak_enhancement$_{test}$ < 120
ratio = 70/30

| Weight [kg] | Loading Coeff [gl/kg] | 370 contrast Load Vol | 320 contrast Load Vol | 300 contrast Load Vol | Dual Flow Contrast Load Vol |
|---|---|---|---|---|---|
| 40 | 0.45 | 49 | 56 | 60 | 8 |
| 50 | 0.4 | 54 | 63 | 67 | 10 |
| 67 | 0.375 | 68 | 79 | 84 | 13 |
| 85 | 0.367 | 84 | 97 | 104 | 17 |
| 102 | 0.35 | 96 | 112 | 111 | 20 |
| 118 | 0.31 | 99 | 114 | 122 | 24 |
| 125 | 0.3 | 101 | 117 | 125 | 25 |

Fig. 24E

| Total Contrast Load Volume [+20 ml test] | | | |
|---|---|---|---|
| kg | 370 CM | 320 CM | 300 CM |
| 40 | 77 | 84 | 88 |
| 50 | 84 | 93 | 97 |
| 67 | 101 | 112 | 117 |
| 85 | 121 | 134 | 141 |
| 102 | 137 | 152 | 151 |
| 118 | 142 | 158 | 166 |
| 125 | 146 | 162 | 170 |

Fig. 24F

| Total Iodine Load [+20 ml Test] | | | |
|---|---|---|---|
| kg | 370 CM | 320 CM | 300 CM |
| 40 | 28 | 27 | 26 |
| 50 | 31 | 30 | 29 |
| 67 | 37 | 36 | 35 |
| 85 | 45 | 43 | 42 |
| 102 | 51 | 49 | 45 |
| 118 | 53 | 51 | 50 |
| 125 | 54 | 52 | 51 |

Fig. 24G

Fig. 33A
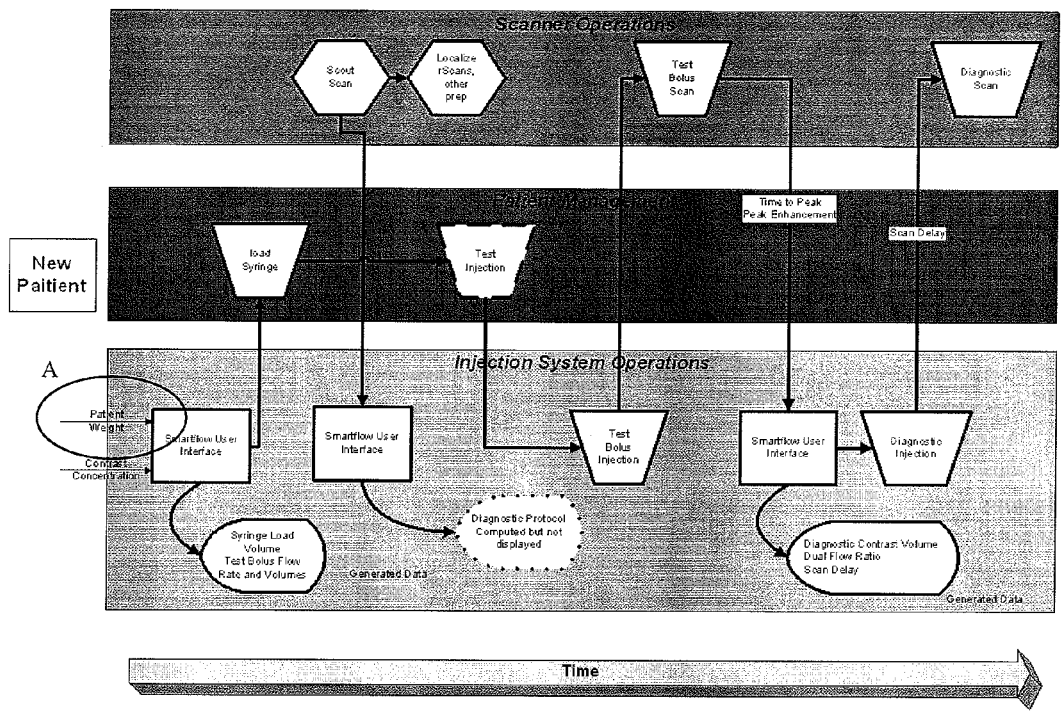
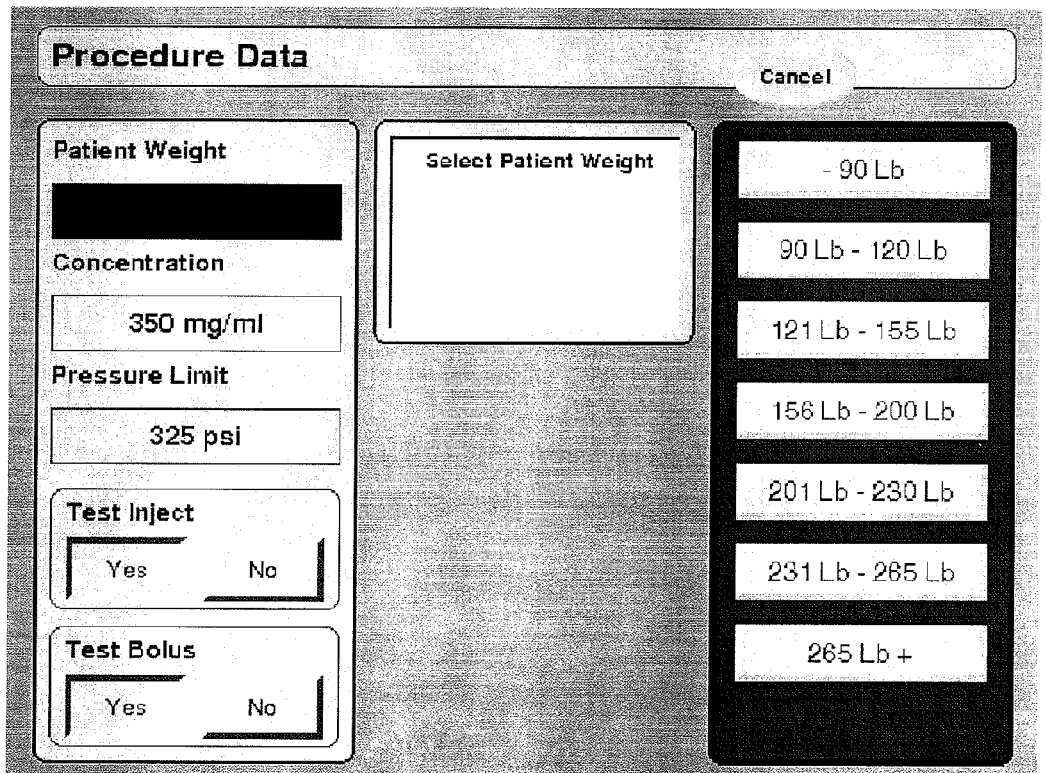

Fig. 33E
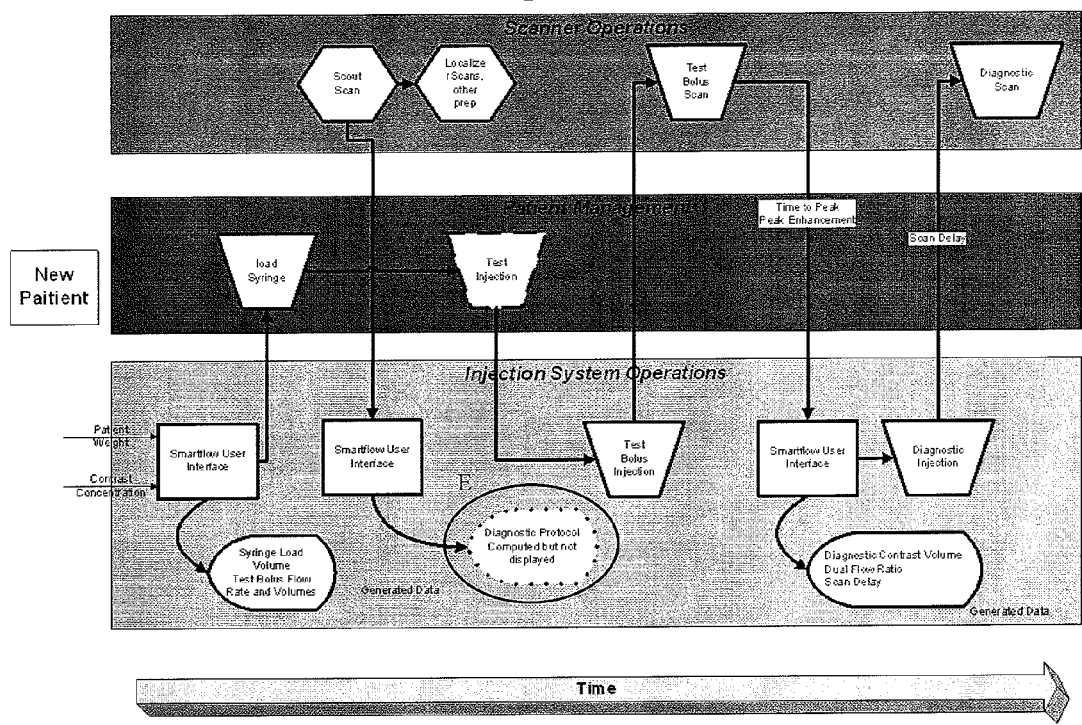
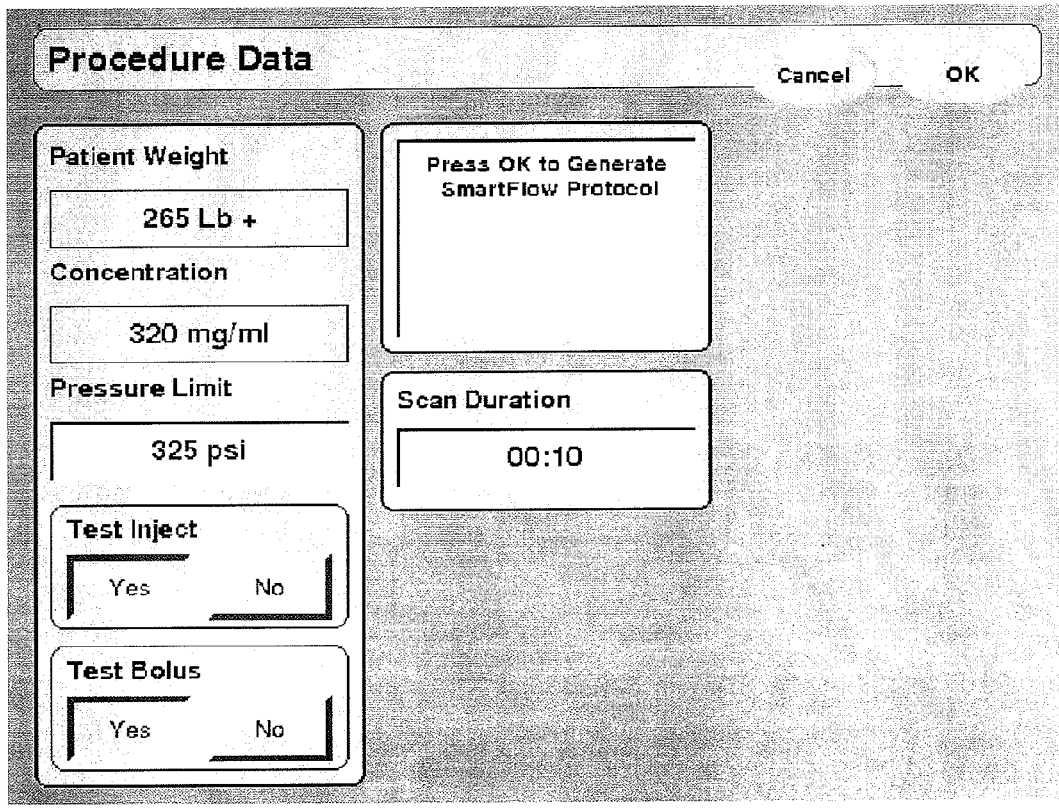

Fig. 33F
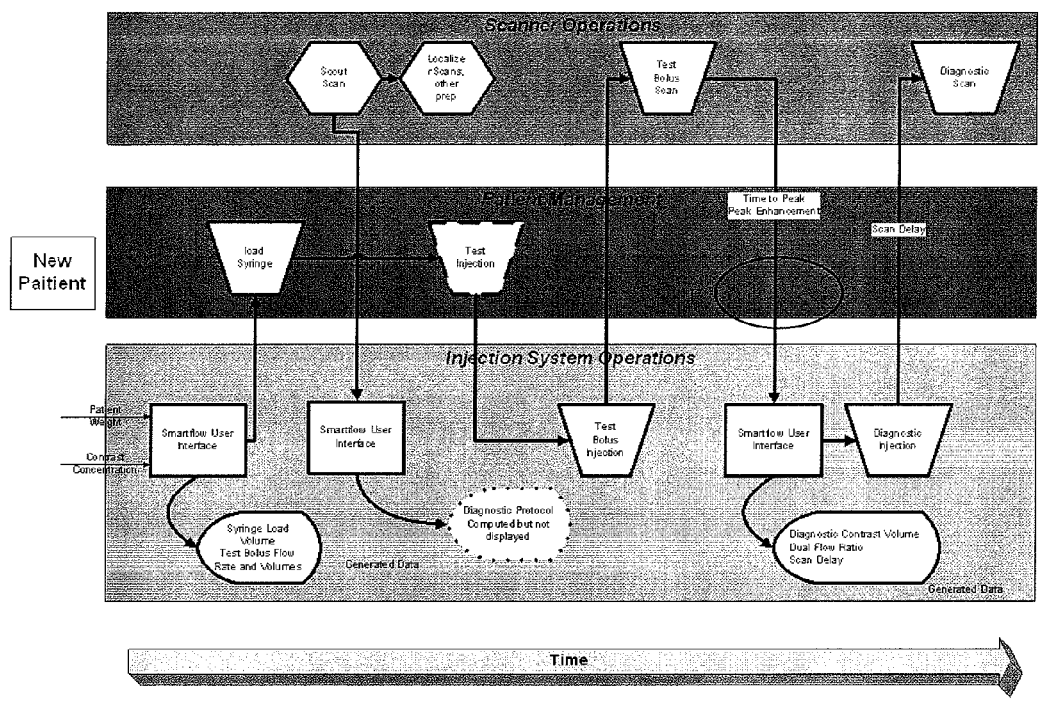
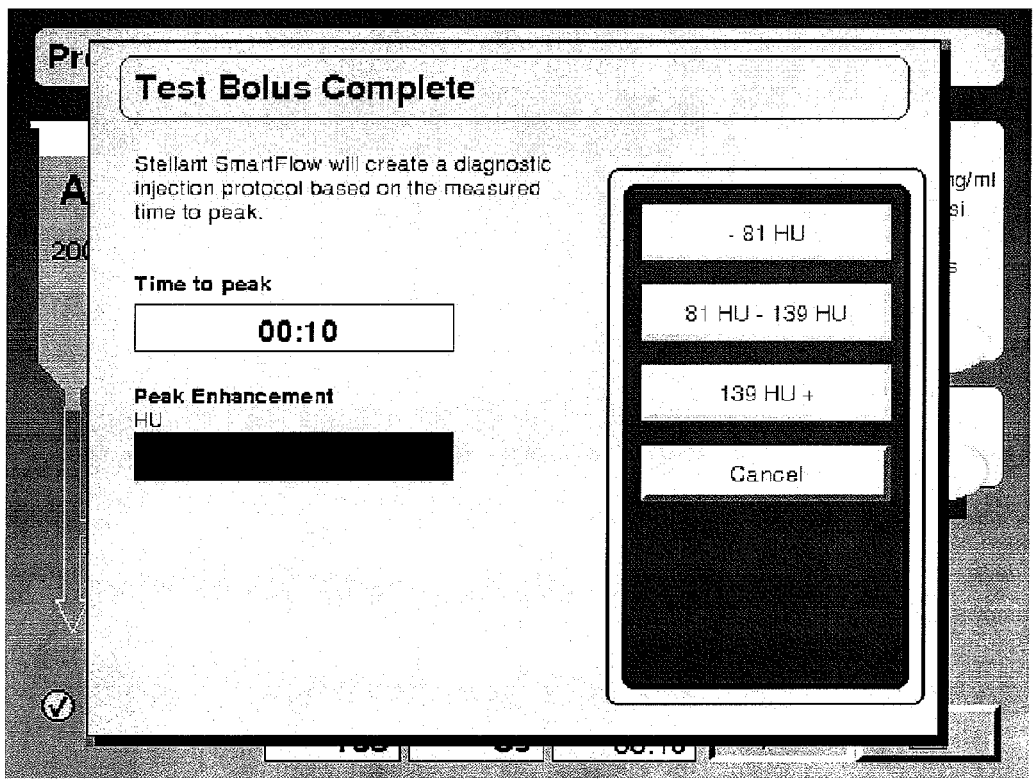

Fig. 33G
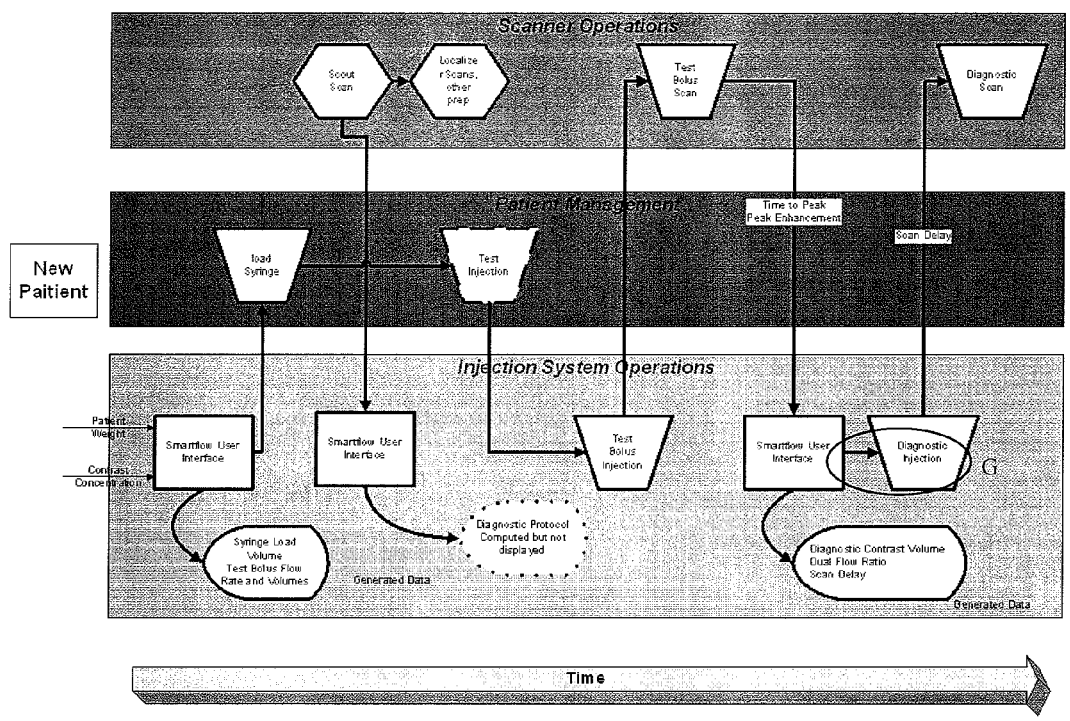
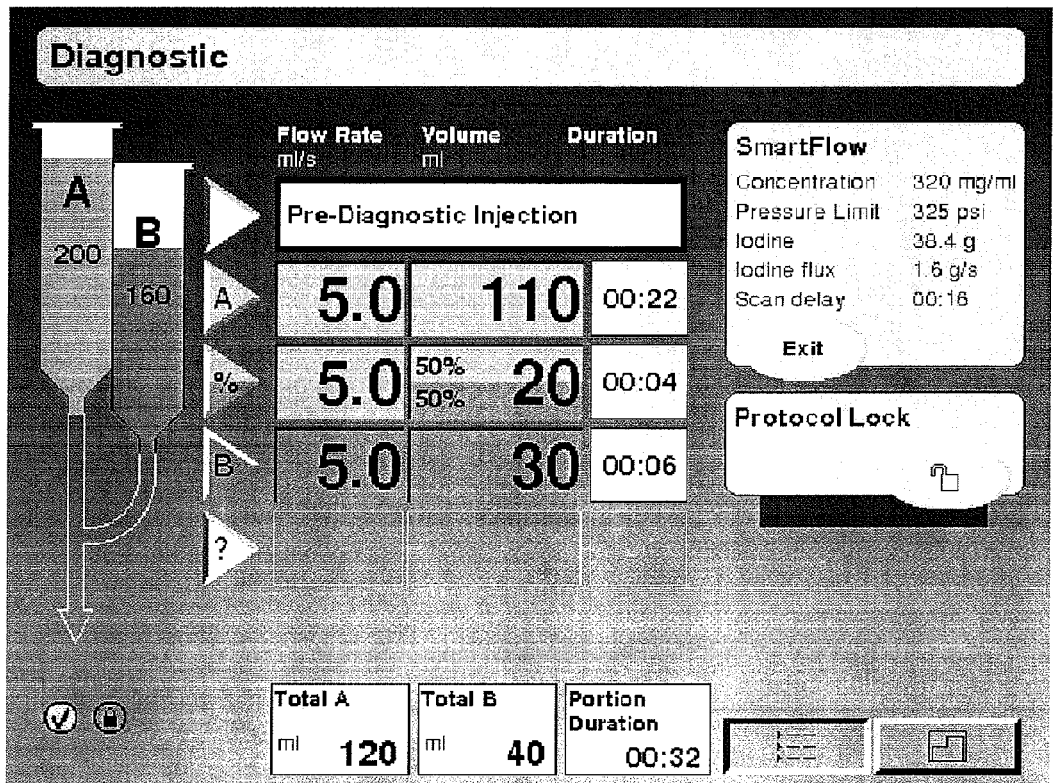

Fig. 34B

| Contrast/Saline Ratio | Peak Enhancement [HU] | Scan Delay | Scan Duration [sec] | Weight[kg] |
|---|---|---|---|---|
| 30/70 | >= 140 | Tpeak + 6 | >= 10 | >= 102 |
| 50/50 | >80 & <= 139 | Tpeak + 4 | >= 10 | <102 |
| 70/30 | <=80 | Tpeak + 6 | < 10 | (any) |

*use inj dur = scan dur + [ 4 ] sec

Contrast Concentration

Volumetric Flow Rates
Scan Durations (sec)

| ~weight range [lbs] | weight range [kg] | <=12 sec | 13 | 14 | 15 | 16 | 17 | 18 | 19 | 20 | Phase 1 Vol ml | Max Dual Flow Vol CM ml |
|---|---|---|---|---|---|---|---|---|---|---|---|---|
| <88 | <40 | 1.3 | 1.2 | 1.1 | | 1.0 | | 0.9 | | | | |
| 88-130 | 40-59 | 1.6 | 1.5 | 1.4 | 1.3 | | 1.2 | 1.1 | | | | |
| 131-163 | 60-74 | 1.7 | 1.6 | 1.5 | 1.4 | 1.3 | | 1.2 | | | | |
| 164-207 | 75-94 | 2.0 | 1.9 | 1.8 | 1.7 | 1.6 | 1.5 | 1.4 | | | | |
| 208-240 | 95-109 | 2.2 | 2.1 | 2.0 | 1.9 | 1.8 | 1.7 | 1.6 | | | | |
| 241-275 | 110-125 | 2.3 | 2.2 | 2.0 | 1.9 | 1.8 | 1.7 | 1.7 | | | | |
| >275 | >125 | 2.3 | 2.2 | 2.1 | 2.0 | 1.9 | 1.8 | 1.7 | | | | |

Iodine Administration Rates
Scan Durations

| ~weight range [lbs] | weight range [kg] | <=12 sec | 13 | 14 | 15 | 16 | 17 | 18 | 19 | 20 | Phase 1 g | Max Dual Flow g I |
|---|---|---|---|---|---|---|---|---|---|---|---|---|
| <88 | <40 | 3.4 | 3.2 | 3.0 | 2.8 | 2.7 | 2.6 | 2.5 | 2.4 | 2.7 | 54 | 8 |
| 88-130 | 40-59 | 4.2 | 4.0 | 3.8 | 3.6 | 3.4 | 3.2 | 3.1 | 2.9 | 3.4 | 68 | 10 |
| 131-163 | 60-74 | 4.5 | 4.3 | 4.0 | 3.8 | 3.6 | 3.4 | 3.3 | 3.1 | 3.6 | 72 | 13.4 |
| 164-207 | 75-94 | 5.4 | 5.1 | 4.8 | 4.5 | 4.3 | 4.1 | 3.9 | 3.7 | 4.3 | 86 | 17 |
| 208-240 | 95-109 | 6.0 | 5.7 | 5.4 | 5.1 | 4.8 | 4.6 | 4.4 | 4.2 | 4.8 | 96 | 20.4 |
| 241-275 | 110-125 | 6.2 | 5.8 | 5.5 | 5.2 | 4.9 | 4.7 | 4.5 | 4.3 | 4.9 | 99 | 23.6 |
| >275 | >125 | 6.3 | 6.0 | 5.6 | 5.3 | 5.1 | 4.8 | 4.6 | 4.4 | 5.1 | 101 | 25 |

| ~weight range [lbs] | weight range [kg] | <=12 sec | 13 | 14 | 15 | 16 | 17 | 18 | 19 | 20 | Phase 1 g | Max Dual Flow g I |
|---|---|---|---|---|---|---|---|---|---|---|---|---|
| <88 | <40 | 1.3 | 1.2 | 1.1 | 1.1 | 1.0 | 1.0 | 0.9 | 0.9 | 1.0 | 20 | 3.0 |
| 88-130 | 40-59 | 1.6 | 1.5 | 1.4 | 1.3 | 1.3 | 1.2 | 1.1 | 1.1 | 1.3 | 25 | 3.7 |
| 131-163 | 60-74 | 1.7 | 1.6 | 1.5 | 1.4 | 1.3 | 1.3 | 1.2 | 1.2 | 1.3 | 27 | 5.0 |
| 164-207 | 75-94 | 2.0 | 1.9 | 1.8 | 1.7 | 1.6 | 1.5 | 1.4 | 1.4 | 1.6 | 32 | 6.3 |
| 208-240 | 95-109 | 2.2 | 2.1 | 2.0 | 1.9 | 1.8 | 1.7 | 1.6 | 1.6 | 1.8 | 36 | 7.5 |
| 241-275 | 110-125 | 2.3 | 2.2 | 2.0 | 1.9 | 1.8 | 1.7 | 1.7 | 1.6 | 1.8 | 37 | 8.7 |
| >275 | >125 | 2.3 | 2.2 | 2.1 | 2.0 | 1.9 | 1.8 | 1.7 | 1.6 | 1.9 | 38 | 9.3 |

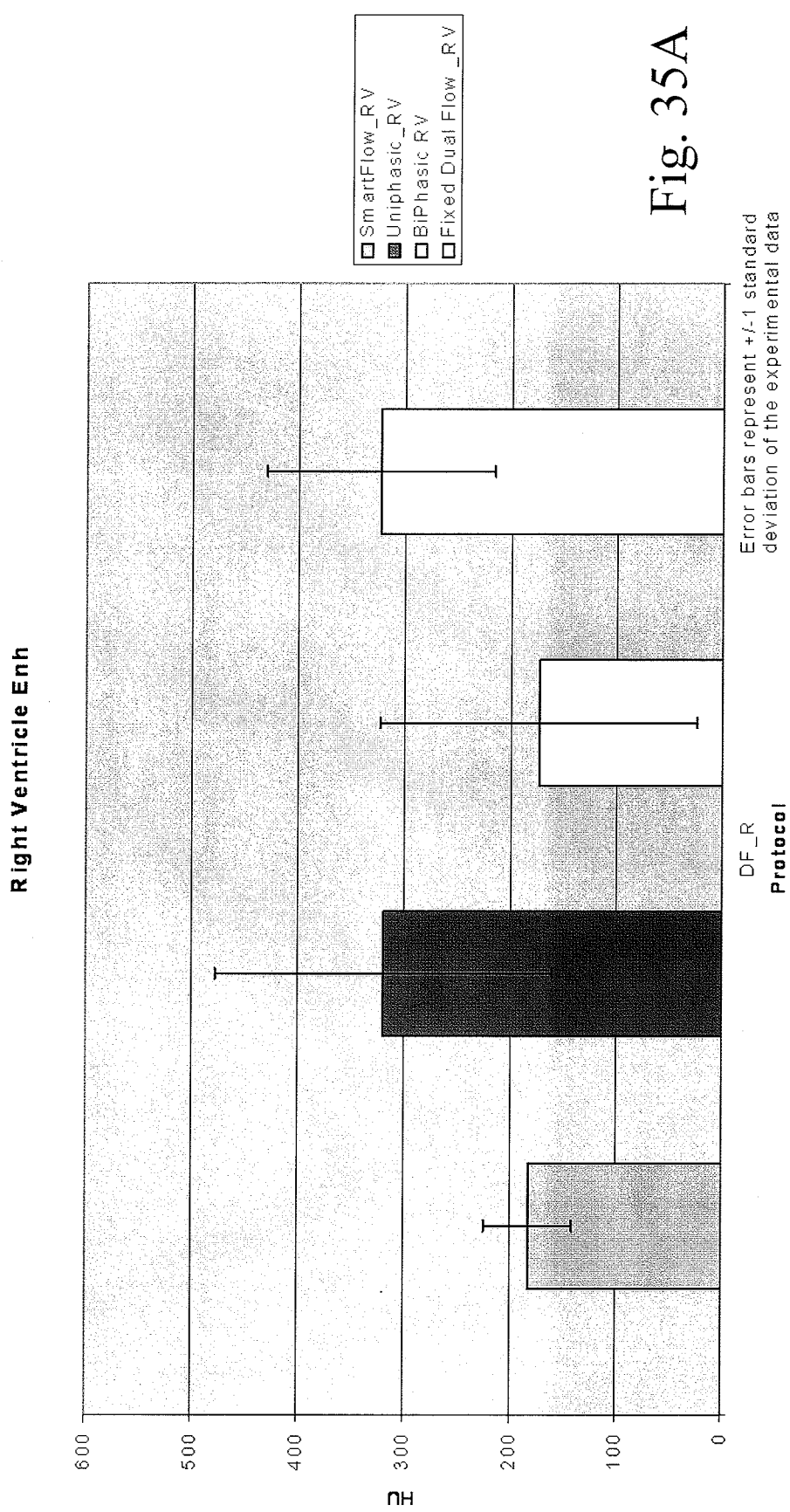

Subj 24 SmartFlow1 study. 5'10, 202 lb m (BMI 29), 133 ml (370) phase 1,5ml/s (dur1 = 26.6s) DualFlow = 50/50 80 ml. ScanDur = 26 sec. Time to peak = 24 sec = scandelay.

PATIENT-BASED PARAMETER GENERATION SYSTEMS FOR MEDICAL INJECTION PROCEDURES

CROSS-REFERENCE TO RELATED APPLICATION

This application claims benefit of PCT Application US07/026194, filed Dec. 21, 2007 and U.S. Provisional Application Ser. No. 60/877,779, filed on Dec. 29, 2006, and U.S. Provisional Patent Application Ser. No. 60/976,002, filed Sep. 28, 2007, the contents of which are hereby incorporated by reference.

RELATED APPLICATIONS

This application contains subject matter that may be related to that disclosed and/or claimed in Published PCT Application No. WO/2006/058280 (PCT International Patent Application No. PCT/US05/042891), filed on Nov. 23, 2005 and Published PCT Application No. WO/2006/055813 (PCT International Patent Application No. PCT/US2005/041913), filed on Nov. 16, 2005, the disclosures of which are incorporated herein by reference and made a part hereof.

BACKGROUND OF THE INVENTION

The present invention is related to devices, systems and methods for fluid delivery, and, particularly, to devices, systems and methods for delivery of a pharmaceutical fluid to a patient, and, especially for delivery of a contrast medium to a patient during a medical injection procedure.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosures of all references cited herein are incorporated by reference.

The administration of contrast medium (with, for example, a powered injector) for radiological exams typically starts with the clinician filling an empty, disposable syringe with a certain volume of contrast agent pharmaceutical. In other procedures, a syringe pre-filled with contrast agent is used. The clinician then determines a volumetric flow-rate and a volume of contrast to be administered to the patient to enable a diagnostic image. An injection of saline solution, having a volume and flow rate determined by the operator, often follows the administration of contrast agent into the veins or arteries. A number of currently available injectors allow for the operator to program a plurality of discrete phases of volumetric flow rates and volumes to deliver. For example, the SPECTRIS SOLARIS® and STELLANT® injectors available from Medrad, Inc. of Indianola, Pa., provide for entry of up to and including six discrete pairs or phases of volumetric flow rate and volume for delivery to a patient (for example, for contrast and/or saline). Such injectors and injector control protocols for use therewith are disclosed, for example, in U.S. Pat. No. 6,643,537 and Published U.S. Patent Application Publication No. 2004-0064041, assigned to the assignee of the present invention, the disclosures of which are incorporated herein by reference. The values or parameters within the fields for such phases are generally entered manually by the operator for each type of procedure and for each patient undergoing an injection/imaging procedure. Alternatively, earlier manually entered values of volume and flow rate can be stored and later recalled from the computer memory. However, the manner in which such parameters are to be determined for a specific procedure for a specific patient are not well developed.

In that regard, differences in contrast dosing requirements for different patients during imaging and other procedures have been recognized. For example, U.S. Pat. No. 5,840,026, assigned to the assignee of the present invention, the disclosure of which is incorporated herein by reference, discloses devices and methods to customize the injection to the patient using patient specific data derived before or during an injection. Although differences in dosing requirements for medical imaging procedures based upon patient differences have been recognized, conventional medical imaging procedures continue to use pre-set doses or standard delivery protocols for injecting contrast media during medical imaging procedures. Given the increased scan speed of recently available CT scanners including MDCT (or MSCT) scanners, single phase injections are dominant over biphasic or other multiphasic injections in regions of the world where such fast scanners are used. Although using standard, fixed or predetermined protocols (whether uniphasic, biphasic or multiphasic) for delivery simplifies the procedure, providing the same amount of contrast media to different patients under the same protocol can produce very different results in image contrast and quality. Furthermore, with the introduction of the newest MDCT scanners, an open question in clinical practice and in the CT literature is whether the standard contrast protocols used with single-slice, helical scanners will translate well to procedures using the MDCT machines. See, for example, Cademartiri, F. and Luccichenti, G., et al., "Sixteen-row multislice computed tomography: basic concepts, protocols, and enhanced clinical applications." Semin Ultrasound CT MR 25(1): 2-16 (2004).

A few studies have attempted quantitative analyses of the injection process during CT angiography (CTA) to improve and predict arterial enhancement. For example, Bae and coworkers developed pharmacokinetic (PK) models of the contrast behavior and solved the coupled differential equation system with the aim of finding a driving function that causes the most uniform arterial enhancement. K. T. Bae, J. P. Heiken, and J. A. Brink, "Aortic and hepatic contrast medium enhancement at CT. Part I. Prediction with a computer model," Radiology, vol. 207, pp. 647-55 (1998); K. T. Bae, "Peak contrast enhancement in CT and MR angiography: when does it occur and why? Pharmacokinetic study in a porcine model," Radiology, vol. 227, pp. 809-16 (2003); K. T. Bae et al., "Multiphasic Injection. Method for Uniform Prolonged Vascular Enhancement at CT Angiography: Pharmacokinetic Analysis and Experimental Porcine Method," Radiology, vol. 216, pp. 872-880 (2000); U.S. Pat. Nos. 5,583,902, 5,687,208, 6,055,985, 6,470,889 and 6,635,030, the disclosures of which are incorporated herein by reference. An inverse solution to a set of differential equations of a simplified compartmental model set forth by Bae et al. indicates that an exponentially decreasing flow rate of contrast medium may result in optimal/constant enhancement in a CT imaging procedure. However, the injection profiles computed by inverse solution of the PK model are profiles not readily realizable by most CT power injectors without major modification.

In another approach, Fleischmann and coworkers treated the cardiovascular physiology and contrast kinetics as a "black box" and determined its impulse response by forcing the system with a short bolus of contrast (approximating an unit impulse). In that method, one performs a Fourier transform on the impulse response and manipulates this transfer function estimate to determine an estimate of a more optimal injection trajectory than practiced previously. D. Fleischmann and K. Hittmair, "Mathematical analysis of arterial enhancement and optimization of bolus geometry for CT angiography using the discrete Fourier transform," *J Comput Assist Tomogr*, vol. 23, pp. 474-84 (1999), the disclosure of which is incorporated herein by reference.

Uniphasic administration of contrast agent (typically, 100 to 150 mL of contrast at one flow rate) results in a non-uniform enhancement curve. See, for example, D. Fleischmann and K. Hittmair, supra; and K. T. Bae, "Peak contrast enhancement in CT and MR angiography: when does it occur and why? Pharmacokinetic study in a porcine model," *Radiology*, vol. 227, pp. 809-16 (2003), the disclosures of which are incorporated herein by reference. Fleischmann and Hittmair thus presented a scheme that attempted to adapt the administration of contrast agent into a biphasic injection tailored to the individual patient with the intent of optimizing imaging of the aorta. A fundamental difficulty with controlling the presentation of CT contrast agent is that hyperosmolar drug diffuses quickly from the central blood compartment. Additionally, the contrast is mixed with and diluted by blood that does not contain contrast.

Fleischmann proscribed that a small bolus injection, a test bolus injection, of contrast agent (16 ml of contrast at 4 ml/s) be injected prior to the diagnostic scan. A dynamic enhancement scan was made across a vessel of interest. The resulting processed scan data (test scan) was interpreted as the impulse response of the patient/contrast medium system. Fleischmann derived the Fourier transform of the patient transfer function by dividing the Fourier transform of the test scan by the Fourier transform of the test injection. Assuming the system was a linear time invariant (LTI) system and that the desired output time domain signal was known (a flat diagnostic scan at a predefined enhancement level) Fleischmann derived an input time signal by dividing the frequency domain representations of the desired output by that of the patient transfer function. Because the method of Fleischmann et. al. computes input signals that are not realizable in reality as a result of injection system limitations (for example, flow rate limitations), one must truncate and approximate the computed continuous time signal.

In addition to control of a powered injector to provide a desired time enhancement curve, the operation of a powered injector should be carefully controlled to ensure the safety of the patient. For example, it is desirable not to exceed a certain fluid pressure during an injection procedure. In addition to potential hazards to the patient (for example, vessel damage) and potential degradation of the diagnostic and/or therapeutic utility of the injection fluid, excessive pressure can lead to equipment failure. Disposable syringes and other fluid path components (sometimes referred to collectively as a "disposable set") are typically fabricated from plastics of various burst strengths. If the injector causes pressure in the fluid path to rise above the burst strength of a disposable fluid path element, the fluid path element will fail.

In addition to problems of control with current injector systems, many such systems lack convenience and flexibility in the manner in which the injector systems must be operated. In that regard, the complexity of medical injection procedures and the hectic pace in all facets of the health care industry place a premium on the time and skills of an operator.

Although advances have been made in the control of fluid delivery systems to, for example, provide a desirable time enhancement curve and to provide for patient safety, it remains desirable to develop improved devices, systems, and method for delivery of fluids to a patient.

SUMMARY OF THE INVENTION

In one aspect, the present invention provides system including a parameter generation system to determine parameters of at least one phase (for example, of the plurality of phases) of an injection procedure based at least in part upon a type of the injection procedure. The parameter generator system determines the amount of a pharmaceutical that is to be delivered to a patient at least in part on the basis of the concentration of an agent in the pharmaceutical and at least on part on the basis of a function that depends upon and varies with a patient parameter. The patient parameter can, for example, be weight, body mass index, body surface area or cardiac output. The pharmaceutical can, for example, include a contrast enhancing agent for use in an imaging procedure.

In one embodiment at least a first portion of the volume of the pharmaceutical to be injected is calculated using the formula: $V_1$=weight*X*Y, wherein $V_1$ is the first portion of the volume, X is a function of weight, and Y is a function of the concentration of contrast enhancing agent in the pharmaceutical. X can, for example, be determined for a particular patient weight (or other patient parameter) from an algorithm in which X is calculated as a function of weight. X can alternatively be determined for a particular patient weight (or other patient parameter) from a table wherein X is set forth as a function of weight.

$V_1$ can, for example, be the volume of the pharmaceutical to be delivered in a phase in which only the pharmaceutical is to be delivered. The parameter generation system can also determine a volume $V_2$ of pharmaceutical to be delivered in at least a second phase in which both the pharmaceutical and a diluent are to be delivered to the patient. The flow rate of the pharmaceutical in the first phase can be established to be approximately equal to the flow rate of admixture of pharmaceutical and diluent fluid in the second phase.

The flow rate of the pharmaceutical (in the first phase) can, for example, be calculated by dividing $V_1$ by an injection duration of the first phase. The injection duration of the first phase can, for example, be determined by adding a factor K to a scan duration of an imaging system. K can, for example, be in the range of approximately 0 to approximately 10 seconds. A minimum first phase injection duration can also be input into the parameter generation system.

The volume $V_2$ of contrast to be delivered to the patient in the second phase can, for example, be calculated based at least in part on a patient parameter. The patient parameter can, for example, be weight, body mass index, body surface area or cardiac output. In one embodiment, the volume $V_2$ is determined by the formula $V_2$=weight*Z, wherein Z is a constant.

The volume of saline to be delivered to the patient can, for example, be calculated from $V_2$ and a ratio of pharmaceutical to diluent fluid in the second phase.

The parameter generation system can determine whether the total volume of the pharmaceutical to be delivered to the patient in all phases exceeds the volume pharmaceutical available for delivery to the patient (for example, exceeds the volume of a container for the pharmaceutical from which pressurized pharmaceutical will be delivered to the patient). In such an embodiment, the parameter generation system can include rules to reduce the total volume of the pharmaceutical if the determined total volume exceeds the available volume. For example, the total volume can reduced so that the reduced total volume of the pharmaceutical to be delivered to the patient does not exceed the volume of a container from which the pharmaceutical is to be delivered.

Further, a determination can be made by the parameter generation system of whether the flow rate of the pharmaceutical during the first phase will exceed a predetermined flow rate. In such an embodiment, the parameter generation system can include rules to, for example, adjust $V_1$ so that the predetermined flow rate is not exceeded.

A total volume of pharmaceutical to be delivered to the patient in all phases is preferably determined by the parameter generation system. In the case of, for example, use of an unfilled container for fluid delivery, a container from which the pharmaceutical is to be delivered can then be filled with a load volume of pharmaceutical based upon the determined total volume of pharmaceutical to be delivered by the patient. The container can, for example, be a syringe. However, the parameter generation systems of the present invention are also suitable for use in connection with prefilled containers (for example, syringes) or in connection with continuous or multipatient fluid delivery systems that can include large, bulk containers of pharmaceutical and/or agent.

In several embodiments, an initial protocol is determined by the parameter generation system to, for example, determine the total volume. The initial protocol can then be adjusted based upon a characterization of the cardiovascular system of the patient.

A test bolus of the pharmaceutical can, for example, be performed to characterize the cardiovascular system of the patient. The initial protocol can, for example, be adjusted at least in part on the basis of a time to peak enhancement of the test bolus. In several embodiments, the initial protocol is adjusted at least in part on the basis of a time to peak enhancement of the test bolus and a level of enhancement of the peak enhancement.

A scan delay can, for example, be determined at least in part on the basis of the time to peak enhancement. In one embodiment, scan delay is calculated by the formula: scan delay=time to peak+C, wherein C is a function of a patient parameter such as weight, body mass index, body surface area or cardiac output. C can, for example, be a function of weight, body mass index, body surface area or cardiac output in the case of scan durations of at least a predetermined time, and C can be set to a predetermined value in the case of scan durations less than the predetermined time.

A determination can be made as to whether to adjust the ratio of the pharmaceutical to the diluent fluid in the second phase at least in part on the basis of the level of the peak enhancement.

A duration of the second phase can be calculated according to the formula: $D_{DF}$=Scan Delay+Scan Duration−$D_C^{Diag}$, wherein $D_C^{Diag}$ is a duration of the first phase and Scan Duration is a scan duration of the imaging system. $D_C^{Diag}$ can, for example, be determined by adding a factor K to the scan duration of an imaging system. K can, for example, be in the range of approximately 0 to approximately 10 seconds. A minimum first phase injection duration can be input into the parameter generation system.

In another aspect, the present invention provides a system including parameter generation system to determine parameters of at least one phase (for example, of a plurality of phases) of an injection procedure in which a pharmaceutical including an image contrast enhancement agent is delivered to a patient wherein the parameter generation system includes an algorithm to determine parameters based at least in part upon a type of the injection procedure, a determined time to peak enhancement and a level of peak enhancement. As used herein, the term "algorithm" refers to a procedure for determining the parameters, which can, for example, be embodied in software.

The time to peak enhancement and the level of peak enhancement can, for example, be determined at least in part by an injected bolus of the pharmaceutical into a patient. The time to peak enhancement and the level of peak enhancement can also be determined at least in part by a model of propagation of the pharmaceutical in a patient.

A volume of the pharmaceutical to be loaded and optionally a volume of a diluent to be loaded can, for example, be determined by determination of initial parameters of the injection procedure at least in part on the basis of at least one parameter of the patient and a determined scan duration. The at least one parameter of the patient can, for example, be weight, body mass index, body surface area or cardiac output.

At least one of the time to peak enhancement and the level of peak enhancement can be used to adjust the initial parameters.

In a further aspect, the present invention provides a system including a parameter generation system to determine parameters of a diagnostic injection protocol including at least one phase in which a pharmaceutical including an image contrast enhancement agent is delivered to/injected into a patient. The parameter generation system includes an algorithm adapted to determine parameters of an initial protocol using information available prior to characterization of a cardiovascular system of the patient and an algorithm to adjust the parameters of the initial protocol based at least in part on the characterization of the cardiovascular system to determine the parameters of the diagnostic injection protocol.

As described above, the initial protocol can, for example, be used to determine a total volume of pharmaceutical to be injected into the patient in all phases. A container from which the pharmaceutical is to be delivered can be filled with a load volume of pharmaceutical based upon the determined total volume of pharmaceutical to be delivered to the patient. The container can, for example, be a syringe. The parameter generation system is also suitable for use in connection with prefilled containers (for example, syringes) or in connection with continuous or multipatient fluid delivery systems.

In another aspect, the present invention provides a system including a parameter generation system to determine parameters of a diagnostic injection protocol including at least one phase in which a pharmaceutical including an image contrast enhancement agent is injected into a patient. The parameter generation system includes an algorithm to determine a scan delay for the patient (that is, on a per-patient or individualized basis).

The scan delay can, for example, be determined at least in part on the basis of the time to peak enhancement (for example, as determined during a test injection). For example, the scan delay can be calculated by the formula: scan delay=time to peak+C, wherein C is a function of a patient parameter such as weight, body mass index, body surface area and/or cardiac output. C can, for example, be a function of a parameter such as weight, body mass index, body surface area and/or cardiac output in the case of scan durations of at least a predetermined time, and C can be set to a predetermined value in the case of scan durations less than the predetermined time.

In another aspect, the present invention provides system including a parameter generation system to determine parameters of a diagnostic injection protocol including at least one admixture phase in which an admixture including a pharmaceutical including an image contrast enhancement agent and a diluent is injected into a patient, wherein the parameter generation system includes an algorithm to determine a ratio of pharmaceutical to diluent in the at least one admixture phase for the patient (that is, on a per-patient or individualized basis). The ratio can, for example, be determined based at least in part upon a characterization of the cardiovascular system of the patient. The ratio can also be determined based at least in part upon the basis of a patient parameter such as weight, body mass index, body surface area, and/or cardiac output or upon a level of peak enhancement.

In a further aspect, the present invention provides a system as described above further including at least one pressurizing mechanism; at least a first fluid container operably associated with the at least one pressurizing mechanism, the first fluid container being adapted to contain a pharmaceutical comprising a contrast enhancing agent to be injected in an imaging procedure; at least a second fluid container operably associated with the at least one pressurizing mechanism, the second fluid container adapted to contain a diluent fluid; a controller operably associated with the at least one pressurizing mechanism, the controller comprising a programming system to allow programming of an injection protocol including one or a plurality of phases. The system can further include an imaging system. The parameter generation system can, for example, be in communicative connection with at least one of the imaging system or the controller of the pressuring mechanism.

In another aspect, the present invention provides an injector including a parameter generation system as described herein or of which the parameter generation system is a component.

In still a further aspect, the present invention provides an imaging system including a parameter generation system as described herein or of which the parameter generation system is a component.

The present invention also provides method of determining parameters as set forth in the systems described above. The present invention also provides parameter generation systems as described above.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 24E illustrates a table of contrast loading results using values set forth in Table 1 and the dual flow loading coefficient.

FIG. 24F illustrates a table of total contrast volume, including a 20 ml test bolus.

FIG. 24G illustrates a table of total Iodine dose for loaded contrast volumes, including a 20 ml test bolus.

FIG. 33A illustrates the workflow diagram of FIG. 26 in which a patient weight input step is encircled with circle A and a corresponding graphical user interface in which patient weight can be selected from a plurality of weight ranges.

FIG. 33E illustrates the workflow diagram of FIG. 26 in which an initial diagnostic protocol computation step is encircled with circle E and a corresponding graphical user interface wherein the user is prompted to have the protocol generation system generate the protocol.

FIG. 33F illustrates the workflow diagram of FIG. 26 in which the data transfer step of data from a test bolus to the protocol generation interface is encircled with circle F and a corresponding graphical user interface for manual data entry of the time to peak and peak enhancement.

FIG. 33G illustrates the workflow diagram of FIG. 26 in which the point at which the determination of diagnostic protocol has been completed by the protocol generation interface and the diagnostic injection can be initiated is encircled with circle G and a corresponding graphical user interface setting forth the computed diagnostic protocol.

FIG. 34B illustrates volumetric flow rates and iodine administration rates for a contrast only phase (phase 1) and a dual flow or admixture phase as determined by an embodiment of a protocol generation process of the present invention.

FIG. 35A illustrates results obtained using a protocol generated by a protocol generation process of the present invention as compared to the results obtained using a uniphasic protocol, a biphasic protocol and a fixed dual flow protocol.

DETAILED DESCRIPTION OF THE INVENTION

As used herein with respect to an injection procedure, the term "protocol" refers to a group of parameters such as flow rate, volume injected, duration etc. that define the amount of fluid(s) to be delivered to a patient during an injection procedure. Such parameters can change over the course of the injection procedure. As used herein, the term "phase" refers generally to a group of parameters that define the amount of fluid(s) to be delivered to a patient during a period of time (or phase duration) that can be less than the total duration of the injection procedure. Thus, the parameters of a phase provide a description of the injection over a time instance corresponding to the time duration of the phase. An injection protocol for a particular injection procedure can, for example, be described as uniphasic (a single phase), biphasic (two phases) or multiphasic (two or more phases, but typically more than two phases). Multiphasic injections also include injections in which the parameters can change continuously over at least a portion of the injection procedure.

Figure 1:
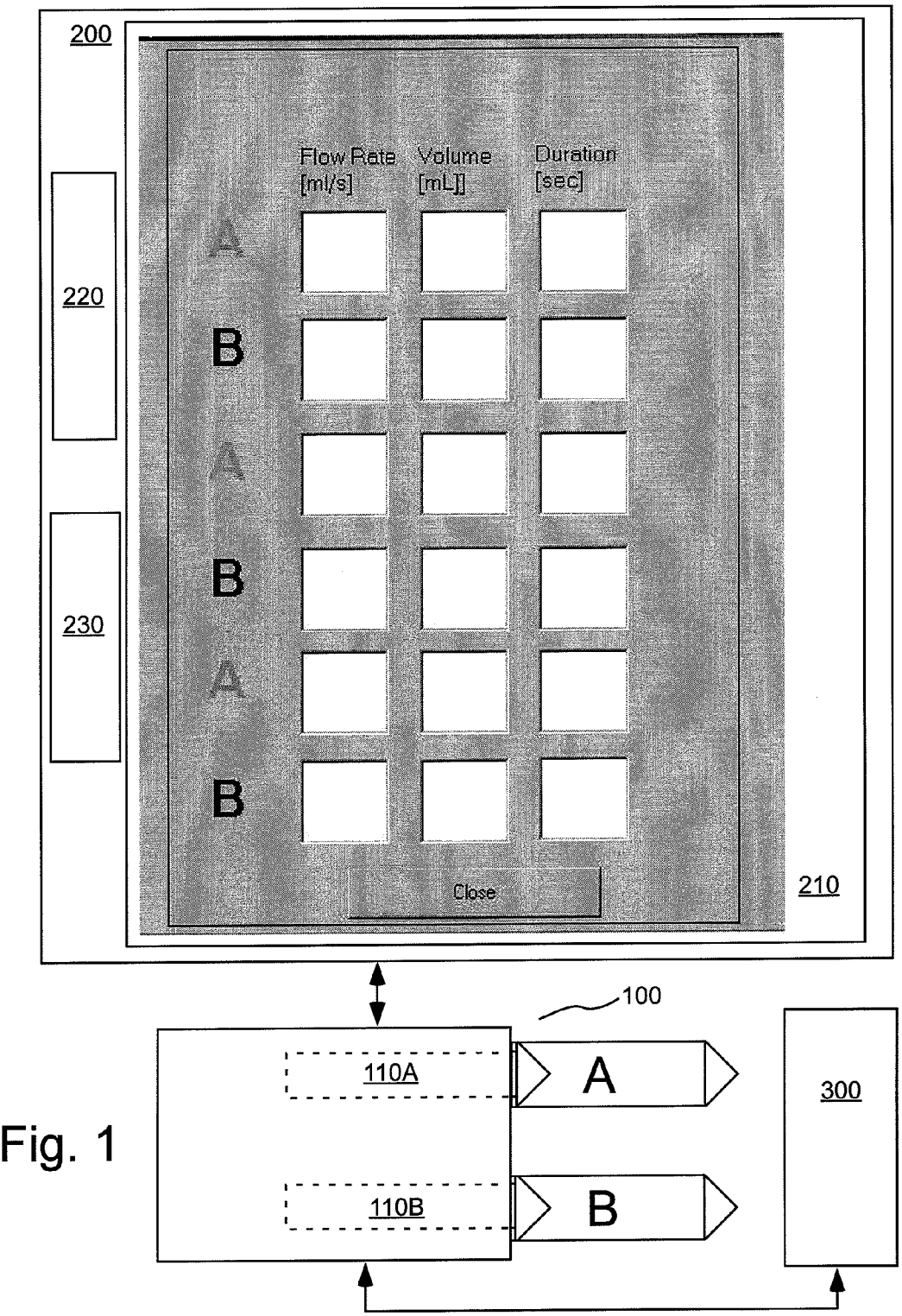
FIG. 1 illustrates an embodiment of a multi-phasic Graphical User Interface (GUI) for use in the present invention to set forth parameters for a plurality of phases for a two-syringe injector also illustrated in FIG. 1.

In several embodiments of the present invention, an injection system (such as a dual syringe injector system 100 as illustrated in FIG. 1 and as, for example, disclosed in U.S. Pat. No. 6,643,537 and Published U.S. Patent Application Publication No. 2004-0064041) for use with the present invention includes two fluid delivery sources (sometimes referred to as source "A" and source "B" herein; such as syringes) that are operable to introduce a first fluid and/or a second fluid (for example, contrast medium, saline, etc.) to the patient independently (for example, simultaneously, simultaneously in different volumetric flow proportion to each other, or sequentially or subsequent to each other (that is, A then B, or B then A)).

In the embodiment of FIG. 1, source A is in operative connection with a pressurizing mechanism such as a drive member 110A, and source B is in operative connection with a pressurizing mechanism such as a drive member 110B. The injection system includes a controller 200 in operative connection with injector system 100 that is operable to control the operation of drive members 110A and 110B to control injection of fluid A (for example, contrast medium) from source A and injection of fluid B (for example, saline) from source B, respectively. Controller 200 can, for example, include a user interface comprising a display 210. Controller 200 can also include a processor 220 (for example, a digital microprocessor as known in the art) in operative connection with a memory 230. Imaging system 300 can, for example, be a CT system, a Magnetic Resonance Imaging (MRI) system, an ultrasound imaging system, a Positron Emission Tomography (PET) system or another imaging system. The injection system can be in communicative connection with imaging system 300 and one, a plurality or all the components of the injection system and imaging system 300 can be integrated.

In several embodiments of the present invention, phase variables or parameters as described above are populated within a phase programming mechanism (see FIG. 1 for an embodiment of a user interface therefor that can, for example, be used with injector system 100) based on one or more parameters of interest, including, for example, but not limited to, contrast agent concentration (for example, iodine concentration in the case of a CT procedure), a patient parameter (for example, body weight, height, gender, age, cardiac output, etc.) the type of scan being performed, and the type of catheter inserted into the patient for intravascular access. As discussed above, differences in dosing requirements for different patients during imaging and other procedures have been recognized. For example, U.S. Pat. Nos. 5,840,026 and 6,385,483, assigned to the assignee of the present invention, the disclosures of which are incorporated herein by reference, disclose devices and methods to customize the injection to the patient using patient specific data derived before or during an injection. Likewise, PCT International Patent Application No. PCT/US05/41913, entitled MODELING OF PHARMACEUTICAL PROPAGATION, filed Nov. 16, 2005, claiming the benefit of U.S. Provisional Patent Application Ser. No. 60/628,201, assigned to the assignee of the present invention, the disclosures of which are incorporated herein by reference, also discloses customization of injections to a patient using patient specific data and sets forth a number of models to describe a time enhancement output for a given input or protocol.

Because optimal sets of flow rates and volumes are not readily known to the operator of the injector, the present invention eases the task of an operator in, for example, scanning patients in an imaging procedure by providing a set of injection protocols that are predetermined as being effective for the type of procedure being performed. For example, such protocols can be established in the clinical literature, established by collection of patient data over time (by, for example, employing artificial intelligence techniques, statistical means, adaptive learning methodologies, etc.), established through mathematical modeling or otherwise established for a type of procedure being performed.

The operator can, for example, first choose the concentration of contrast agent (for example, concentration of iodine in a CT procedure) to be delivered into a patient. This choice is made, for example, by a selection mechanism, or by direct input of numerical values on the graphical user interface. The clinical operator can also select the gauge of the catheter inserted into that specific patient. Catheter size can be entered so that in subsequent steps, when the volumetric flow rate is determined, the pressure head to be developed in a disposable fluid path set can be calculated as described below (for example, via a computer program). Alternatively, one or more sensors can be provided to sense catheter size and provide this information to the injector.

The clinical operator can, for example, control the injection system by either entering volumes and flow rates manually into the fields provided on the User Interface (see FIG. 1) or by entering a "protocol wizard or generation mode", "helper mode" or "operator assist mode" as described herein. In an operator assist mode, such fields are automatically populated. If the operator chooses to enter the operator assist mode, the operator can be presented with a mechanism or mode (see, for example, FIG. 2) of selecting an organ or vascular system to be scanned.

Figure 2:
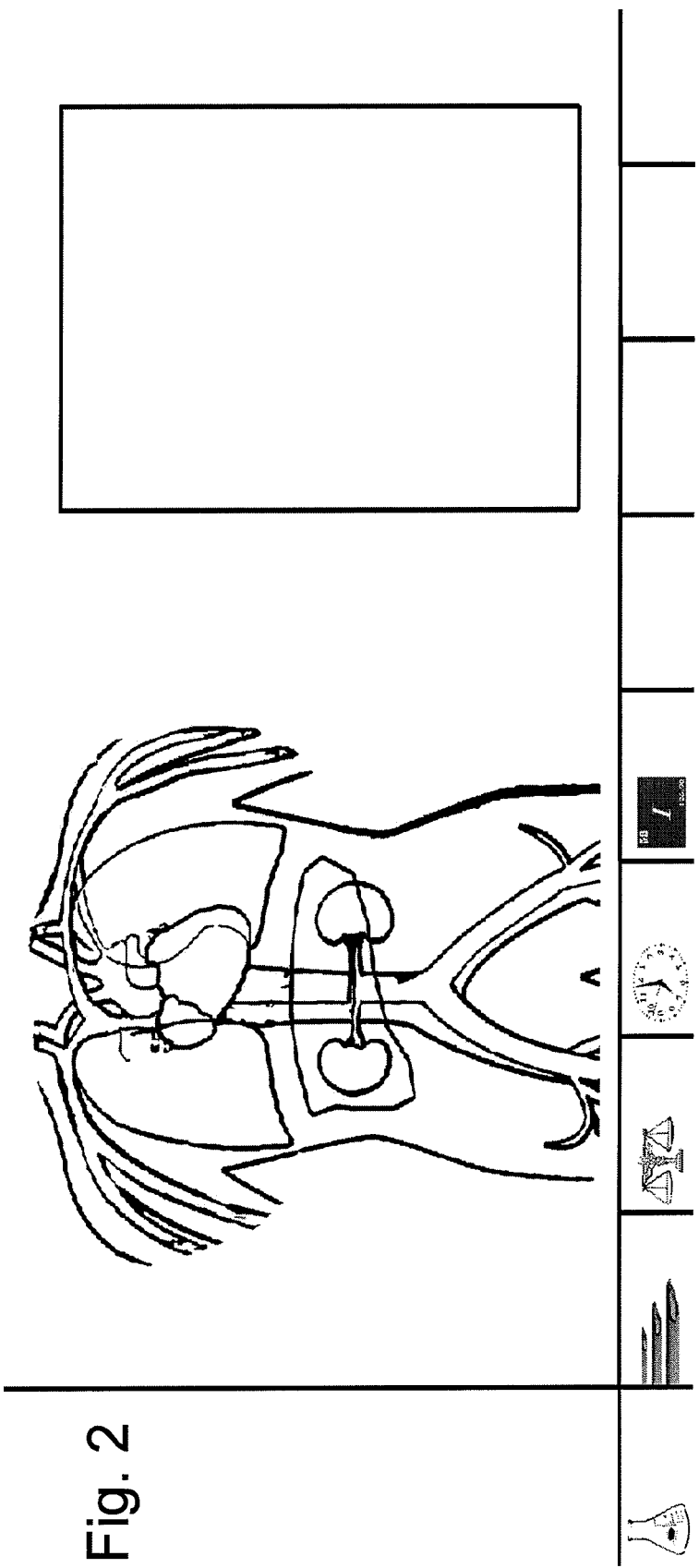
FIG. 2 illustrates an embodiment of a graphical interface from which an operator can choose a vascular region of interest for imaging.

The present invention provides systems, devices and methodologies or algorithms that predict the flow rate profile (which can be constant or varying during a phase) and volume of contrast agent to deliver depending upon the procedure and the region of interest chosen. For example, an operator can choose the heart, descending aorta or ascending aorta (referred to as cardiac imaging, a form of Computed Tomography Angiography (CTA)). One embodiment of a graphical interface from which the operator chooses the vascular region of interest, and which follows the work flow described herein, is depicted in FIG. 2. The operator can, for example, choose a region of interest by highlighting (for example, using a touch screen or a mouse controlled cursor) a region of interest on an illustration of the body set forth on the user interface or can choose a region of interest from a menu such as a pull down menu. Hierarchical groupings of regions of interest can be provided.

In addition to use of the injector system to affect the above-identified choices, the choices set forth above can also or alternatively be made on a user-interface on the imaging system or scanner and/or from a database on the imaging system or scanner. In the case that the choices are made via an interface or database resident on the scanner, the data can then be transmitted to the injector. Moreover, the interface can exist solely on the scanner/imaging system. In this case, the final protocol can be transmitted to the injection system. Likewise, the interface or database can exist on a machine or system separate from the injector and the scanner. Data (for example, protocols) can be transmitted from that system to the injector. A communication interface that may be used herein is disclosed in U.S. Pat. No. 6,970,735, the contents of which is incorporated herein by reference.

Figure 3:
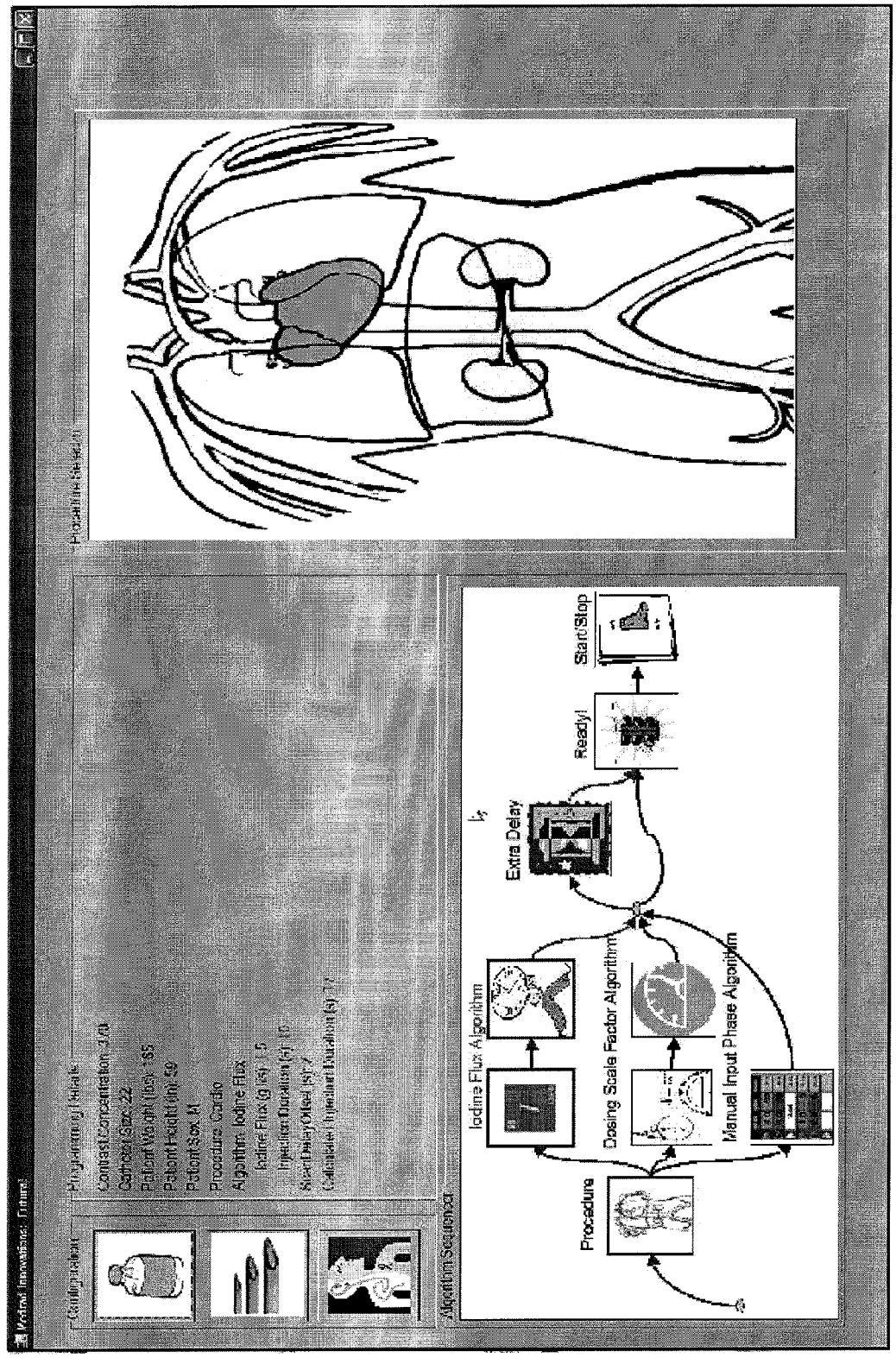
FIG. 3 illustrates an embodiment of a graphical interface of a proposed work flow environment for use in the present invention.

Upon choosing the region to be imaged, the operator can, for example, be prompted to enter values for other variables (for example, patient physiological variables such as the patient's weight, height, gender, etc.). An example of an embodiment or implementation of this is to provide a keypad on the user interface into which the operator enters the patient's weight in pounds or kilograms. In another embodiment, the operator chooses a weight range from among low, mid and high ranges. Such variables can also be measured by one or more sensing devices associated with the system and/or read electronically or digitally from patient records as may be kept in a hospital database. The steps necessary to conduct a contrast injection can be presented to the operator as depicted in FIG. 3. In the embodiment of FIG. 3, the operator can, for example, be prompted in an order (for example, a suggested or required sequential order) natural to the type of imaging procedure to be performed. The operator can, for example, be given the ability to choose a vascular region or organ of the body to image, the type of algorithm to conduct the injection, and an ability to change the type of contrast, catheter gauge, and/or physical attributes of the patient.

Figure 4:
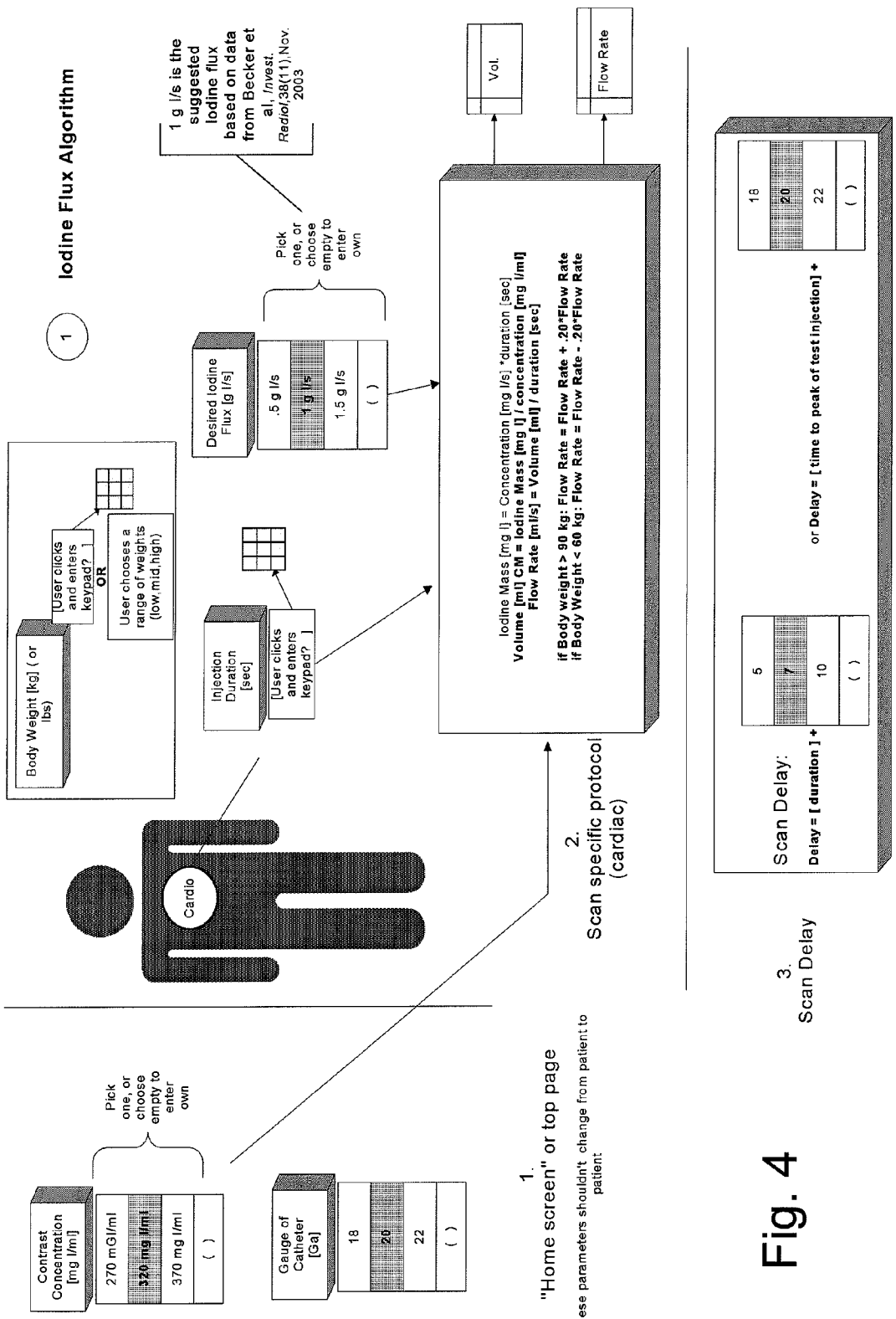
FIG. 4 illustrates an embodiment of an iodine flux algorithm for use in the present invention.
Figure 5:
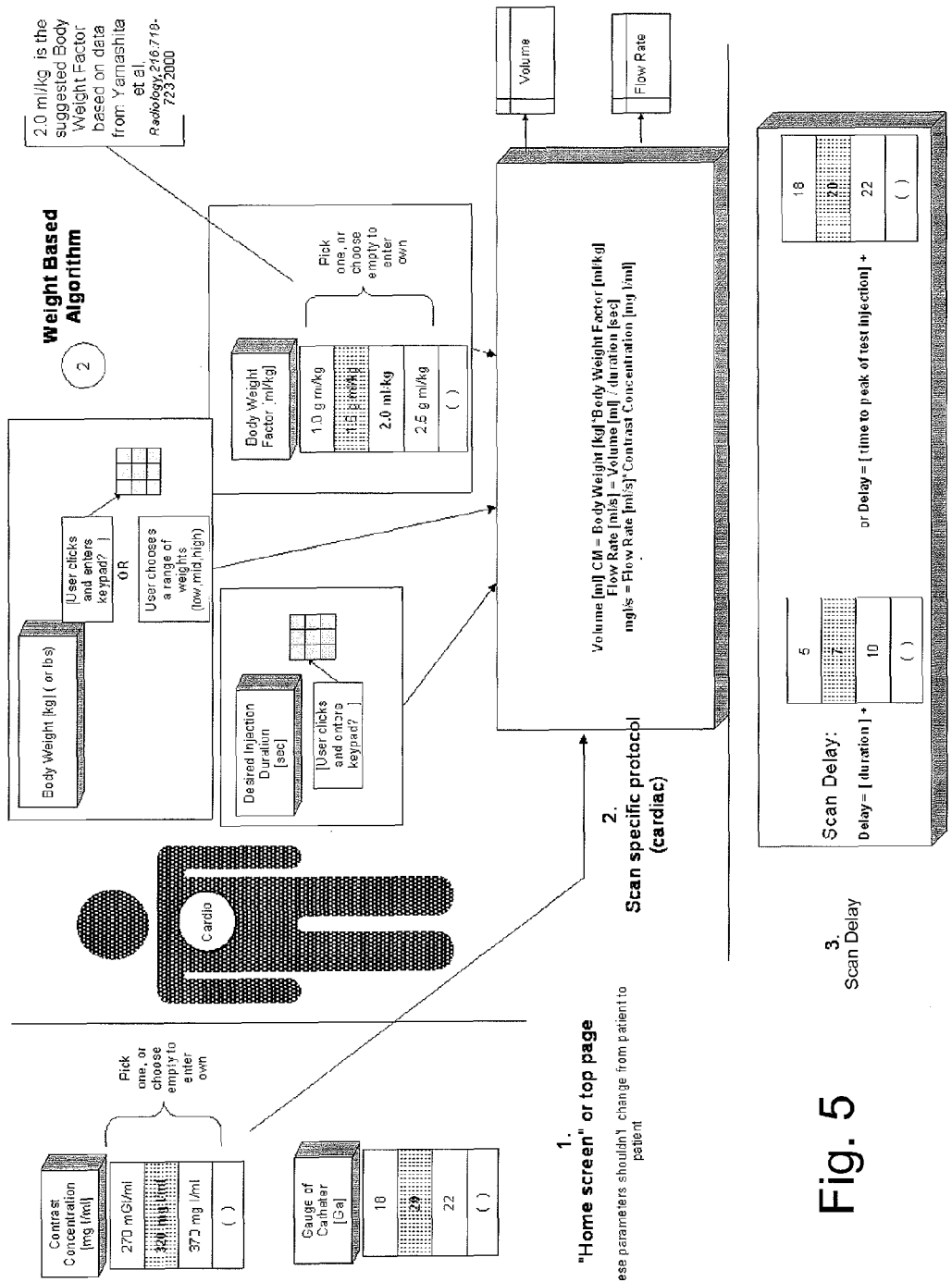
FIG. 5 illustrates an embodiment of a weight based algorithm for use in the present invention.
Figure 6:
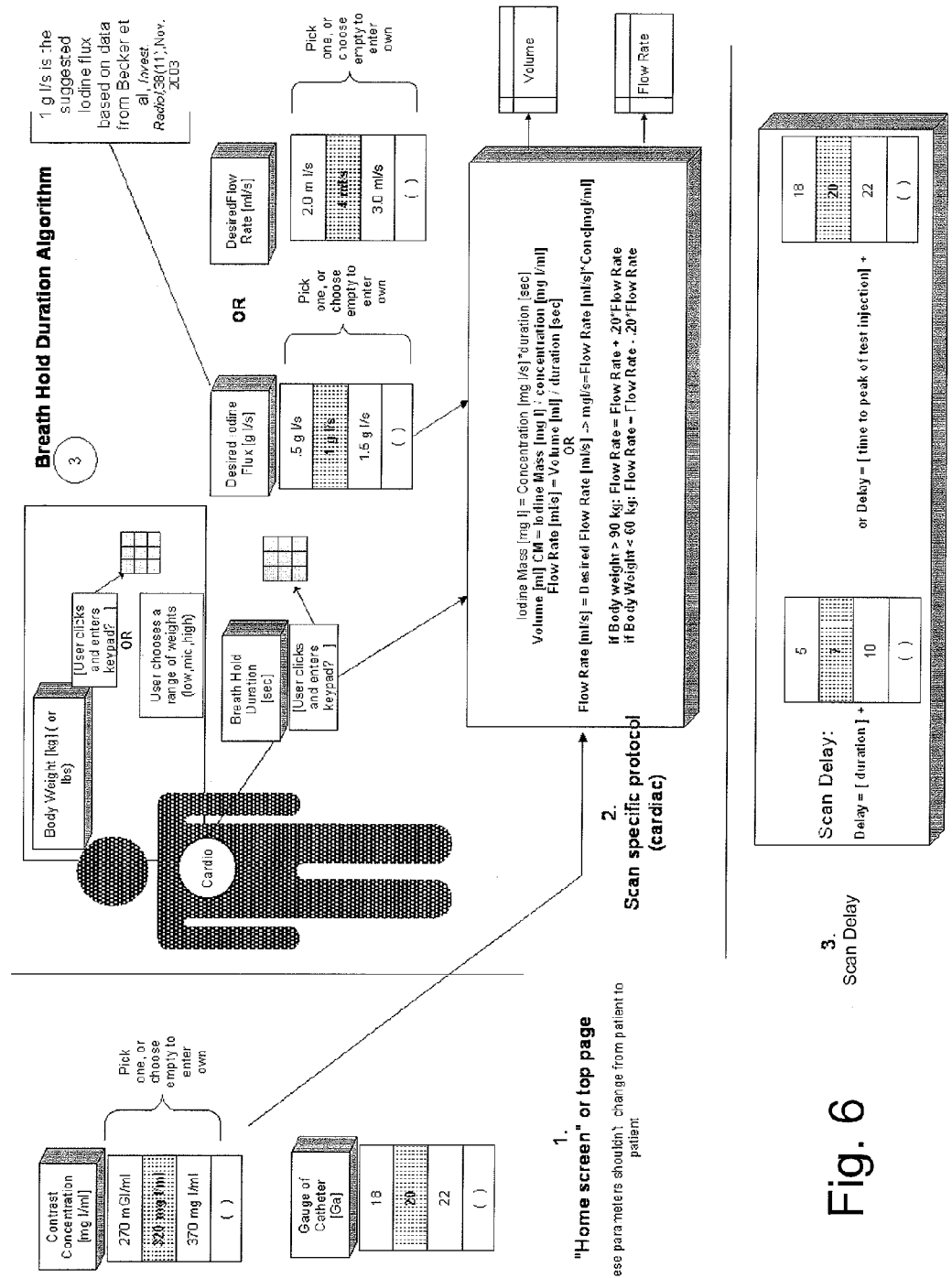
FIG. 6 illustrates an embodiment of a breath hold duration algorithm for use in the present invention.

As discussed above, the operator can be presented with a choice of the type of algorithm the operator would like the system to use to produce a set of flow rates and volumes (that is, phase parameters) for that patient. In the case of cardiac imaging, algorithm choices can, for example, include: (i) an Iodine Flux Algorithm, (see FIG. 4) (ii) a Weight Based Algorithm (see FIG. 5), (iii) a Breath Hold Duration Algorithm (see FIG. 6) or (iv) a "Cardiac" algorithm (see FIGS. 24A through 35B) or other body region specific algorithm. One or more of these algorithms can, for example, be based upon empirical data (for example, as published in the radiological medical literature). Additional algorithms can be included for other types or classes of imaging procedures. The methodologies and/or logic for embodiments of the four algorithms described above are set forth in FIGS. 4, 5, 6, and 24A through 35B, respectively. Upon entering the data required for a particular algorithm, the operator can be queried if the operator wishes to perform a test injection (or timing injection). If the operator chooses yes, the software can provide that, for example, two additional phases (corresponding to the test injection) must be inserted in the start of the injection protocol (for example, one phase for contrast delivery and a subsequent phase for a saline flush injection).

Based upon the selections made, the software implementing the present invention computes an injection protocol for the user's review. If the operator chooses to perform a test injection, then the first two phases of the protocol can, for example, include injection of 15 or 20 ml of contrast agent (for example, 15 ml if the patient weight <90 kg, 20 ml if the patient weight >90 kg) delivered at 4 ml/s. The second phase of the protocol can include injection of 20 ml of saline injected at 4 ml/s. The next phase or phases can, for example, include volumes and flow rates computed by one of the four algorithms discussed above or one or more other algorithms.

In a number of embodiments of the present invention, injection parameters for an injection procedure including a phase in which an admixture of contrast media and a diluent/flushing fluid (for example, saline) are calculated. In that regard, to address a number of problems associated with, for example, heart imaging, procedures have been developed which include the injection of saline following the contrast agent bolus, and, more recently, the admixture of contrast media with saline via simultaneous injection of contrast media and saline (sometimes referred to herein as "dual flow").

As discussed above, one proposed solution to non-uniform enhancement problems is injection of contrast with an exponentially decaying flow rate over time. While this technique can indeed produce more uniform contrast enhancement in a large vessel, it also reduces the maximum enhancement, which is not necessarily desirable. While, theoretically, it seems logical to believe that the exponentially decaying flow rates can help with right-heart artifacts (for example, by introducing less contrast later in the injection and mixing less with the earlier injected contrast), it has not been demonstrated or investigated. Furthermore, because the latter portion of the decayed injection is at a lower flow rate, there is a loss of momentum for that section of the bolus, slowing its entry to the right heart. While a saline push after the decayed exponential injection may help in ensuring the contrast is all "pushed" into the right heart, turbulence resulting from the mixing of contrast and blood at different flow rates may cause flow artifact within the right heart.

An alternative for reducing right heart artifact is to inject a volume of contrast at a discrete flow rate followed by an admixture of contrast and saline (with a final push of saline). The admixture can be injected at the same flow rate as the initial bolus of contrast. The admixture can be produced by the simultaneous injection of contrast and saline with, for example, a dual-syringe power injector, wherein the flow rates of contrast and saline are proportional to each other. This technique has been recently adopted in the clinical setting and initial results suggest that it reduces right heart artifact. However, in implementing such admixture protocols, there are currently no established systems or methods for determining appropriate or ideal injection parameters for a given patient (for example, initial flow rate and volume, percentage of admixture, duration of the phases, and scan delay).

In several embodiments, the present invention provides systems and methods for interfacing with the injection system to reduce clinician "guesses" at appropriate or optimal flow rate and volume parameters for a given patient. The systems and methods of the present invention provide for the consideration of a number of variables including, but not limited to, patient specific parameters such as patient weight (and other habitus indicators such as height, cardiac output, etc.), time of contrast arrival from a timing injection, contrast concentration, and total desired contrast agent (for example, iodine) load. The systems and methods of the present invention can, for example, include a per-patient saline admixture protocol generator.

Figure 7:
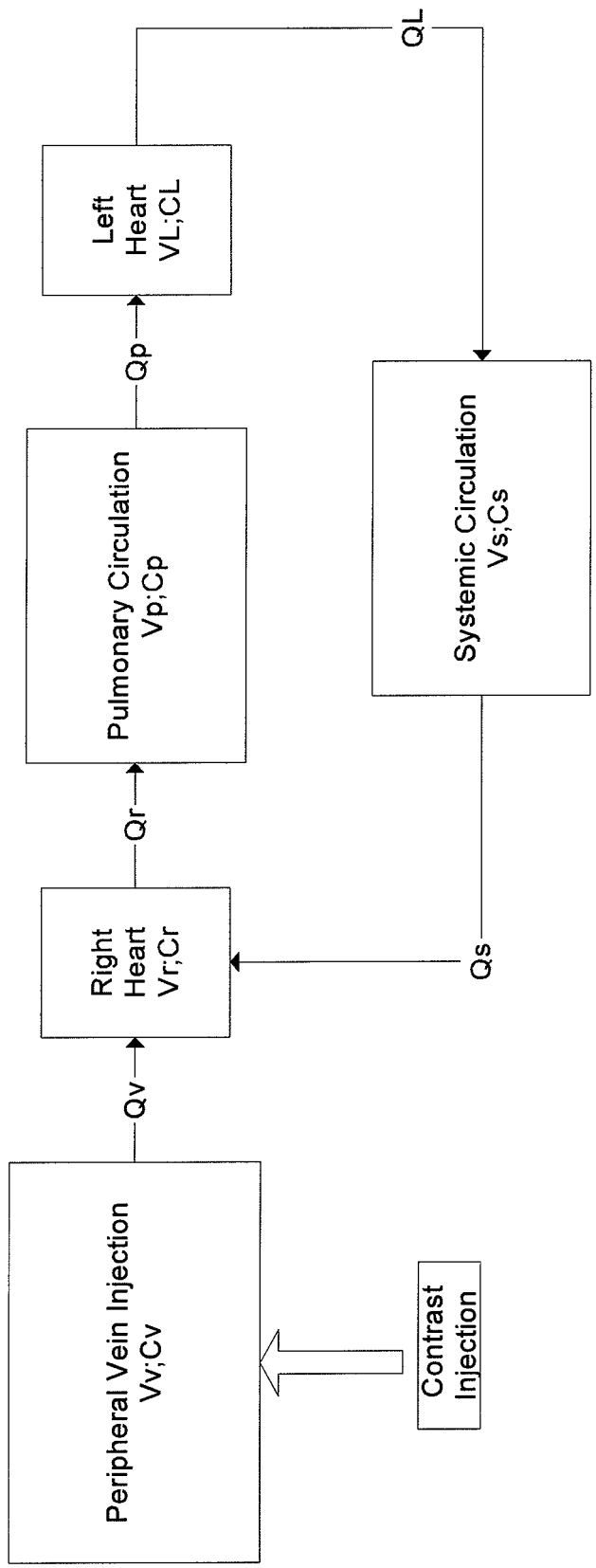
FIG. 7 illustrates an embodiment of a reduced-order compartmental model and the first-order coupled differential equation system describing this model.

The predicted contrast enhancement in the aortic/heart compartment of a human male can be used in this section to elaborate the principle of the proposed algorithm. In several studies, simulations were performed in a SIMULINK® (available from MathWorks, Inc. of Natick Mass.) implementation of a full body, Physiologic Based Pharmacokinetic Model (PBPK) PK model as described in Bae et al. See Bae, K. T., J. P. Heiken, et al., "Aortic and hepatic contrast medium enhancement at CT. Part I. Prediction with a computer model," Radiology 207(3): 647-55 (1998), and Bae, K. T., H. Q. Tran, et al., "Multiphasic injection method for uniform prolonged vascular enhancement at CT angiography: pharmacokinetic analysis and experimental porcine model," Radiology 216(3): 872-80 (1998); U.S. Pat. Nos. 5,583,902, 5,687,208, 6,055,985, 6,470,889 and 6,635,030. The modeling approach in that work recognized that the full body physiologic pharmacokinetic model taught in Bae, Heiken et al, 1998 supra, was too large and included too many unknowns to feasibly compute on a per patient basis. Bae and colleagues, therefore, approximated large parts of the anatomy with single compartments and, because first-pass enhancement dynamics are of interest, removed the capillary transfer compartments. The resulting, reduced-order model is illustrated in FIG. 7. In FIG. 7, V are the fluid volumes of the respective "compartments", C are the predicted concentrations in each "compartment", and Q are the volumetric flow rates of blood throughout the body. Q and V are estimated from anatomical data. The first-order, coupled differential equation system describing this model is formulated assuming a continuous time process and is also set forth in FIG. 7.

Figure 8A:
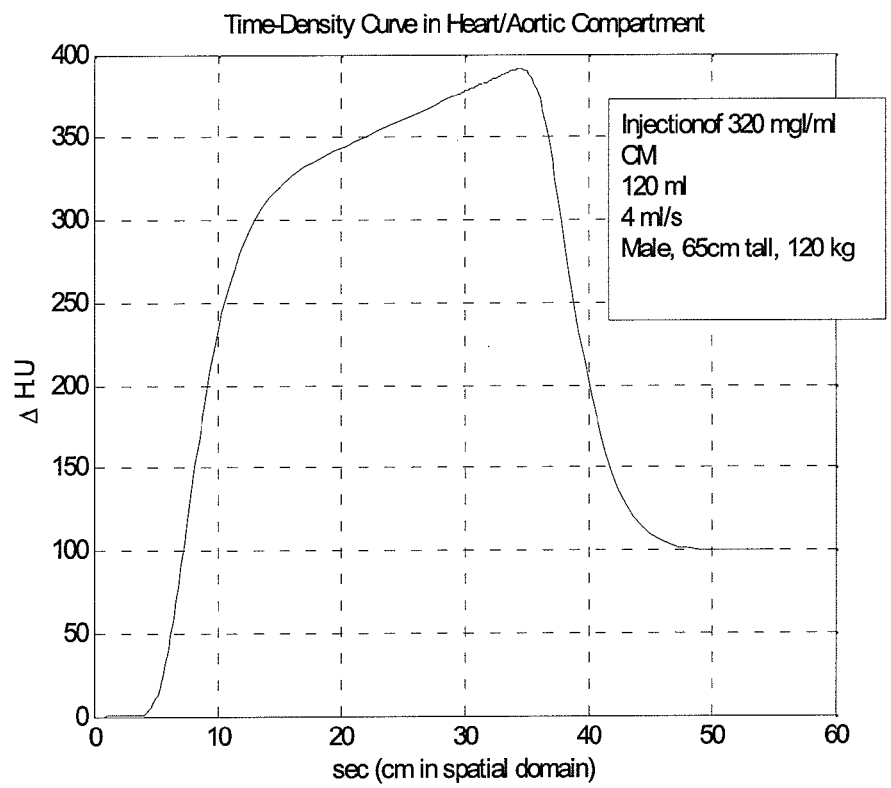
FIG. 8A illustrates a simulated enhancement curve in the heart/aortic compartment of a 65 cm, 120 kg male.
Figure 8B:
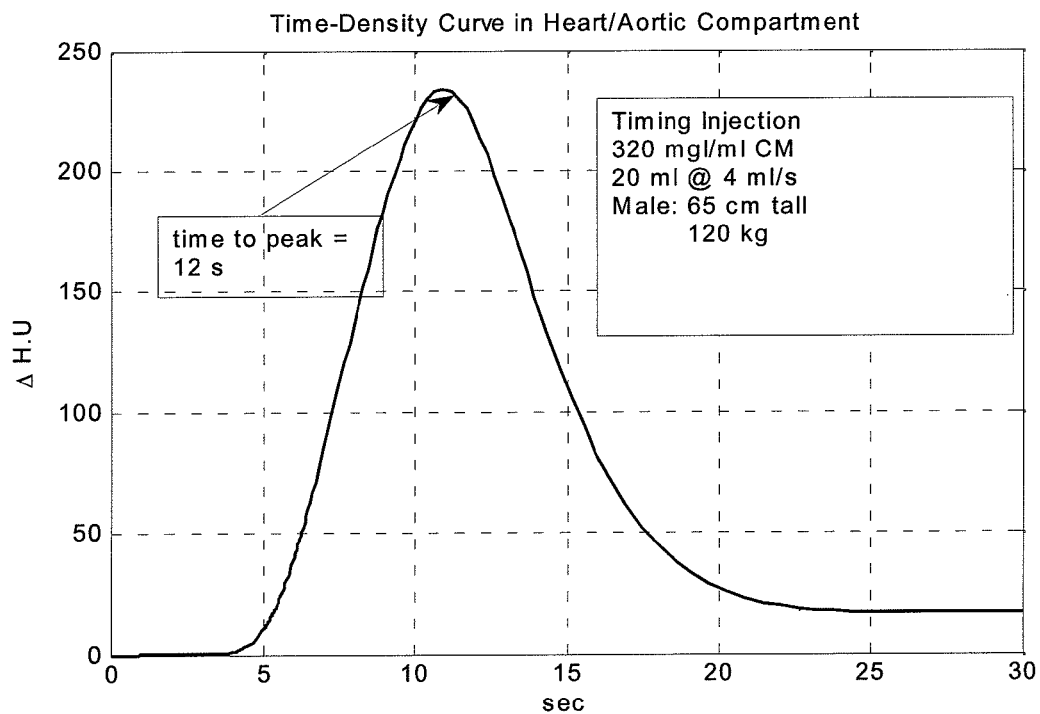
FIG. 8B illustrates a time enhancement curve to a test/timing injection from the simulated patient in FIG. 8A.
Figure 9:
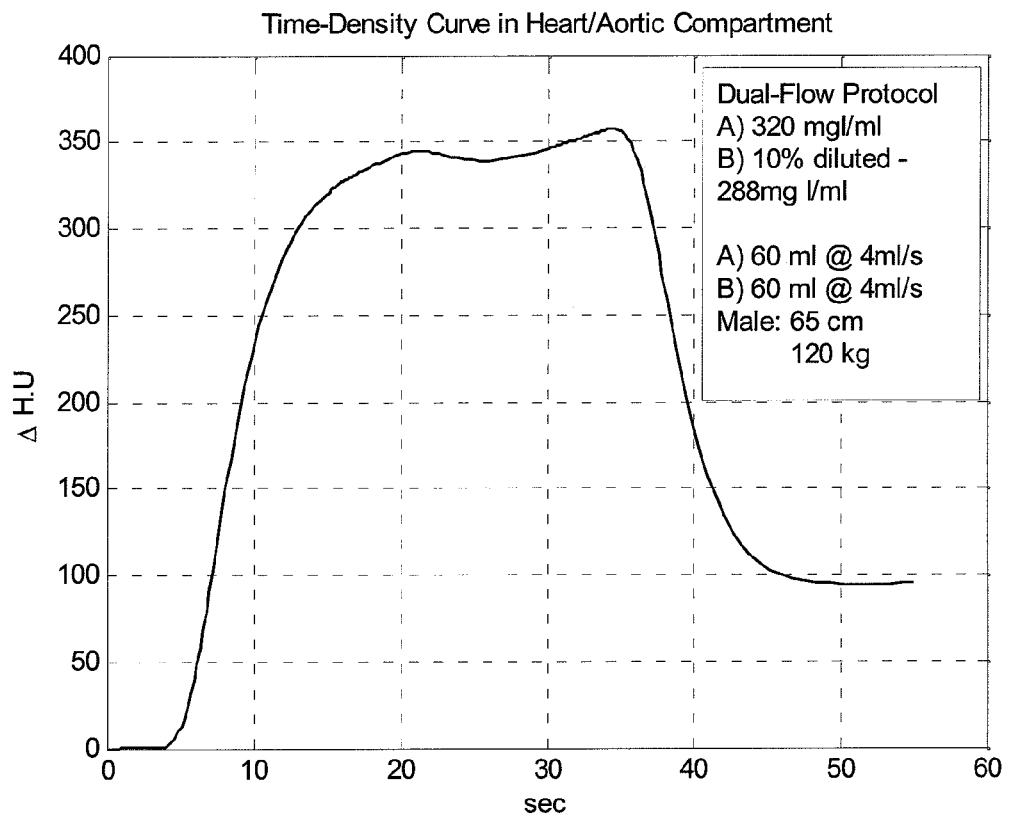
FIG. 9 illustrates a simulated time enhancement curve for the simulated patient of FIG. 8A using the proposed methodology described within.

In several studies of the present invention, an assumption was made that the aortic/heart compartment was well mixed. Although the x-axes in FIGS. 8A through 9 are labeled in time units, another assumption was that the time axis maps to spatial dimensions in the compartment of interest. FIG. 8A demonstrates the phenomenon of non-uniform contrast enhancement (caused by recirculation of contrast into the compartment). FIG. 8B presents the results of performing a small volume "test" or "timing" injection on the same patient scanned in connection with FIG. 8A (the cardiac output and central blood volume for the model were derived from anthropometric data tables). The time to peak contrast enhancement was measured as 12 seconds in FIG. 8B. The time of peak represents the transit time for a small bolus of contrast to migrate from the injection site, to the right heart, through the pulmonary circulation, and to the left heart compartment. The simulated time to peak enhancement may be less than that from a "real" patient. In that regard, the model set forth in FIG. 7 was not directly validated with human data, but was allometrically scaled from porcine data. In any event, the absolute values in these simulations are not critical. Rather, we are interested in the dynamics of the system. Noticeable in FIG. 8B is the recirculation of contrast after the peak (or first moment) of the bolus arrived in the compartment (>15 sec). The reduced-order model set forth in FIG. 7 does not reproduce with high fidelity the recirculation dynamics (for example secondary peaks).

Previous studies have concluded that if an injection duration is longer than the time for contrast arrival as computed from a timing injection, that the time to peak contrast enhancement increases linearly as the duration of injection increases. As the duration of the injection exceeds the duration of the time to peak of the test injection, the asymmetry of the enhancement curve becomes pronounced because the new contrast is mixing with the contrast already present in the compartment. This phenomenon serves as a basis of one embodiment of one algorithm of the present invention for computing admixture protocol (for example, saline plus contrast media).

FIG. 9 sets forth a time enhancement curve that was simulated with a biphasic protocol. The first phase's duration was computed to equal the time to peak enhancement of the timing bolus, plus three seconds (an arbitrary offset term). The second phase was a diluted phase (90% contrast, 10% saline) that resulted in an effective contrast concentration of 288 mgI/ml (concentration in the dilution phase=desired or programmed ratio (90/100 in this instance)* concentration of drug (320 mgI/ml)). The volume was set so that a total volume of 120 ml was injected into the patient. The flow rate was the same in both phases to maintain the momentum of the contrast into the right heart. FIG. 9 demonstrates a reduction in the asymmetric "peak" in the second half of the injection, while maintaining a contrast enhancement about 350 HU. In comparison, an exponentially decreasing flow rate technique results in a lower peak enhancement. An advantage of the injection protocol of the present invention (as compared to a decelerating injection flow rate protocol) arises in that, because the volumetric flow rate of the injected fluid is not decreasing, there is less likelihood for flow artifacts within the peripheral venous system before the heart. In that regard, injectate moving with a flow rate less than the endogenous flow rate of the venous system can result in dispersion of the contrast media because some parts of the bolus arrive to the right heart with different velocities. In the present invention, a multiphasic injection protocol can be provided in which one or more of the parameters are changed periodically or continuously over at least a period of the injection duration, wherein total flow rate is maintained constant. In this manner, for example, a concentration of contrast active agent (for example, iodine, gadolinium, etc.) delivered to a patient can be decreased over time while maintaining flow rate constant (for example, by increasing the portion of saline injected during that time). A broader, more uniform peak of enhancement can thereby be maintained (see, for example, FIG. 9). Moreover, that uniformity can be changed between different phases of the injection procedure. For example, liver enhancement can be changed during different phases of the imaging procedure to, for example, correspond to different portions of the liver in which peak enhancement time can vary because of variations in blood supply.

Another embodiment of the present invention for protocol determination or parameter generation in the case of a dual flow injection or simultaneous injection of an admixture of diluent/flushing fluid and contrast is discussed in connection with FIGS. 10 through 18. Once again, a primary goal of rational CT contrast protocol design is to develop injection protocols tailored to each patient considering, for example, the individual's hemodynamic state, the imaging region of interest, and the injection system constraints. The injection strategy can, for example, make use of the ability of the STELLANT® D injection system, available from Medrad, Inc. of Indianola, Pa., to provide simultaneous delivery (and thus dilution) of contrast media and saline. As described below, an additional phase of diluted contrast media allows for additional left heart enhancement, but with a reduced contrast agent (iodine) load to reduce or eliminate right heart artifacts.

Figure 10:
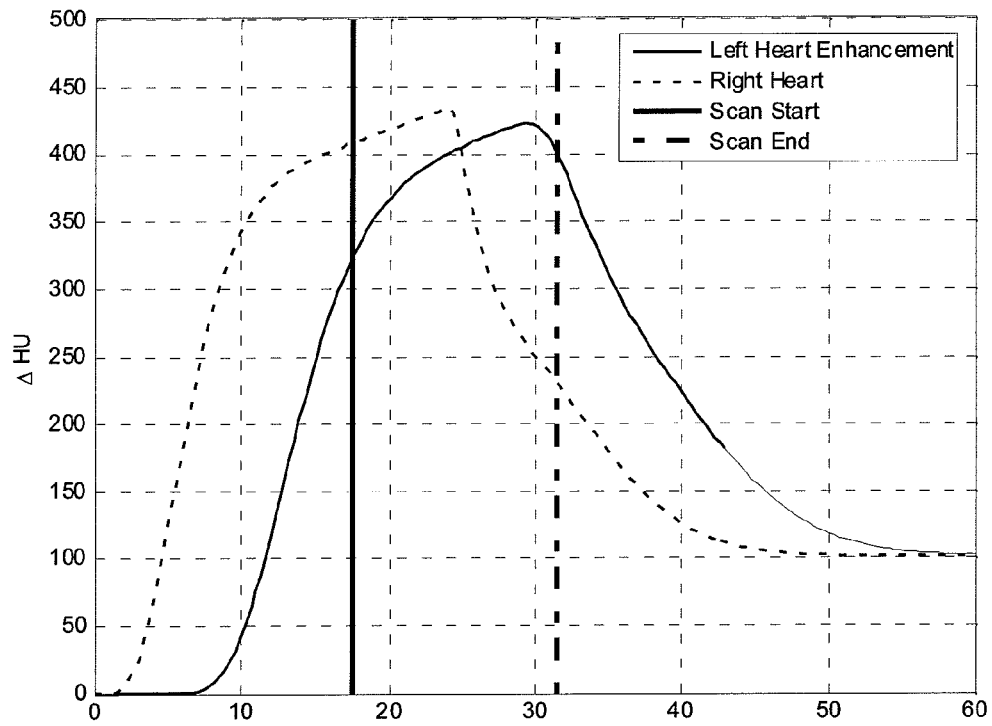
FIG. 10 illustrates a time enhancement curve resulting from a 120 ml uniphasic injection.
Figure 11:
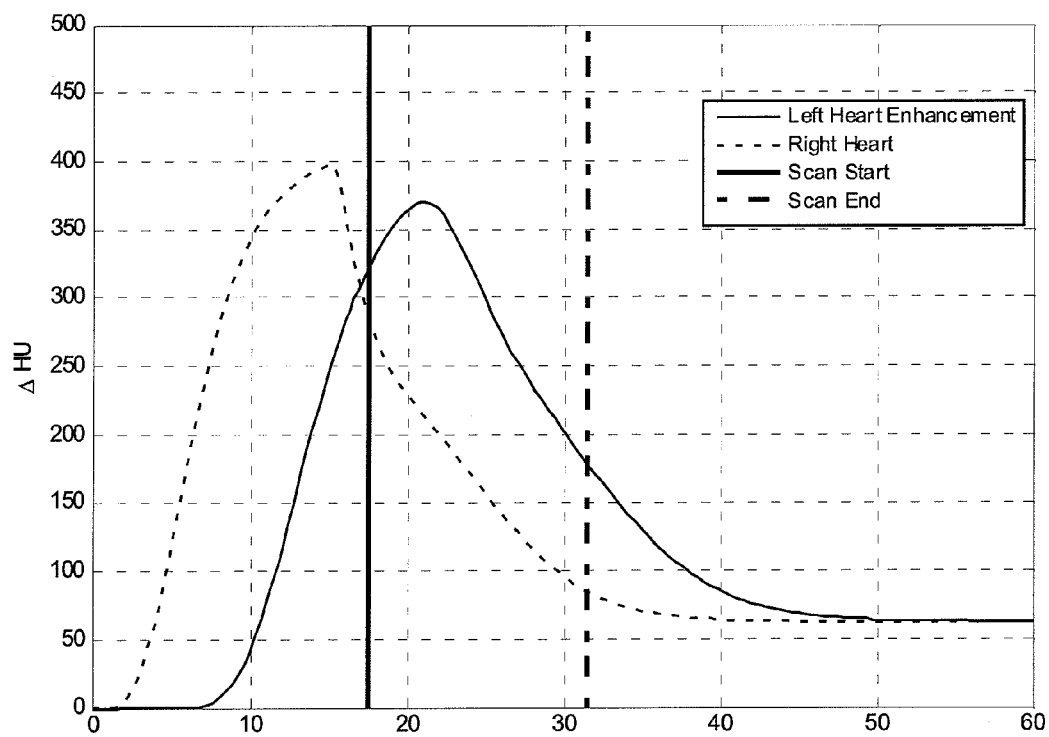
FIG. 11 illustrates a time enhancement curve resulting from a 75 ml contrast bolus followed with a 50 ml saline push or flush.

FIGS. 10 thorough 14 illustrated enhancement profiles (simulated as described above) for a 35 yr old, healthy male (200 lbs, 6 ft tall) injected with 370 mgI/ml contrast medium. Enhancement curves are presented for the right heart and the left heart compartments as predicted with the compartmental, pharmacokinetic model set forth in FIG. 7. FIG. 10 depicts enhancement with a 120 ml uniphasic injection, whereas FIG. 11 presents the enhancement resulting from a 75 ml bolus followed with a 50 ml saline push or flush. Whereas the enhancement of the left heart in FIG. 10 is above 300 Hounsfield Units (HU) throughout the scan duration, the right heart is enhanced brightly throughout the scan window, and is more likely to produce image artifacts.

Figure 12:
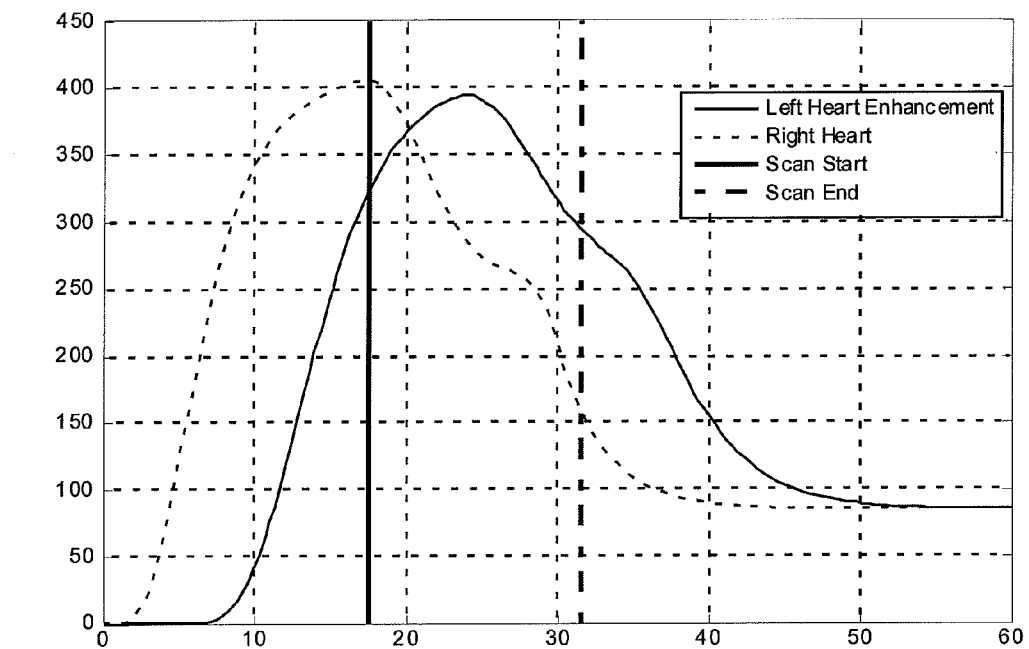
FIG. 12 illustrates simulated time enhancement curves resulting from injections performed with a 75 ml main bolus followed by a diluted phase of contrast of the same flow rate having a contrast/saline ratio of 50/50.
Figure 13:
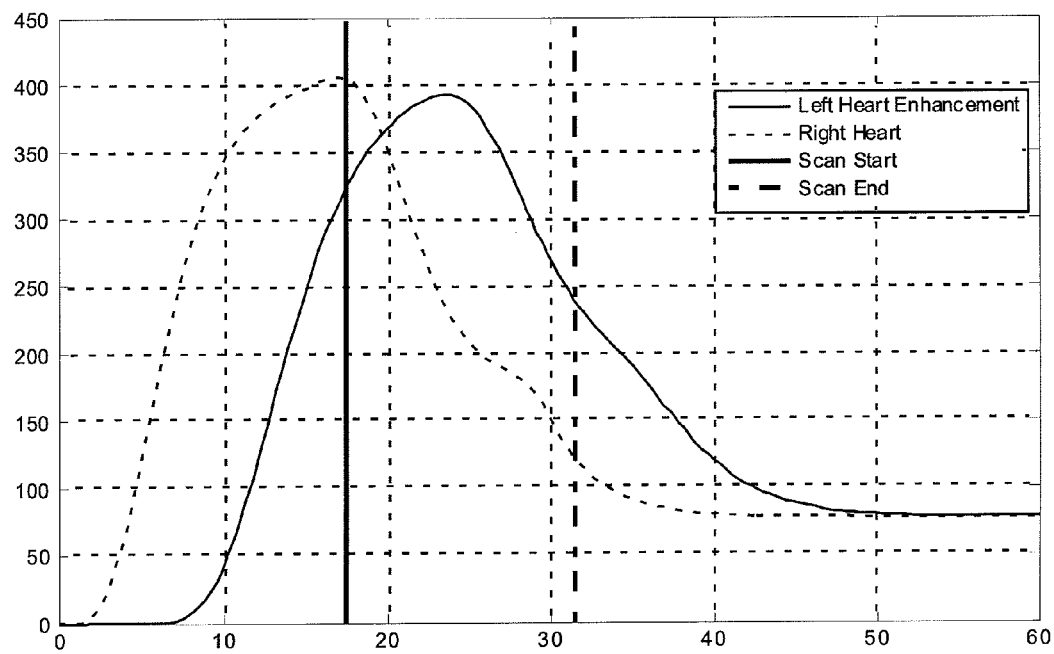
FIG. 13 illustrates simulated time enhancement curves resulting from injections performed with a 75 ml main bolus followed by a diluted phase of contrast of the same flow rate having a contrast/saline ratio of 30/70.
Figure 14:
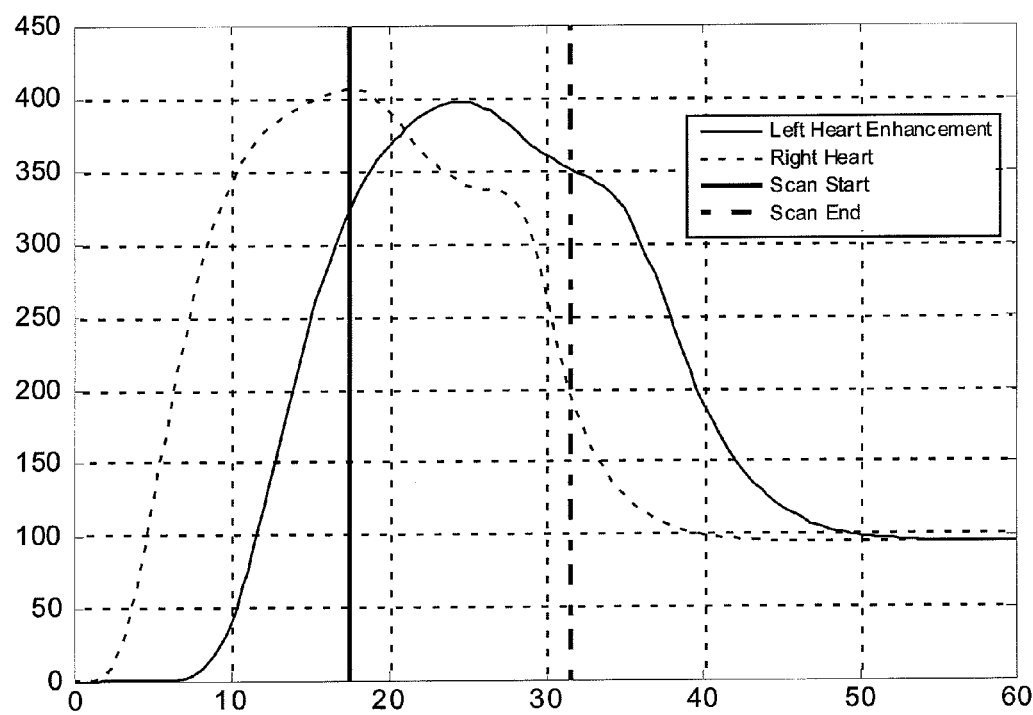
FIG. 14 illustrates simulated time enhancement curves resulting from injections performed with a 75 ml main bolus followed by a diluted phase of contrast of the same flow rate having a contrast/saline ratio of 70/30.

FIGS. 12-14 illustrate simulated time enhancement curves resulting from injections performed with a 75 ml main bolus followed by a diluted phase of contrast of the same flow rate in the following contrast/saline ratios: 50/50, 30/70, and 70/30, respectively. The enhancements of the left and right hearts were clearly modified by the additional phase of diluted contrast. The 70/30 phase (FIG. 14) provided good left heart enhancement, but the right heart enhancement may have been too great. The 30/70 ratio (FIG. 13) provided good right heart enhancement, but not enough left heart enhancement throughout the scan window. The 50/50 ratio (FIG. 12) provides the best trade-off, for this simulated patient, of right heart and left heart enhancement.

Figure 15:
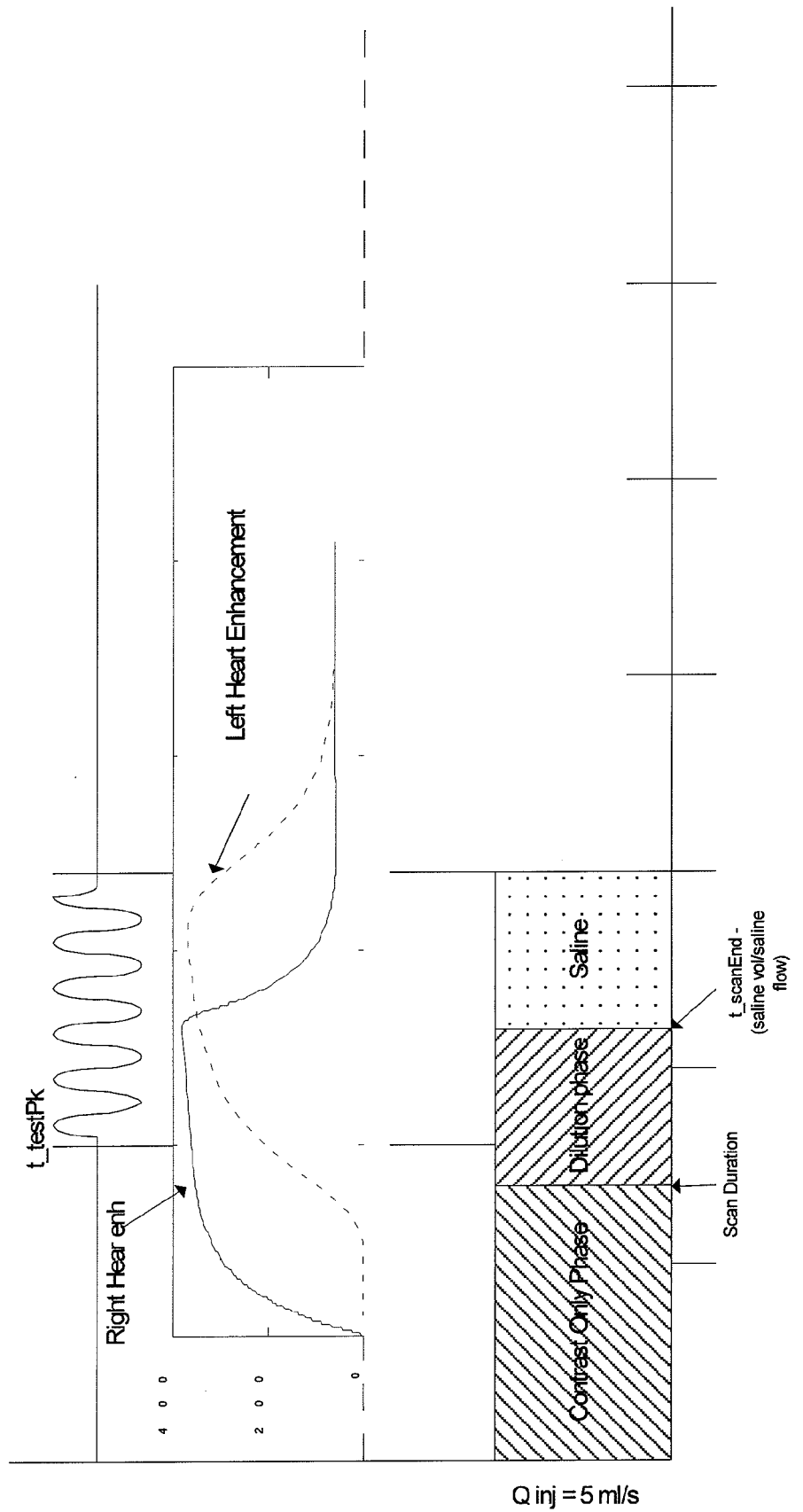
FIG. 15 illustrates an injection process of contrast material with a fixed, time axis wherein the bottom axis presents the contrast injection profile, the middle axis sets forth the enhancement profiles for left and right heart compartments, and the top axis sets forth the scanning duration.

FIG. 15 illustrates an injection process of contrast material with a fixed, time axis. The bottom axis presents the contrast injection profile (in this instance, a uniphasic injection at 5 ml/s), the middle axis sets forth the enhancement profiles for left and right heart compartments, and the top axis presents the scanning duration. The two vertical lines represent the start and completion times of the scan. In one embodiment, an algorithm of the present invention assumes that the clinician performs a small, test bolus injection of contrast (for example, a test injection of 20-25 ml of contrast at the same flow rate as the flow rate to be used during the diagnostic scan) followed by a saline push. A dynamic CT scan generates an enhancement curve from which the time to peak of the test bolus and the enhancement peak of the test bolus can be measured/recorded. It is also assumed that the scan duration is known before the test bolus and diagnostic injections begin.

In one embodiment, the first bolus of contrast is made equal in duration to the scan duration. The flow rate is given by the operator (assumed to be 5 ml/s in this study). The volume of the first phase, therefore, is the product of scan duration and flow rate. The determination of the volume of the second phase is made by considering the time to peak of the test injection, the duration of the first phase, and the end of the scan. The contrast injection should not last longer than the end of the scan. Because of the propagation delay of contrast from the injection site to the right atrium (about 5-8 seconds typically), contrast injection is stopped 5-8 seconds before the end of the scan so that the follow on contrast can fill the right heart. The approach taken in connection with the embodiment of FIG. 15 proscribed a saline flush of 40 ml at 5 ml/s, so the contrast injection of the dilution phase was ended 8 seconds before the end of the scan.

The volume of the second, diluted phase is then determined by:

$$Vol_2 = \left(\left(t_{scan\_end} - \frac{40\,\text{ml}}{5\,\text{ml/s}}\right) - duration_1\right) \cdot 5\,\text{ml/s}$$

The value $T_{scan\_end}$ is computed by consideration of the time to peak of the test bolus and the scan duration:

$$t_{scan\_end} = t_{test\_bolus\_peak} + duration_{scan}$$

Figures 16, 17:
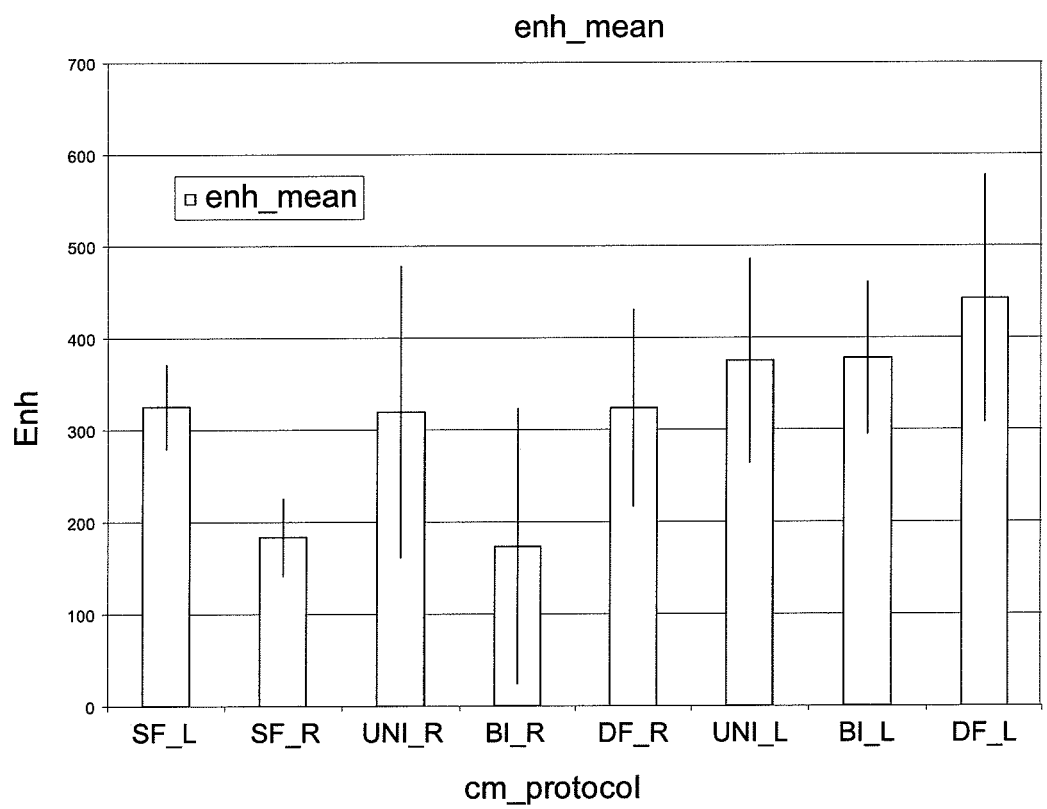
FIG. 16 illustrates a heuristic for determining contrast/saline ratio of an admixture or dual flow phase on the basis of peak enhancement of a test bolus.
FIG. 17 sets forth preliminary clinical data for uniphasic injections, biphasic injections and multiphasic, admixture injections of the present invention.

The ratio of the second phase is determined by a heuristic that maps peak enhancement of the test bolus to contrast/saline ratio as set forth in FIG. 16.

To limit the total amount of contrast delivered to each patient (in the event of an extremely long time to peak of the test enhancement), a maximum of 40 ml is made available for the dilution phase. If the computations above suggest a contrast volume greater than 40 ml., the system can limit the total contrast volume to 40 ml, compute the total volume in that phase (with the saline) considering the dilution ratio so as not to exceed 40 ml of contrast. The total contrast volume allowable in the dilution phase can also be set as a function of weight, estimated or measured cardiac output, Body Mass Index, or other physiometric indicator. Bioimpedance measurements have been developed to non-invasively measure cardiac output. The BIOZ® system available from CardioDynamics International Corporation of San Diego, Calif. can, for example, be used to measure a patient's cardiac output via impedance cardiography. Impedance cardiography (ICG), also known as thoracic electrical bioimpedance (TEB), is a technology that converts changes in thoracic impedance to changes in volume over time. In this manner, impedance cardiography is used to track volumetric changes such as those occurring during the cardiac cycle. Such measurements are gathered noninvasively and continuously. In general, an alternating current is transmitted through the chest. The current seeks the path of least resistance: the blood filled aorta. Baseline impedance to current is measured. Blood volume and velocity in the aorta change with each heartbeat. Corresponding changes in impedance are used with ECG to provide hemodynamic parameters. See Overview of Impedance Cardiography available at http://www.impedancecardiography.com/icgover10.html and www.cardiodynamics.com.

The threshold values in FIG. 16 were determined by analyzing clinical data from a sample of 50 test bolus injections and subsequent numerical modeling. Heuristically, the rule is designed to provide more contrast in patients with smaller peak enhancements (assuming that more contrast is needed for sufficient left and right heart enhancement) and less contrast to patients with strong test enhancements. Because the volume of agent is being tailored to patients with longer or shorter times to peak, and the total iodine load is adjusted based on test bolus enhancement, variability among patient enhancement should be reduced with this approach. FIG. 17 sets forth preliminary clinical data indicating this outcome. In FIG. 17, the first 2 bars are data generated with the algorithm just described for the left and right heart (SF_L and SF_R, respectively). The error bars indicate +/−1 standard deviation. The remaining data points are enhancement values generated with a uniphasic protocol of 120 ml of contrast (350 mgI/ml, no saline push; UNI_R and UNI_L), a biphasic protocol (75 ml of 350 mgI/ml with 40 ml of saline; BI_R and BI_L), and finally a dilution protocol with a fixed dilution ratio of 30/70 for all subjects (initial phase volume of 350 mgI/ml=scan duration*5 ml/s; DF_R and DF_L). The volume of the second phase was a fixed 50 ml of fluid. A saline flush of 40 ml followed.

Figure 18:
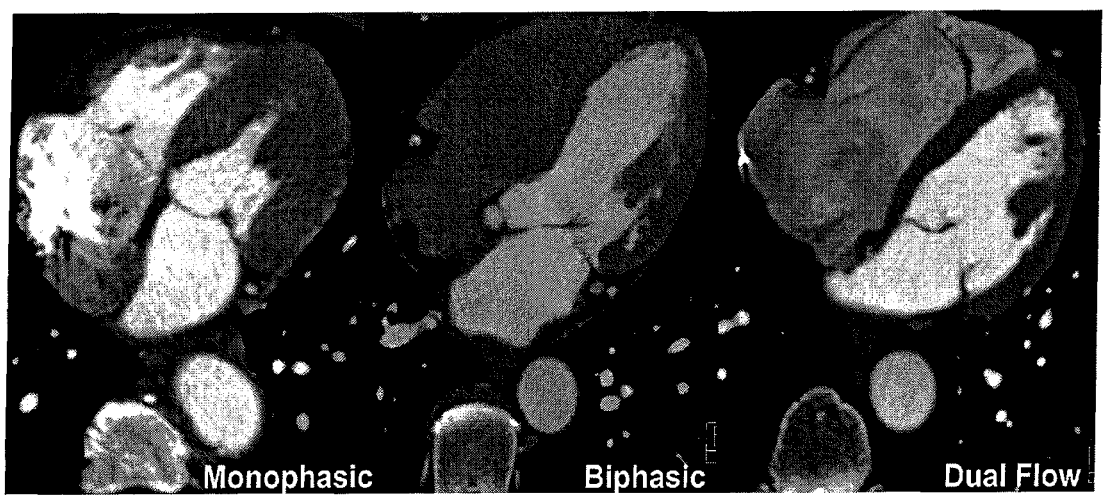
FIG. 18 illustrates several scan images of the left and right heart for a uniphasic injection, a biphasic injection and a multiphasic injection including a phase in which a contrast/saline admixture is injected.

FIG. 18 sets forth scan images for the left and right heart in the case of a uniphasic or monophasic injection protocol (contrast only, no saline flush), a biphasic protocol (contrast followed by a saline flush) and a dual flow injection protocol as described above (contrast, followed by a contrast/saline admixture, followed by a saline flush). As illustrated in FIG. 18, a dual flow injection procedure in which the injection protocols can be determined as described above can provide improved imaging procedures for the left and right heart.

Figure 19:
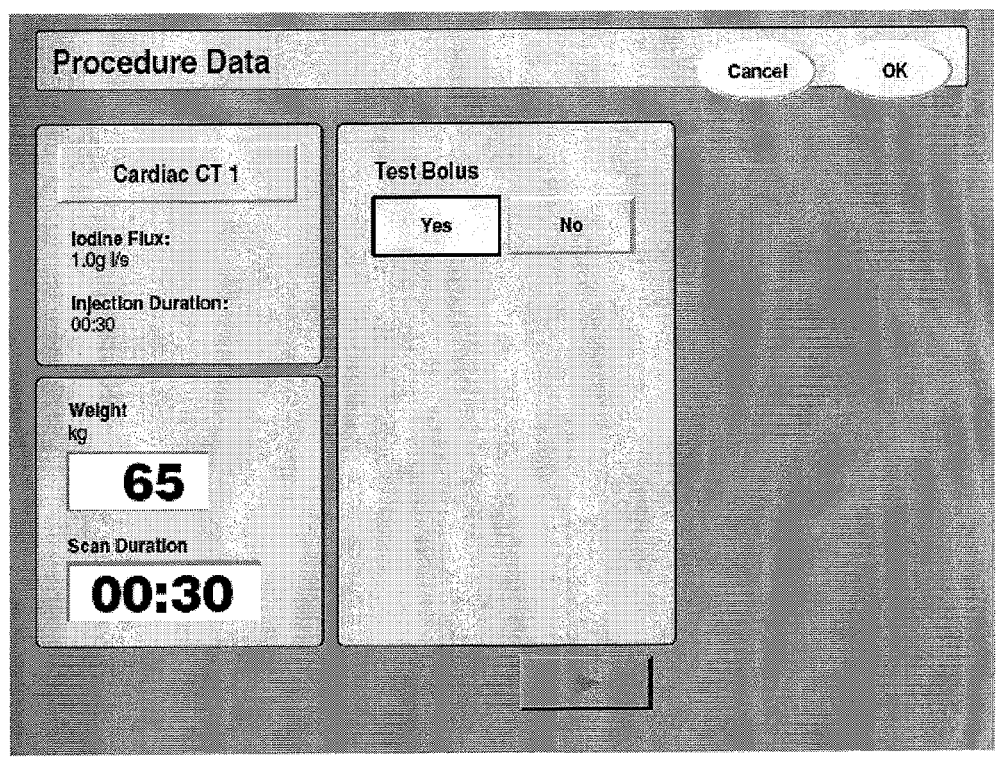
FIG. 19 illustrates an embodiment of a graphical user interface for use with an embodiment of a parameter generator of the present invention.
Figure 20:
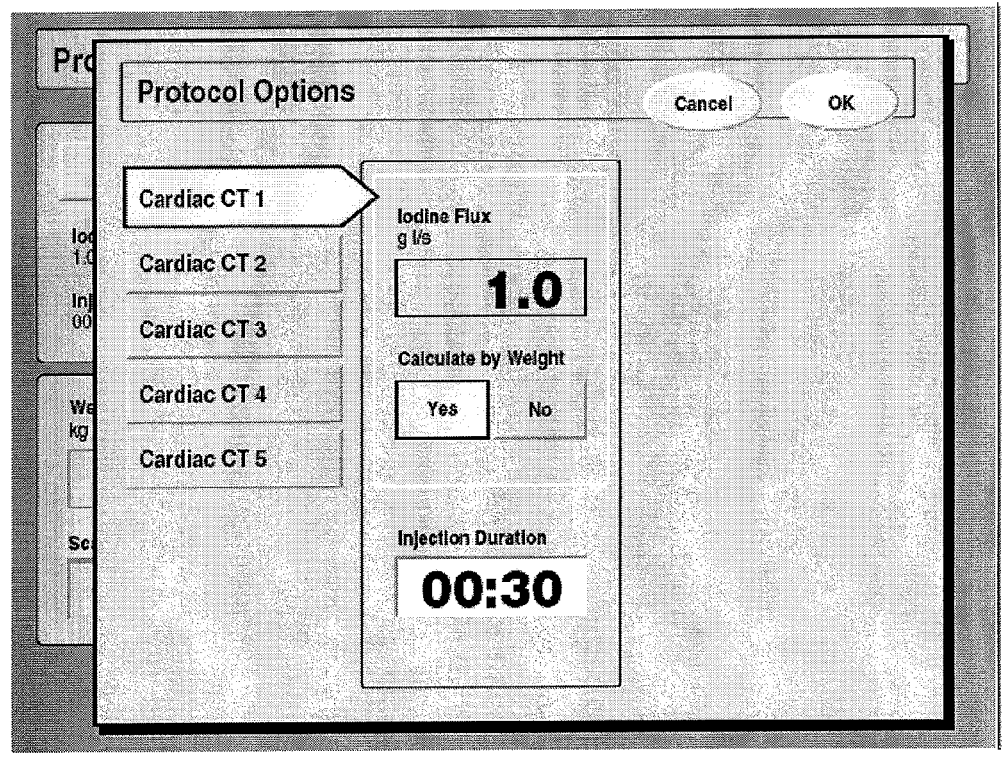
FIG. 20 illustrates another portion of a graphical user interface for use with an embodiment of a parameter generator of the present invention.

FIGS. 19 through 23 illustrate several screen captures of a graphical user interface suitable to effect the dual flow injection protocol determination described above. In FIGS. 19 and 20 the algorithm set forth above in connection with FIGS. 10 through 18 is selected via the designation Cardiac CT1. A patient weight of 65 kg and a test scan duration of 30 seconds are input. An iodine flux of 1.0 g/s is established for the imaging procedure injection. As the concentration of contrast fluid is 250 mgI/ml, a flow rate of 4 ml/s will be used in the imaging procedure injection.

Figure 21:
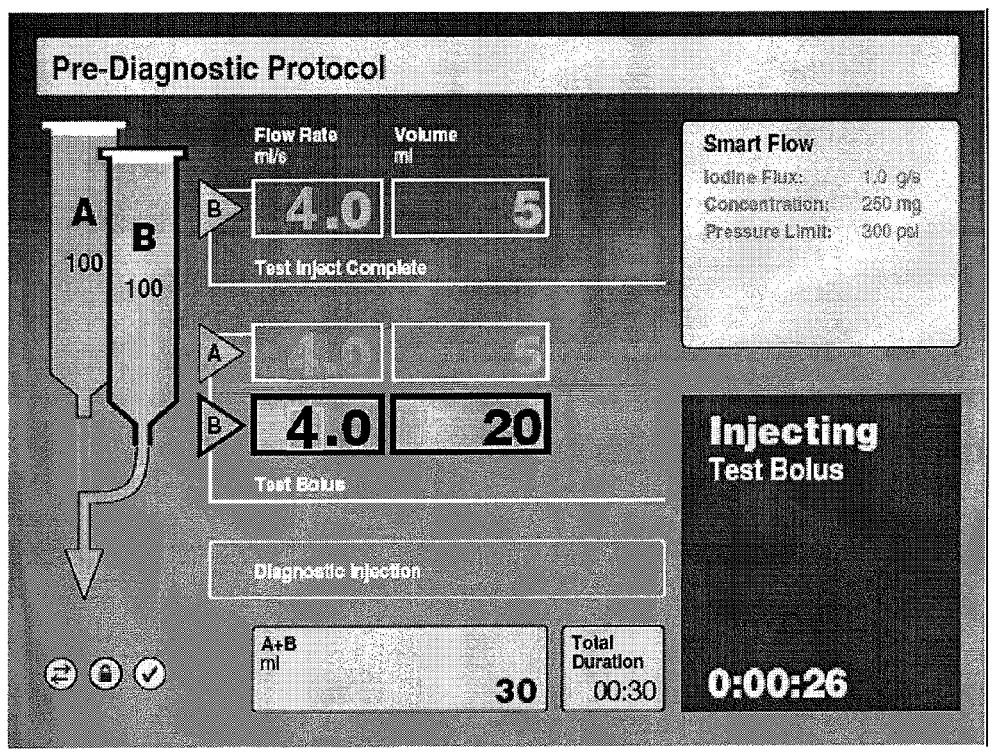
FIG. 21 illustrates another portion of a graphical user interface for use with an embodiment of a parameter generator of the present invention.
Figure 22:
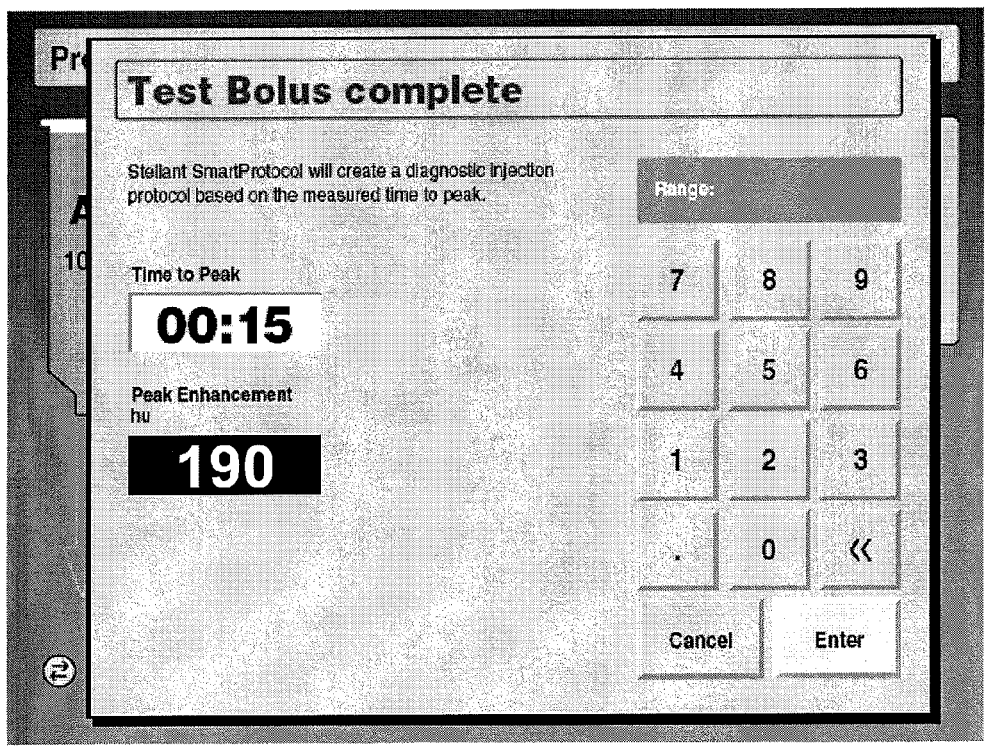
FIG. 22 illustrates another portion of a graphical user interface for use with an embodiment of a parameter generator of the present invention.
Figure 23:
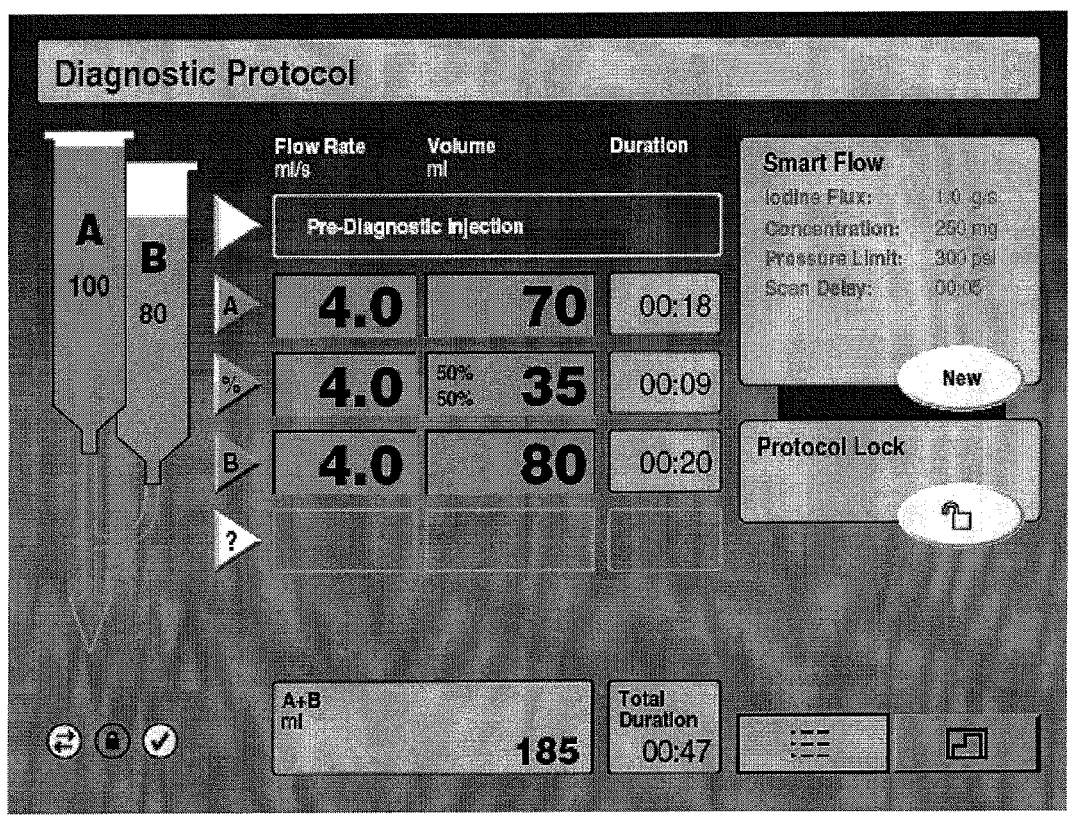
FIG. 23 illustrates another portion of a graphical user interface for use with an embodiment of a parameter generator of the present invention.
Figure 24A:
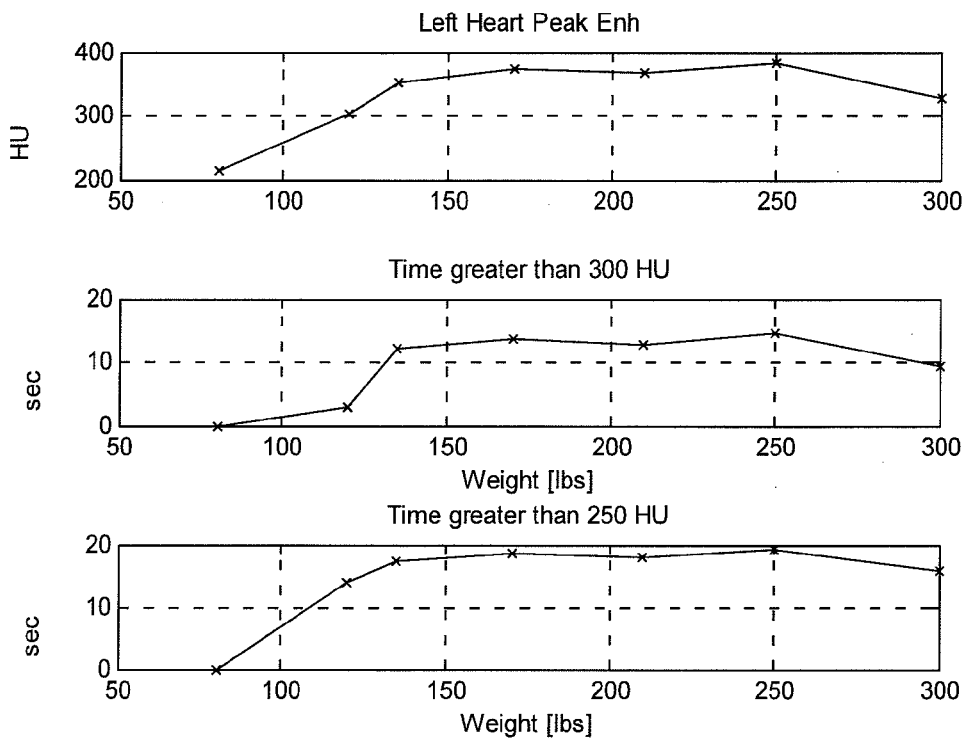
FIG. 24A illustrates PB PK simulation results using Table 1 weight factors set forth below with 370 mgI/ml contrast with a 6 ml/s flow rate limit (13 sec scan duration).
Figure 24B:
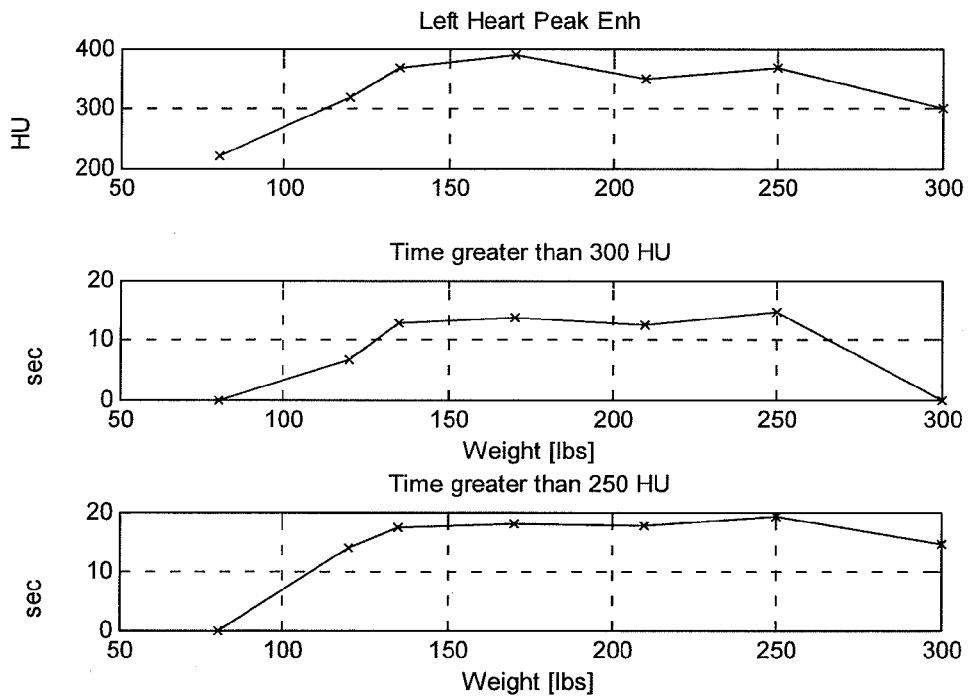
FIG. 24B illustrates PB PK simulation results using Table 1 weight factors set forth below with 320 mgI/ml contrast with a 6 ml/s flow rate limit (13 sec scan duration).
Figure 24C:
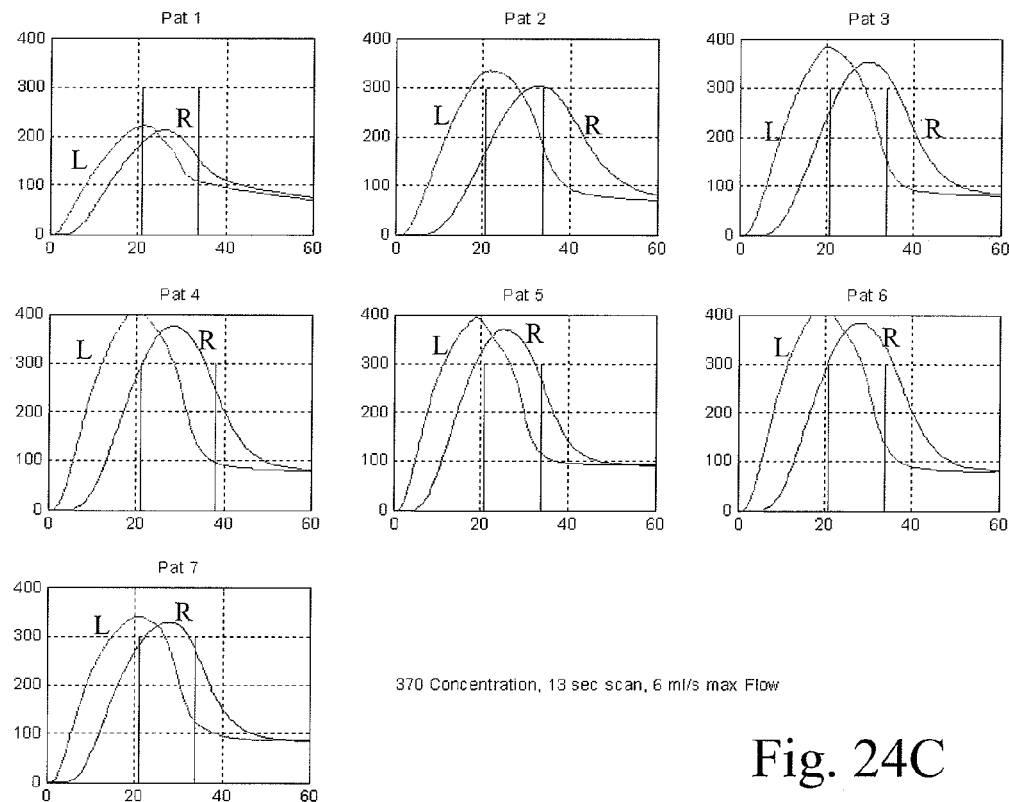
FIG. 24C illustrates enhancement profiles in left heart (L) and right heart (R) compartments generated via PB PK simulation results using Table 1 weight factors set forth below with 370 mgI/ml contrast and a 6 ml/s flow rate limit (12 sec scan duration), wherein the vertical lines indicate the scanning window as determined by the scan delay computation described within and a 13 second scan duration.
Figure 24D:
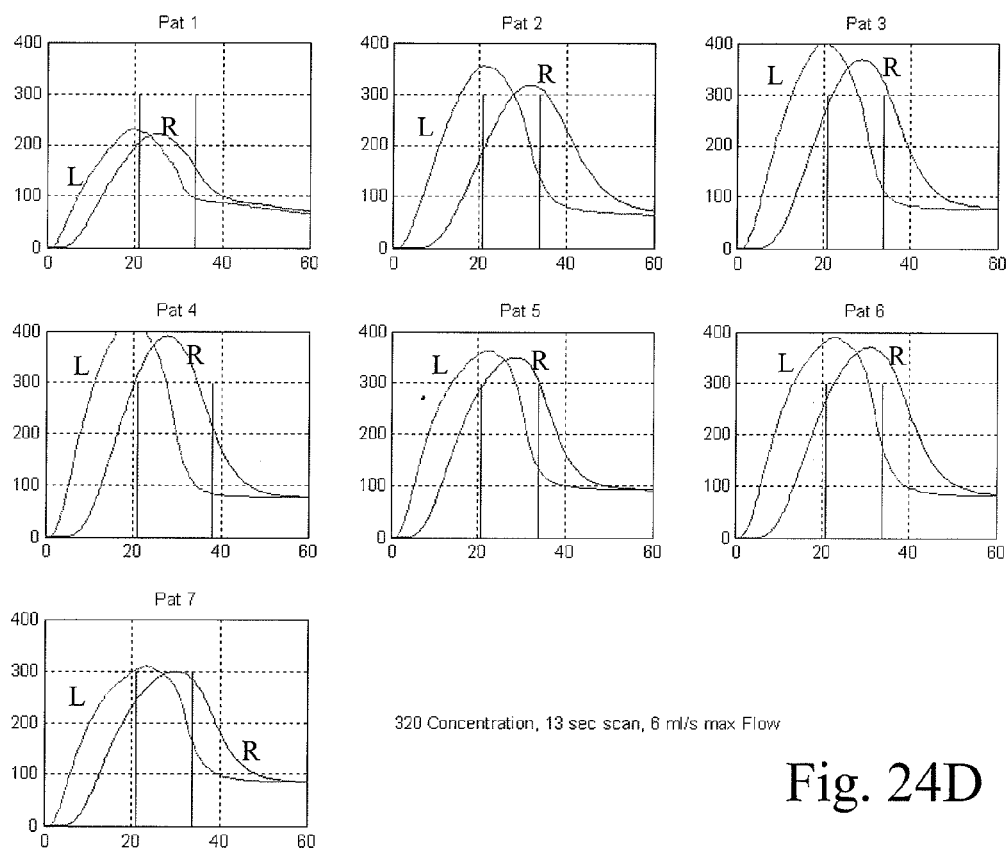
FIG. 24D illustrates enhancement profiles in left heart (L) and right heart (R) compartments generated via PB PK simulation results using Table 1 weight factors set forth below with 320 mgI/ml contrast and a 6 ml/s flow rate limit (12 sec scan duration), wherein vertical lines indicate the scanning window as determined by the scan delay computation described within and a 13 second scan duration.
Figure 25:
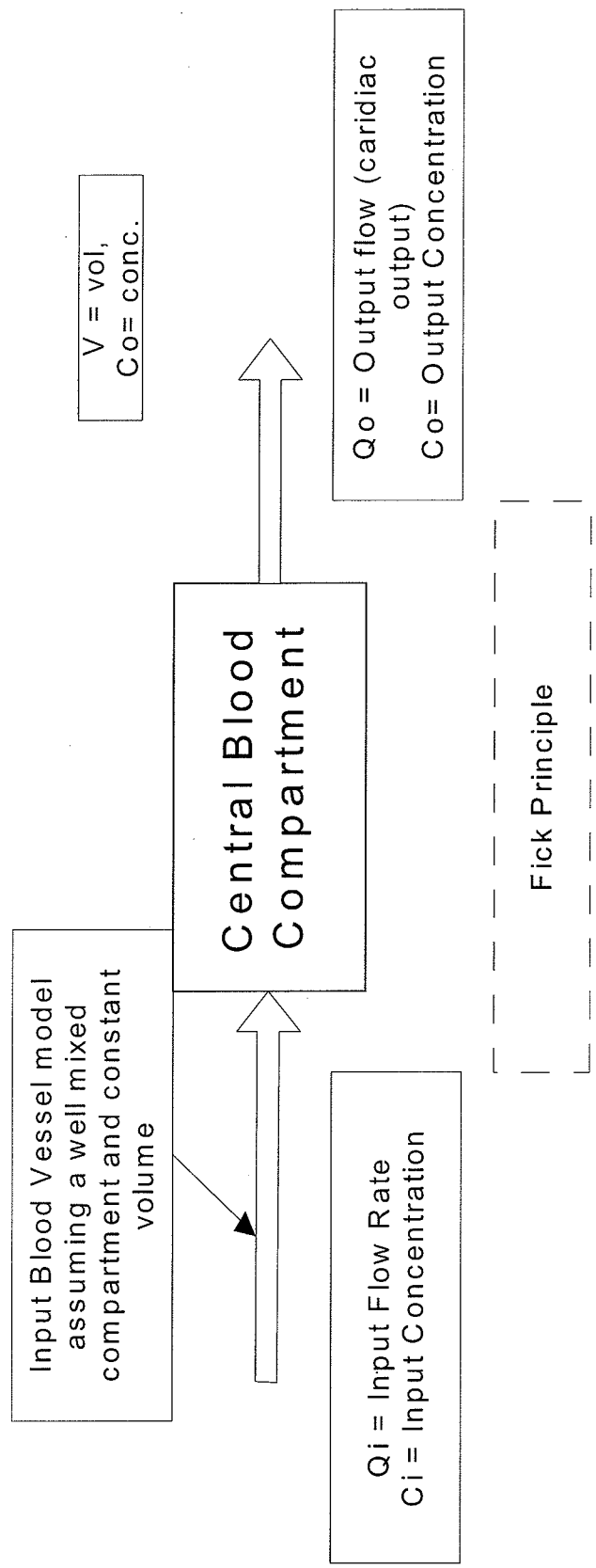
FIG. 25 illustrates Fick's principle.

As set forth in FIG. 21, the flow rate during the test injection is 1.0 ml/s. During the 30 second test injection, a bolus of saline (from source B) is first injected at a flow rate of 4.0 ml/s for 5 seconds. A bolus of contrast (from source A) is then injected at a flow rate of 4.0 ml/s for 5 seconds. Finally, a flushing bolus of saline is injected at a flow rate of 4.0 ml/s for 20 seconds. After the completion of the test bolus injection, the time to peak and the peak enhancement are determined as illustrated in FIG. 22. Using the values set forth above, the diagnostic injection protocol is determined using the system/method described in connection with FIGS. 10 through 18. FIG. 23 sets forth the determined diagnostic injection protocol including the following three phases: (1) injection of a 70 ml volume of contrast (source A) at 4 ml/s (duration of 18 seconds); (2) injection of a 35 ml volume of a 50/50 contrast/saline admixture (dual flow from sources A and B) at 4 ml/s (duration of 9 seconds); and (3) injection of an 80 ml volume of saline (source B) at 4 ml/s (duration 20 seconds). Thus, a total of 185 ml of fluid is injected over a time period (total duration) of 47 seconds. As also set forth in FIG. 23, a pressure limit of 300 psi for the fluid path used in the injection procedure was set. Also, a scan delay of 5 seconds was established.

Other embodiments of protocol generation or determination systems, devices and methods (sometimes referred to collectively as systems) of the present invention are described below. As described above, the protocol generation systems provide an injection protocol that is adapted or personalized for a specific patient. In several embodiments, an initial protocol, including parameters for one, two or more phases, is determined based upon available information (for example, one or more patient parameters such as weight, height, cardiac output, etc., concentration of an agent in the pharmaceutical to be delivered—for example, a contrast enhancing agent such as iodine—scan duration, etc.). This initial protocol can, for example, be used to determine a volume of pharmaceutical, a diluent (for example, saline), and/or other fluid to be delivered to the patient, which, in turn, can provide volumes of such fluids to be loaded into containers (for example, syringes) from which the fluid will be delivered. Several representative embodiments of injection of contrast using fillable syringes are set forth below to illustrate the present invention. In such procedures, a clinician must preload the syringe(s) with a volume of contrast prior to, for example, performing a test or identification bolus. It is impractical (at least with the current generation of injection systems) to expect the clinician to load or reload contrast into the syringe after the identification bolus has been performed. The protocol determination strategies of the present invention enable a priori determination of doses/volumes that the clinician then loads.

After determination of an initial protocol and loading of the syringe(s), an identification bolus or test bolus can be administered to the patient as described above. Once again, the identification or test bolus is a low volume injection of contrast. A single level scan can, for example, be performed in a region or territory of interest in, for example, the cardiac vasculature. The morphology of the resulting enhancement curve gives insight to the characteristics of the cardiovascular system and the dynamics of propagation of the agent of interest in the pharmaceutical (the contrast) in situ, from which tailored or adjusted injection protocols can be generated.

1.0 Design Description

In a representative embodiment, the primary data used to compute the volume of contrast to be delivered/loaded were the scan duration, one or more patient parameters such as the patient's weight, and contrast concentration.

A variable weighting factor (mg Iodine/Body weight kg) was used to determine the dose of Iodine for the patient. In general, there is a linear relation between the plasma concentration of Iodine and the enhancement (or CT Number) in Hounsfield Units in a blood vessel. Weight is easily obtained before the patient is scanned and serves as a practical means of computing the preload volume of contrast. The requirement to compute a preload volume can be eliminated through use of a continuous flow system using bulk containers of, for example, contrast and a flushing fluid or diluent (for example, saline) as described, for example, in U.S. Pat. Nos. 6,901,283, 6,731,971, 6,442,418, 6,306,117, 6,149,627, 5,885,216, 5,843,037, and 5,806,519, Published U.S. Patent Application No. 2006/0211989 (U.S. patent application Ser. No. 11/072, 999), and Published PCT International Patent Application No. WO/2006/096388 (PCT International Patent Application No. PCT/US2006/00703), the contents of which are incorporated herein by reference.

In several embodiments, the process software of the present invention discretizes the weight ranges of subjects in, for example, 7 ranges (for example, <40 kg, 40-59 kg, 60-74 kg, 75-94 kg, 95-109 kg, 110-125 kg, >125 kg). The loading coefficients or functions for the software, which depend upon and vary with patient weights, are displayed in Table 1 below. The coefficients or functions were derived by applying a multi-objective optimization routine (Gembicki's weighted goal attainment method (Gembicki, F. W., "*Vector Optimization for Control with Performance and Parameter Sensitivity Indices*," Case Western Reserve University (1974)) to simulated patients representing each of the weight ranges (using the physiologic based pharmacokinetic model set forth above in FIG. 7. As clear to one skilled in the art, the loading coefficients or functions can also be determined using a formula. In the multi-objective optimization, a representative goal was set to attain at least 350 HU peak enhancement in the Descending Aorta compartment of the physiologic PK model and attain enhancement greater than 300 HU for at least the duration of the scan. Rather than simulating and optimize all combinations of contrast concentration and scan durations, a representative optimization was performed with 370 mgI/ml contrast concentration and a 13 second scan duration—typical for cardiovascular CTA. The values reported in Table 1 were modified slightly from those generated in the optimization to accommodate other concentrations using simulation and applying engineering judgment. The results of the simulations are set forth in FIGS. 24A through 24G. The goals set forth above are not explicitly recognized in the two lightest cases, which were allowed as a result of a desire to restrict contrast volume to smaller patients (most likely pediatric patients).

TABLE 1

| Weight Range In kg | Syringe Permitted (200, 150, 100) | Weight Value In kg | Weight Factor In mg of Iodine/kg patient weight |
|---|---|---|---|
| <40 | 200, 150, 100 | 40 | 0.45 |
| 40-59 | 200, 150, 100 | 50 | 0.40 |
| 60-74 | 200, 150, 100 | 67 | 0.375 |
| 75-94 | 200, 150, 100 | 85 | 0.367 |
| 95-109 | 200, 150 | 102 | 0.35 |
| 110-125 | 200 | 118 | 0.31 |
| >125 | 200 | 125 | 0.30 |

In several embodiments, published results of previous studies were used to provide the boundary conditions for the dosing scale of the software of the present invention. Previous studied indicate that a fixed injection duration (and a flow rate computed to achieve a weighted dose of plasma Iodine) produces enhancement values (across a sample) and time to aortic peak independent of patient habitus. Published pharmacokinetic analysis of contrast dynamics also leads to the same conclusion. In several embodiments, the injection duration in the software of the present invention was fixed (for a patient) based on the scan duration if the computed flow rate was not greater than a clinically realizable value (as determined by the clinician).

Common current clinical practice calls for CTA injection protocols with durations equal to the scan duration. This practice may achieve suboptimal results in most cases because of non-deterministic delays in the scanner's activation. A conservative approach to protocol design (to prevent "missing" the bolus) while recognizing that contrast disperses in the vessels is then to inject contrast with duration longer than the scan duration. In several embodiments, the protocol determination software of the present invention used a rule that the inject duration (for a patient) is the scan duration plus 4 seconds, unless the scan is less than 16 seconds, for which a minimum injection duration of 16 seconds is proscribed.

Previous studies have demonstrated the linear time invariant properties of contrast medium propagation and enhancement. Analyses and experiments reported in the radiological literature demonstrate that the Iodine flux rate [mg I/s]I into the patient has a linear relationship to peak Iodine plasma concentration (and subsequently contrast enhancement). Current practice mandates a high plasma concentration (and enhancement value) of Iodine for robust coronary artery CTA (>=400 HU). Therefore, a high Iodine input flux is desired. The input flux should be constrained, however, with the realization that contrast injection rates typically don't exceed 6-7 ml/s. Current cardiac 64 MSCT (Multislice CT) scan durations range from 10-20 seconds.

Recognizing that the Iodine delivery flux is computed by multiplication of the contrast concentration [mgI/ml] by the administration flow rate [ml/s], one skilled in the art appreciates that, to achieve a high input flux, either the concentration or the flow rate should increase. Simple pharmacokinetic theory and Fick's principle (see FIG. 25) demonstrate this idea explicitly. For the sake of appreciating CTA enhancement, one can make a conceptual model of the enhancement mechanism by describing a volumetric flow rate input ($Q_i$) into a well mixed compartment with a concentration of agent ($C_i$). The volumetric flow rate of blood into which the agent is introduced is $Q_o$ (the cardiac output for a physiological system). The governing differential equation for this situation is given in Equation 1 below. A graphical depiction of the single compartment flow model is also depicted below. The solution of the differential equation for t<tend gives an insight to the interplay of injection rate, cardiac output, and input concentration of the species being introduced.

$$V \frac{dC_o}{dt} = Q(C_i - C_o) \quad \text{Equation 1}$$

$$C_o(t) = \begin{cases} \frac{Q_i}{Q_o} C_i \left(1 - e^{-\frac{Q_0}{V}t}\right) & t \le injectDuration \\ C_o(injectDuration) e^{-\frac{Q_o}{V}t} & t > injectDuration \end{cases} \quad \text{Equation 2}$$

Equation 2 assumes that an input function of concentration in time extends from 0 to injectDuration seconds (a step function). Analysis of the solution in Equation 2 demonstrates that as $Q_i$ or $C_i$ increases, the concentration in the well-mixed central blood compartment increases (recall that the enhancement level in CTA is directly proportional to plasma concentration of the contrast agent (1 mgI/ml=25 HU at 120 kVP)). Also note that as the cardiac output ($Q_o$) increases, the plasma concentration and thus the enhancement level decreases (which agrees with previous empirical porcine work and findings in humans).

Using the weighting scale proposed in Table 1 (most convenient for preloading the syringe before the procedure) and recognizing that 7 ml/s is a practical limit for injection rates and imposing a minimum administration rate of 1 gI/s input flux for the lowest weight class (<40 kg), a minimum injection duration of 16 seconds provides a good trade-off between minimizing flow rate while maximizing Iodine flux rate [mg I/s]. Pharmacokinetic modeling and previous studies suggest that an Iodine administration rate of 1.75 gI/s for a 75 kg person is ideal for cardiac CTA. Ideally, the contrast protocol flow rate would be determined by asserting a gI/kg/s computation. However, access to scan duration at syringe load time cannot be guaranteed. The goal of achieving 1.75 gI/s (for a 75 kg patient with 370 contrast), though, is realized with the loading factors and injection duration rules presented herein. Above scan durations of 16 seconds, the scan duration plus 4 seconds is the rule to compute the injection duration per patient (plus 6 for patients >102 kg) to ensure the injection lasts longer than the scan.

As described above, a number of commercially available injectors offer the ability to simultaneously inject an admixture of contrast and a flushing fluid or diluent such as saline, thereby diluting the Iodine concentration of contrast entering the patient. This approach has value for reducing the incidence of streaking artifact pronounced in cardiac MSCT scans caused by less dilute contrast media flooding the Superior Vena Cava (SVC) and right heart while diluted (by the central blood volume) contrast previously injected is circulating through the coronary circulation (and left heart). By reducing the Iodine concentration during the injection, reductions in streak artifact and more consistent opacification of the right heart is possible. In general, current implementations of the dilution technology on, for example, the STELLANT® injector system available from Medrad Inc. of Indianola, Pa., prompt the clinician to enter a ratio of contrast to saline for delivery in injection phases. The clinician must apply judiciousness in selecting the "proper" ratio for the patient. In several embodiments, the software embodying the protocol determination strategy of the present invention attempts to rationalize the ratio of contrast to saline by choosing a ratio based on the morphology of the identification (test) bolus enhancement, the diagnostic injection duration, scan delay, and scan duration. In that regard, patients with higher test enhancement peaks should require more diluted contrast whereas those with less test bolus enhancement require less diluted contrast.

2.0 Protocol Generation Implementation

Figure 27A:
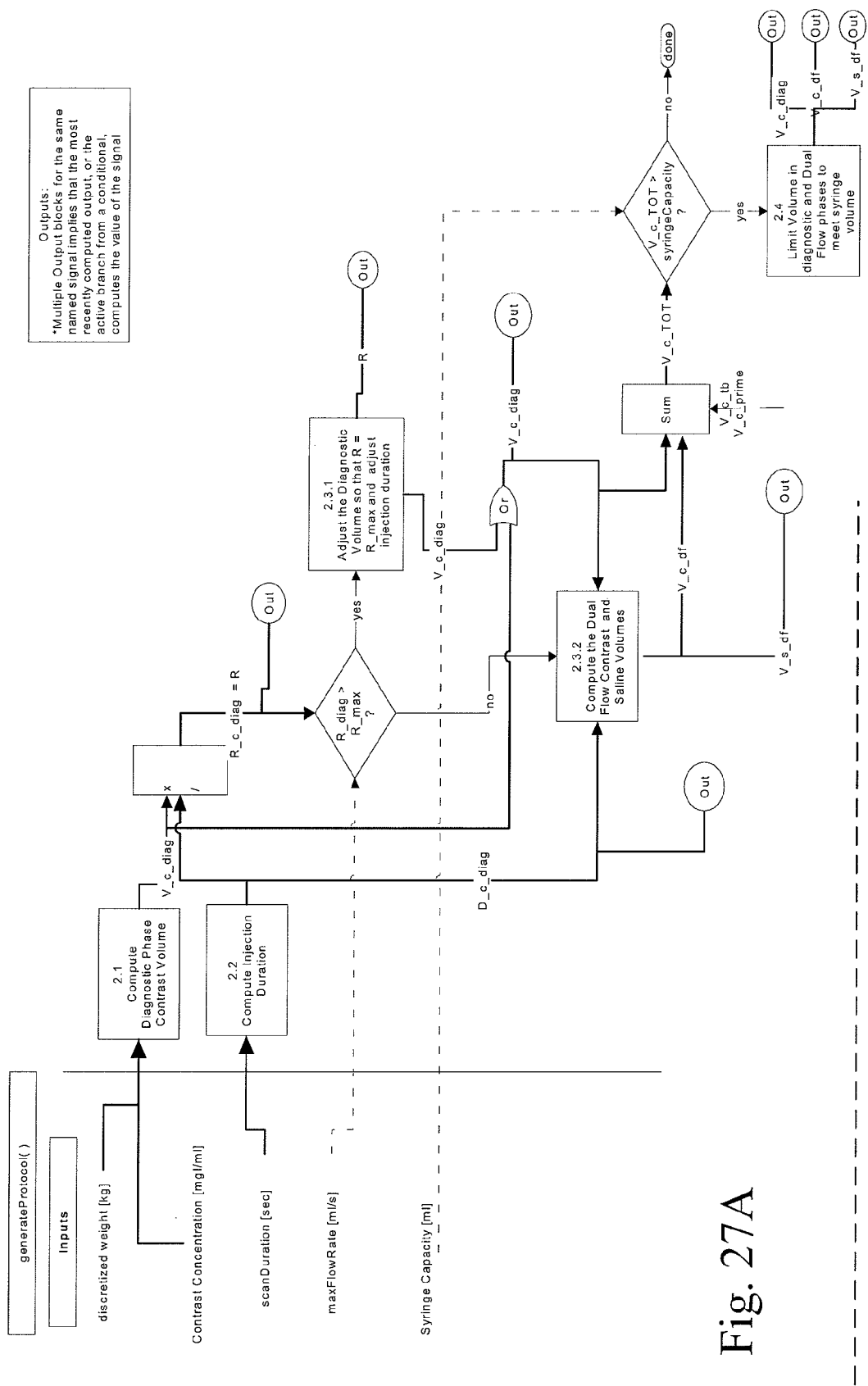
FIG. 27A illustrates a flowchart for an embodiment of a protocol generation process of the present invention.
Figure 27B:
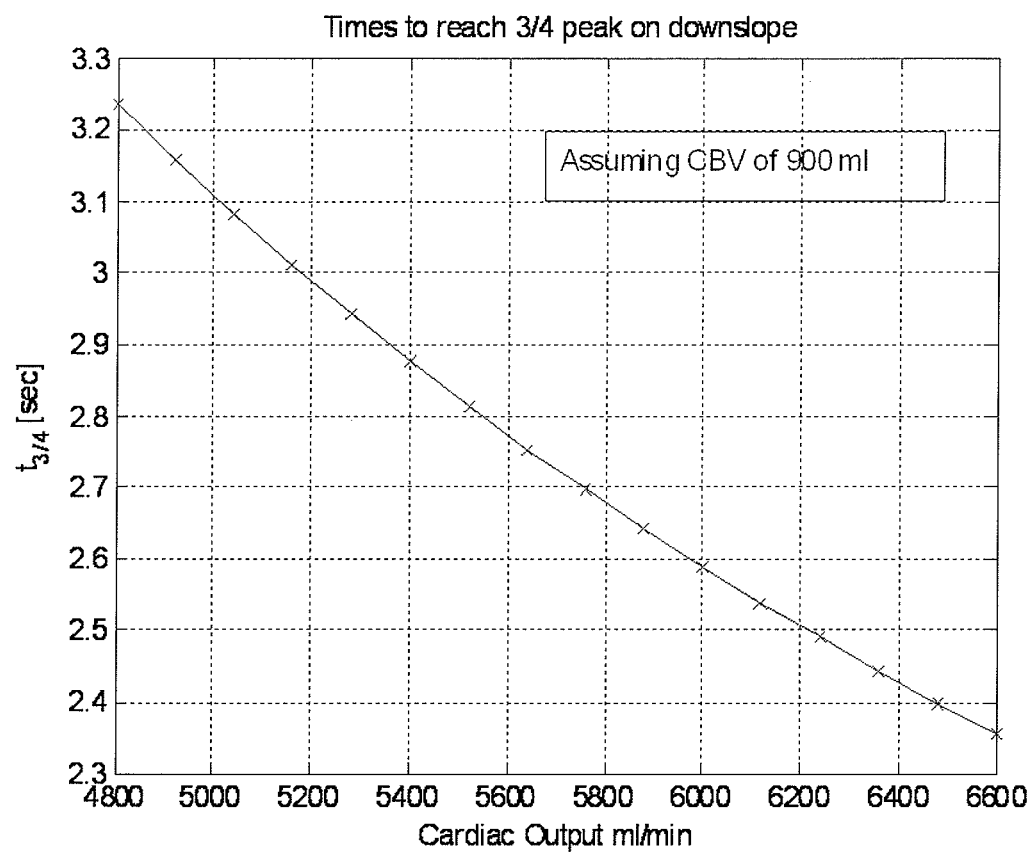
FIG. 27B illustrates a graph of Time to reach ¾ peak on the downslope of a time enhancement curve as a function of cardiac output.

An embodiment of a clinical workflow of the present invention is illustrated in FIG. 27A. As clear to one skilled in the art, data transfers between, for example, a scanner and an injector can occur via an electronic communication link and/ or via user input. In several studies, the protocol required a test bolus, required the use of, for example, a 200 ml syringe and used a diluted contrast or admixture phase for each patient. Calculations set forth herein use the following nomenclature for describing the various phases of the protocol Rate is designated by "R";
Volume is designated by "V"; and
Duration is designated by "D".

Subscripts indicate the type of media injected, where "C" is for contrast, "S" is for Saline and "T" is for total for a dual flow or admixture ratio. Superscripts indicate the portion of the protocol. The superscript "TI" stands for test injection; "TB" stands for test bolus; "Diag" stands for the first phase diagnostic portion of the protocol; "DF" stands for the dual flow phase; and "Flush" stands for the last saline phase. For example, the following symbol represents the flow rate of the admixture, dual flow or ratio phase of the diagnostic portion of the protocol.

$$R_T^{DF}=4\ ml$$

The following subsections are elaborations on the correspondingly numbered operations described in FIG. 27A.

2.1 Computation of Diagnostic Volume

The computation of the volume to be loaded uses the patient weight to determine the first phase and dual flow contrast volume based on the weight factor. The weight algorithm discretizes the weight range for clinical implementation ease. Table 1 sets forth the weight buckets, the values to use for each weight bucket and the weight factor. Alternatively, an algorithmic relationship can be set forth.

The volume calculations are based on the weight of the patient, the contrast concentration and the options used for the calculation. The weight factor is used for all patient based dosing calculations for the selected buckets. All weight calculations are in kilograms or kgs hereafter unless specifically indicated otherwise.

$$V_C^{Diag}=\text{weight}\times\text{weightfactor}\times 1000/\text{concentration} \qquad \text{Equation 3}$$

2.2 Computation of Injection Duration

A number of studies indicate that important control parameters for sufficient, first-pass CTA enhancement include Iodine mass-flux rate (mgI/s) and the duration of the injection. In several embodiments, the systems and methods of the present invention therefore personalize the dosage of contrast by manipulating the Iodine flux and injection duration. The volume of contrast is a dependent parameter. The scan duration is computed by the scanner on a per patient basis dependent on scanning and physiological parameters—for example, slice width, pitch, spatial resolution, region of interest, and heart rate. Ideally the operator has access to this data before the contrast can be loaded into the syringe, but accommodation is made in the present invention for cases in which such data is not available a priori. Ideally the injection duration would be equivalent to the scan duration. Because of diffusion, dispersion and scanning timing inaccuracies, a "safety" factor is typically needed to provide extra contrast.

The calculated injection duration of the first contrast phase is based on the scan duration with a minimal duration. Sixteen seconds provides a sufficient bolus width to account for timing inaccuracies in, for example, MSCT systems (with or without bolus tracking software). If a guaranteed, deterministic timing mechanism existed or if the whole timing bolus enhancement curve was available, this injection duration could theoretically be decreased to the scan duration (or shorter). The systems and methods of the present invention also support the use of an identification (that is, timing) bolus in addition to using bolus tracking software as known in the art for determining scan triggering times. The contrast bolus is lengthened, then, to 16 seconds for scans less than 12 seconds and a fixed duration factor "X" is added for longer scans.

$$D_C^{Diag}=\text{maximum}(16, \text{scan duration}+X) \text{ if scan duration}>=20\ \text{sec}\ D_C^{Diag}=\text{scan duration end} \qquad \text{Equation 4}$$

A simple pharmacokinetic analysis as described above can lend insight and rationale for choosing the "X" factor of Equation 4. Upon the completion of the input function (injectDuration in Equation 2), the decay of plasma concentration follows a first-order decay.

A typical cardiac output for a human is 5 L/min, and an average Central Blood Volume (the volume between the injection site and vascular territory of interest) is 900 ml. Using these parameters in Equation 2, one can solve for the ½ time constant and ¾ time constants. These times give insight to how much the plasma concentration is decreasing post maximal contrast enhancement in the vascular territory of interest. Equation 5 sets forth the calculations to determine the ½ and ¾ time constants. Given the standard Central Blood Volume, one can vary the cardiac output over the typical physiologic realm and find the corresponding ½ or ¾ time constant value as illustrated for $t_{3/4}$ in FIG. 27B.

$$t_{1/2}=\ln(.5)\cdot-\frac{V_{CBV}}{Q_{CO}} \qquad \text{Equation 5}$$

$$t_{3/4}=\ln(.75)\cdot-\frac{V_{CBV}}{Q_{CO}}$$

Four seconds provides an additional "safety" factor (the time to ¾ enhancement is greater than even that computed for a cardiac output of 4800 ml/min) for all cardiac outputs for achieving ¾ peak enhancement during the "tail" of contrast enhancement in the vascular region.

2.3 Computation and Limiting of Flow Rate

The flow rate is the combination of the volume and the duration. The calculation for the flow rate for the first or contrast only phase contrast is:

$$R_C^{Diag}=V_C^{Diag}/D_C^{Diag} \qquad \text{Equation 6}$$

$$R_{Total}^{DF}=R_C^{Diag} \qquad \text{Equation 7}$$

$$R_C^{TB}=R_S^{TB}=R_C^{Diag} \qquad \text{Equation 8}$$

The volumetric flow rate computed by Equation 6 is applied to all phases of the protocol (timing bolus, saline flush, dual flow, etc.).

2.3.1 Flow Rate Limiting

A site may choose to limit the maximum flow rate to a patient, or to all patients. Such an option can, for example, be a system configuration option. To deliver the maximum volume of the preloaded contrast, the duration of the first phase can, for example, be allowed to extend in time but only to a preset time (for example, 22 seconds). Additional contrast volume at the clamped flow rate will not be delivered. The clamping of the injection duration at 22 seconds is a result of the average time to peak of a 20 ml test bolus injections being 18 seconds and that the rules described in several embodiments mandate that heavier weight subjects have a scan delay of time to peak plus 6 seconds. The sum of 18 and 6 is 24 which is 2 seconds longer than the injection, allowing the benefit of the diluted phase to hopefully reduce artifact. Furthermore, previous studies have produced favorable aortic enhancement of >300 HU for a fixed injection duration protocol of 25 seconds with an older generation MSCT scanner. The following rule can be applied for situations when the computed flow rate exceeds the maximum set by the clinician:

$$R_C^{Diag} = R_{max}[\text{ml/s}]$$

$$\text{if } \frac{V_c^{Diag}}{R_C^{Diag}} \geq 22\text{sec } \& \text{ scanDuration} \leq 22 \text{ sec}$$

$$V_c^{Diag} = R_C^{Diag} \cdot 22$$

else $$V_c^{Diag} = V_c^{Diag}$$

Equation 9

Performing the steps in Equation 9 ensures that the contrast injection duration is fixed. This operation enforces the condition of a fixed contrast injection duration for all subjects having scans of n seconds. This is in keeping with results of a number of studies that have shown that to afford higher aortic enhancement, an increase in the injection rate must occur. If the clinician chooses to limit the injection flow rate, one can attain a higher plasma concentration if a very long injection at the limited flow rate (thus a larger volume of contrast) is performed to allow the recirculation of contrast to accumulate in the blood compartment (also to replace the blood diffusing into the extravascular compartment). This result is not desirable for angiographic applications, however, because of venous contamination and the asymmetric peak enhancement in the blood vessel compartment of interest. Table 2A below sets forth contrast load volumes without flow rate limiting, while Table 2B sets forth contrast load volumes with flow rate limiting (for a maximum flow rate of 5 ml/s) for the case that the injection duration is clamped at 22 seconds.

TABLE 2A

| Weight [kg] | Weight [lb] | Contrast Concentration [mgI/ml] | | | | | |
|---|---|---|---|---|---|---|---|
| | | 240 | 270 | 300 | 320 | 350 | 370 |
| <40 | <88 | 83 | 74 | 67 | 63 | 57 | 54 |
| 40-59 | 88-130 | 104 | 93 | 83 | 78 | 71 | 68 |
| 60-74 | 131-163 | 113 | 99 | 89 | 84 | 77 | 72 |
| 75-94 | 164-207 | 133 | 118 | 106 | 100 | 91 | 86 |
| 95-109 | 208-240 | 149 | 132 | 119 | 112 | 102 | 96 |
| 110-125 | 241-275 | 152 | 135 | 122 | 114 | 105 | 99 |
| >125 | >275 | 156 | 139 | 125 | 117 | 107 | 101 |

TABLE 2B

| Weight [kg] | Weight [lb] | Contrast Concentration [mgI/ml] | | | | | |
|---|---|---|---|---|---|---|---|
| | | 240 | 270 | 300 | 320 | 350 | 370 |
| <40 | <88 | 83 | 74 | 67 | 63 | 57 | 54 |
| 40-59 | 88-130 | 104 | 93 | 83 | 78 | 71 | 68 |
| 60-74 | 131-163 | 110 | 99 | 89 | 84 | 77 | 72 |
| 75-94 | 164-207 | 110 | 110 | 106 | 100 | 91 | 86 |
| 95-109 | 208-240 | 110 | 110 | 110 | 110 | 102 | 96 |
| 110-125 | 241-275 | 110 | 110 | 110 | 110 | 105 | 99 |
| >125 | >275 | 110 | 110 | 110 | 110 | 107 | 101 |

2.3.2 Computation of Dual Flow Contrast and Saline Volume

Dual flow or admixture flow is an optional part of the diagnostic protocol. The goal for certain cardiac procedures is to fully opacify the ascending aorta and the coronary arteries while partially opacifying the right heart. This is a difficult timing situation where one wants the contrast bolus to be in the coronaries while the ratio bolus is in the right heart. Therefore, one needs to determine the time to switch from full contrast to a ratio of contrast and saline. Hereinafter, all parameters with the designation "^" are new parameters after the dual flow adjustment has been made.

The total injection rate for the dual flow phase is the same as the first phase rate as indicated in Equation 7. The dual flow contrast volume is set at the time of protocol generation and is based on the weight of the patient. The following relation provides the dual flow contrast load volume:

$$V_C^{DF} = 0.20[\text{ml/kg}]*\text{weight}[\text{kg}]$$

Equation 10

The 0.20 coefficient in Equation 10 was computed by analysis of collected clinical trial data. A hypothesis of the experiment was to adjust the dual flow duration and dilution ratio based on the time to peak and peak enhancement of a 20 ml timing bolus. The nomogram set forth in Table 3 below is based on the results of that trial. To compute the a priori contrast volume to load before the procedure, a linear regression was performed on the right heart enhancement values from a clinical trial as the dependent variable and the contrast volume as the independent variable.

Figure 28:
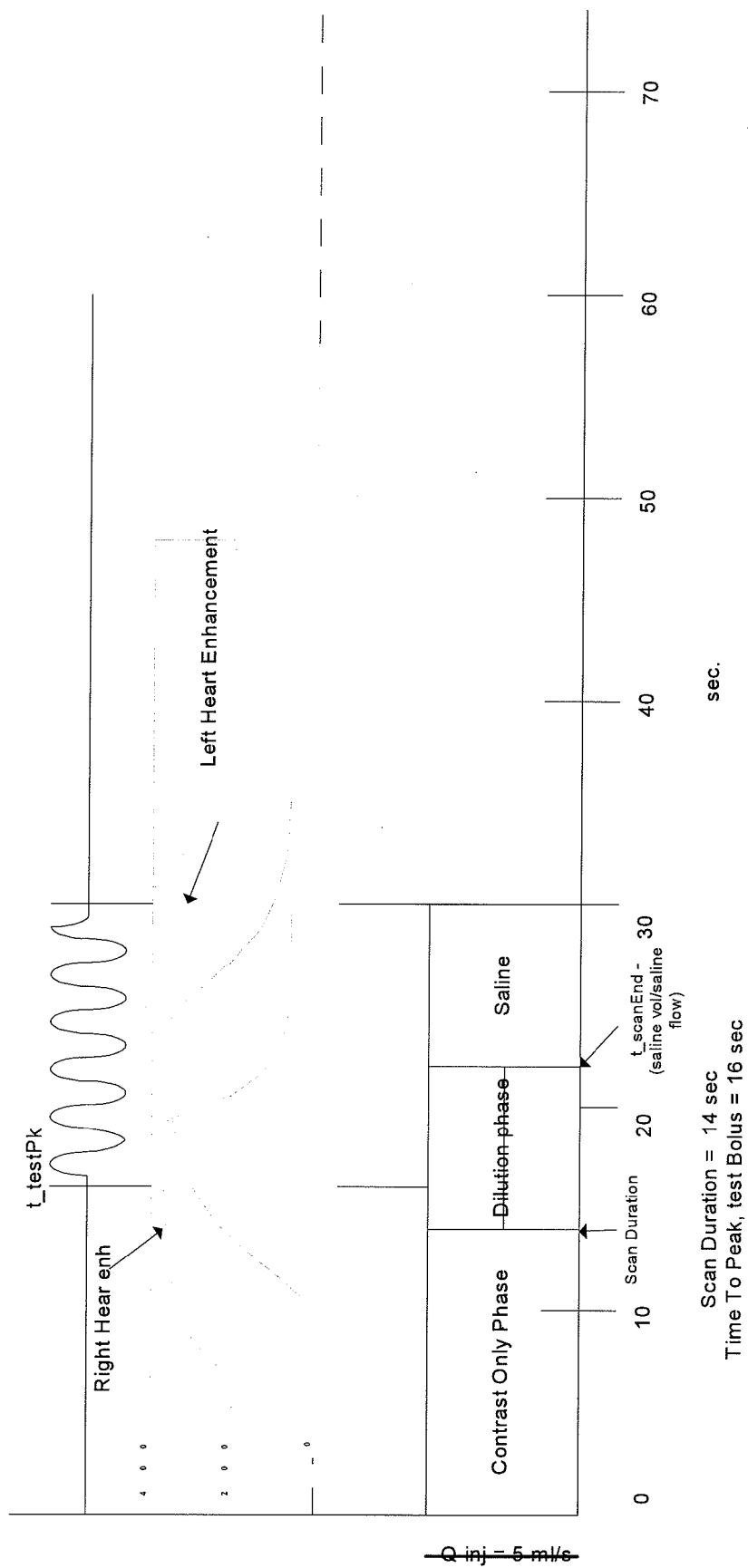
FIG. 28 illustrates a schematic of representative timing for a CTA (CT Angiography) procedure.

A schematic of the timing situation for CTA is depicted in FIG. 28. The curves are predicted enhancement curves for the right heart and left heart compartments as determined by pharmacokinetic simulation. The goal of several studies was to place a hard constraint on the end of fluid injection at Tend—the sum of scan delay plus scan duration. The delivery of contrast past the end of the scan duration makes no sense medically because the drug will not contribute to image enhancement. The dilution phase was computed, per patient, to squeeze in between the end of the injection duration and Tend. In the studies, the contrast only injection duration was set to the length of the scan. The "diagnostic", contrast only phase duration described will be longer than the scan duration. Because the outcome of the study using the personalized dilution strategy produced satisfactory right heart images (defined at right ventricle) and left heart images, the dilution phase contrast volumes were used as a standard group for this research.

Figure 29:
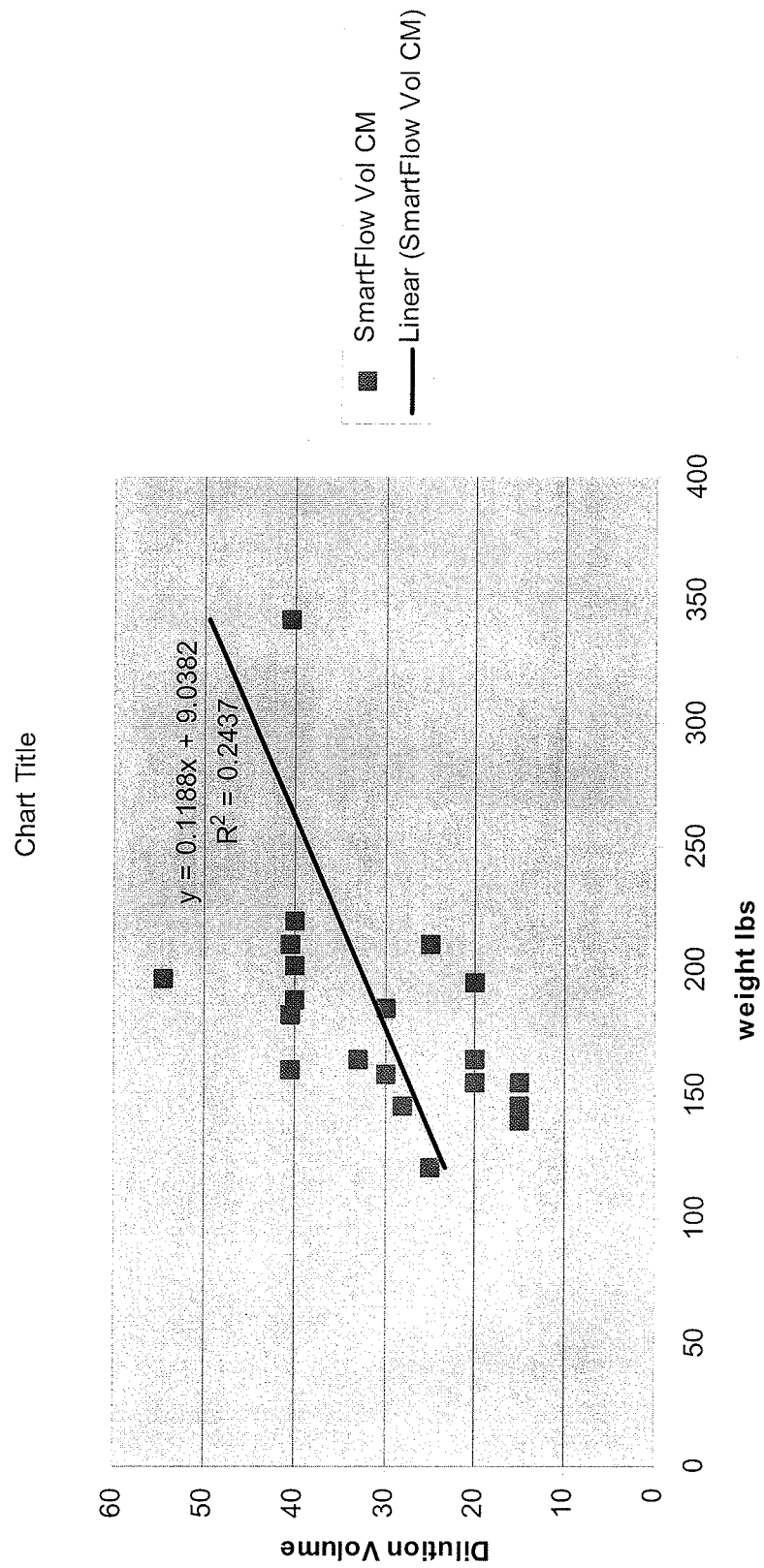
FIG. 29 illustrates raw data from a clinical trial for 20 patients wherein the y-axis is the actual volume of contrast used in the dilution phase and the x-axis is the weight of the patients in the sample (in lbs).
Figure 30:
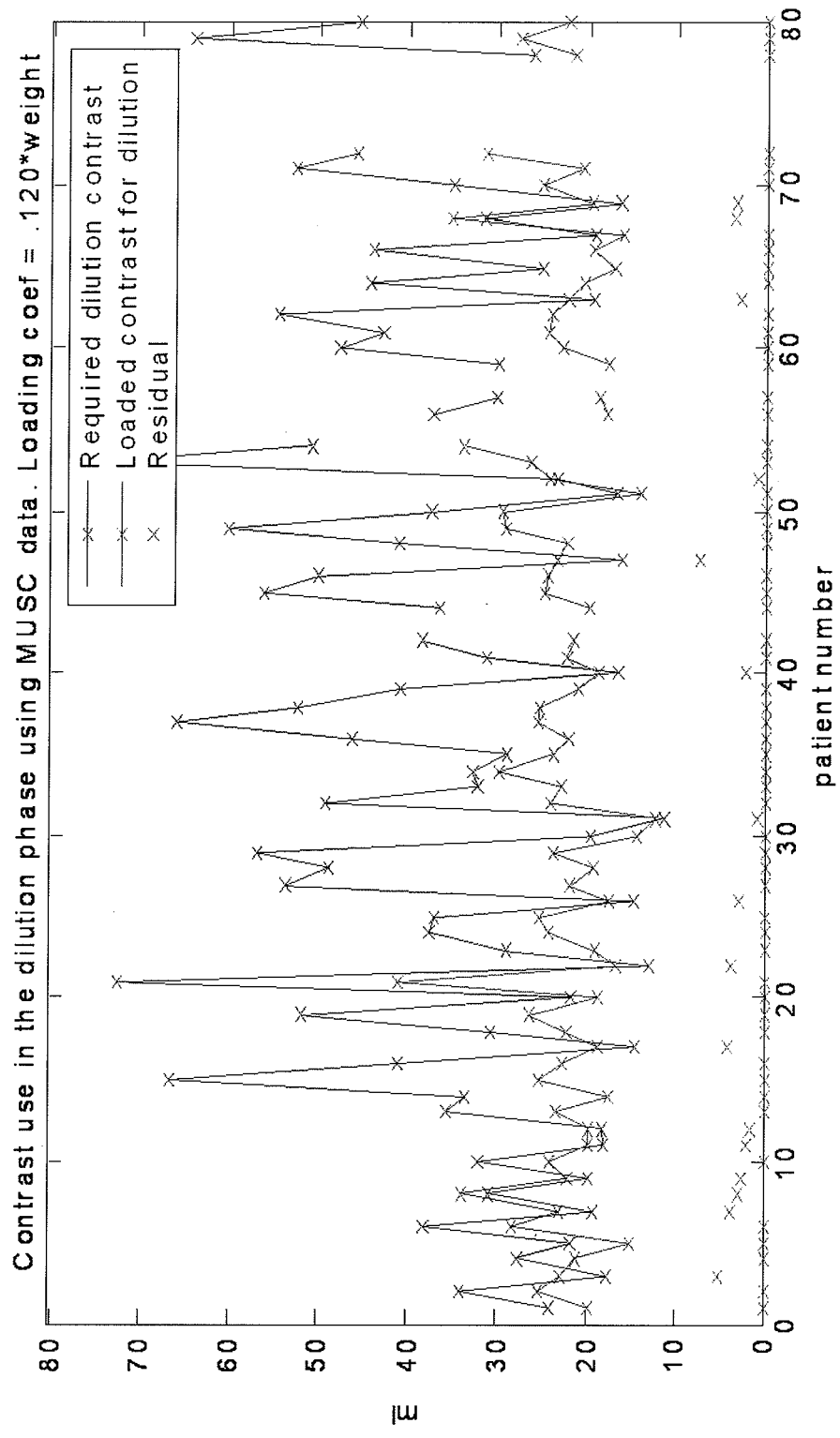
FIG. 30 illustrates a Monte-Carlo simulation using biometrics for 70 patients that computed diagnostic and dilution contrast protocols using a preloaded volume.

FIG. 29 presents the raw data from a clinical trial for 20 patients. The y-axis is the actual volume of contrast used in the dilution phase with the x-axis the weight of the patients in the sample (in lbs). FIG. 30 depicts a Monte-Carlo simulation using biometrics for 70 patients that computed diagnostic and dilution contrast protocols using the preloaded volume as determined with the coefficients in Table 1 and the volume protocols computed with Equations 3 and 10. The study was done to appreciate the volume of residual contrast that would be left in the syringe after the procedure if a loading factor of 0.12 ml/lb were used. It is evident that the residual contrast wastes for the dilution phase are below 10 ml. The units of the regression are in pounds. Converting the regression coefficient to metric, kg, units results in a coefficient of (0.120[ml/lb]*2.204[lb/kg])=0.264 ml/kg. To reduce the overall contrast dose, and considering that some of the images in the clinical trial had brighter than desired right heart enhancement, the loading coefficient for the dual flow phase was set at 0.20 ml/kg. The reduction of the loading factor has an added benefit of reducing the total Iodine burden to the patient.

Dual Flow Saline Volume

There are two instances of the DF saline volume to consider: the load volume and the adjusted DF saline volume. The DF saline phase load volume is the value that is calculated at the time of generation. It can vary from the adjusted DF saline volume if the ratio changes and has two scenarios as listed in Table 3 below

TABLE 3

| Condition | DF Ratio | | |
|---|---|---|---|
| | Weight (kg) | Ratio | Rational |
| No Test bolus | <=85 | 30% | Since we do not know the exact level of enhancement we are changing the ratio based on body weight. |
| | 102-118 | 50% | |
| | >118 | 70% | |
| Test bolus | | 30% | In the test bolus case, we do not know the actual ratio that we will be using for the DF adjustment, so we load the worst case for the saline, which is the 30% contrast ratio. This may cause some saline waste during the Test Bolus adjustment; however, saline waste is acceptable to the user. |

In all cases for Table 2 above, the saline volume is equal to:

$$V_S^{DF} = V_C^{DF} * ((1/\text{Ratio}) - 1)$$

If the total volume of contrast computed in the above procedures exceeds the capacity of the syringe on the system, then steps must be taken to reduce the contrast volume.

2.4 Volume Limiting Based On Syringe Capacity

In several studies of the present invention, 200 ml syringes were used. However, syringes of other volumes, including syringes having a volume less than 200 ml can be used. For syringe-based injector systems, situations (for example, low concentration contrast and heavy patients) must be accommodated in which it is possible that the computed load volume exceeds the volume of the syringe. Table 4 sets forth one embodiment of a rules set established to ensure that the generated protocol and the load volume does not exceed the capacity of the syringe. In several studies with 200 ml syringes, the maximum load volume was set to 195 ml.

TABLE 4

| Is there flow rate limiting too? | Contrast Reduction algorithm |
|---|---|
| No | 1. Reduce the diagnostic contrast volume until the total calculated contrast is equal to the contrast syringe capacity |
| Yes | 1. Subtract the DualFlow contrast volume from the diagnostic contrast volume.<br>2. If there is still an over volume, then reduce the DualFlow volume until 5 ml. |

TABLE 4-continued

| Is there flow rate limiting too? | Contrast Reduction algorithm |
|---|---|
| | 3. If there is still an over volume, then delete the DualFlow volume.<br>4. If there is still an over volume, then reduce the first phase volume until the syringe capacity is met. |

3.0 Protocol Adjustment Operations

Figure 31:
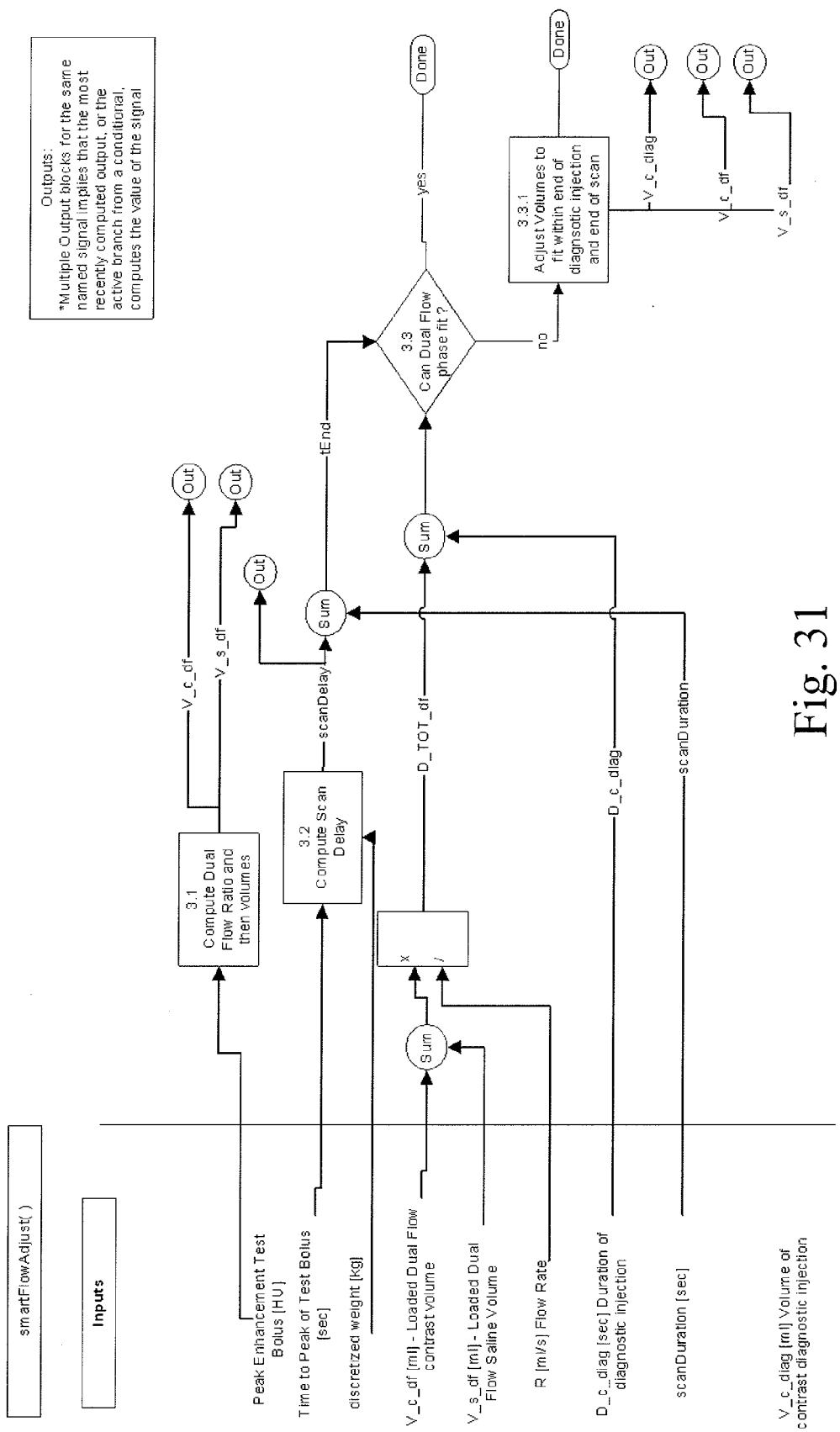
FIG. 31 illustrates a functional description of an embodiment of a protocol adjustment function that applies changes to the injection protocols based on features of a test bolus enhancement.

A protocol adjustment subroutine of the present invention modifies the loaded protocol as described above based upon a characterization of the cardiovascular system or a characterization of the propagation of a pharmaceutical (for example, including a contrast enhancing agent) through the cardiovascular system. Such characterizations can, for example, be made through the use of one or more patient models (for example, parametric models or nonparametric models as described in Published PCT Application No. WO/2006/055813 (PCT International Patent Application No. PCT/US2005/041913)) and/or through the use of a small-volume timing, identification or test bolus or injection. In several embodiments, protocol adjustment was based on data obtained in a test injection (for example, the time to peak and peak enhancement). FIG. 31 illustrates a functional description of an embodiment of a protocol adjustment function that applies changes to the injection protocols based on identification of a test bolus enhancement. The following subsections are elaborations on the correspondingly numbered operations described in FIG. 31.

3.1 Computation of Dual Flow Ratio and then Volume

Test bolus adjustments are adjustments made to the protocol after the injection of the test bolus and the user entering time to peak and peak enhancement. Alternatively, the time to peak and peak enhancement can be communicated to the protocol generation system of the present invention via a wired or wireless communication connection between the scanner and the system. This calculation does not apply to protocols without a test bolus.

TABLE 5

| Peak Enhancement HU | Ratio |
|---|---|
| >=140 | 30% |
| 80 to 139 | 50% |
| <79 | 70% |

Based on the heuristic set forth in Table 5, the actual volume of contrast to deliver in the dilution (dual flow) phase is computed as follows:

$$\hat{V}_C^{DF} = \hat{D}_{Total}^{DF} \times \text{ratio} \qquad \text{Equation 11}$$

3.2 Computation of Scan Delay Estimate

The estimate of the scan delay is based on the timing of the injection. The following calculation provides an estimate of the scan delay (in s) based on the measure or estimated values

```
if weight >= 102 kg (after the weight is discretized)
            scanDelay = Tpeak + 6
Else
            scanDelay = Tpeak + 4
end
if scanDuration < 10 sec (regardless of weight)
            scanDelay = Tpeak + 6
end
```

The additional times of, for example, 4 and 6 seconds are appended to the time to peak to anticipate the transport delay of contrast from the measurement site into the region of interest. The 6-second addition is for heavy patients in whom it is expected that the contrast will propagate more slowly through the vasculature, and who are more likely to encounter flow rate limit situations in which the contrast is injected longer than the scan duration. In the situations in which the protocol is flow rate limited and the patient weighs less than 102 kg (discretized), there is a chance (especially for lower concentrated contrast agents) that the end of the injection will occur during the time to peak of the 20 ml test bolus. It is desirable that the scan not be started during the injection while the undiluted contrast is in the SVC. The additional time delay anticipates this situation. In a situation in which the clinician performs a very short scan, the scan should be timed to start during the peak of enhancement.

Because the contrast is preloaded based on weight, a 5-second scan should make use of the contrast enhancement by starting later in the enhancement window of the left heart. The conditional then, for short scans less than 10 seconds, determines the duration of the diagnostic phase as time to peak plus 6 seconds to allow the diluted contrast time to propagate from the peripheral vein vasculature into the heart compartment—an initial purpose of providing a dilution or dual flow phase. Furthermore, the scan preferably starts after the undiluted contrast protocol has finished and some of the diluted (dual flow) contrast is reaching the SVC. This result can be realized with short scan durations, because the concern about imaging during the down slope of enhancement is less critical.

3.3 Determining if There is Sufficient Time for a Dual Flow Phase

The injection timing adjustment made after the test bolus features are provided, can, for example, attempt to end the contrast injection at the end of the scan. The following equations apply to the injection timing adjustment:

$$Tend = ScanDelay + ScanDuration$$

The duration of the dual flow phase is determined by calculating the gap between the Tend and the end of the full contrast or contrast only phase using the following equation:

$$Dgap = ScanDelay + ScanDuration - D_C^{Diag}$$

Figure 32A:
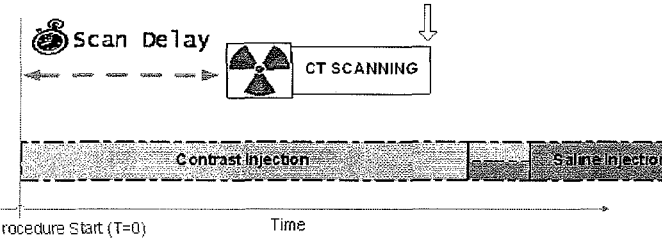
FIGS. 32A and 32B illustrate an embodiment of a process for adjusting volumes, when applicable
Figure 32B:
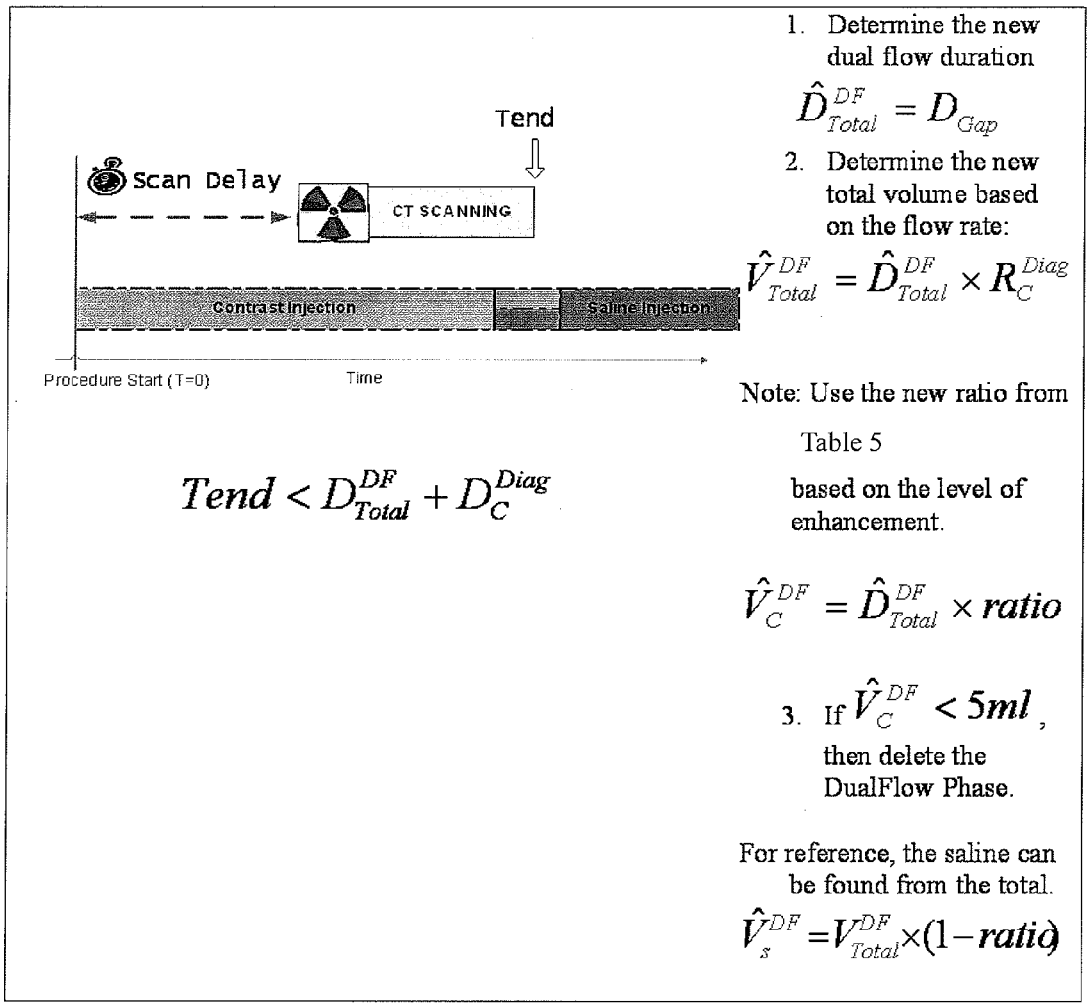

Volume can be adjusted, when applicable, as illustrated in FIGS. 32A and 32B.

Figure 26:
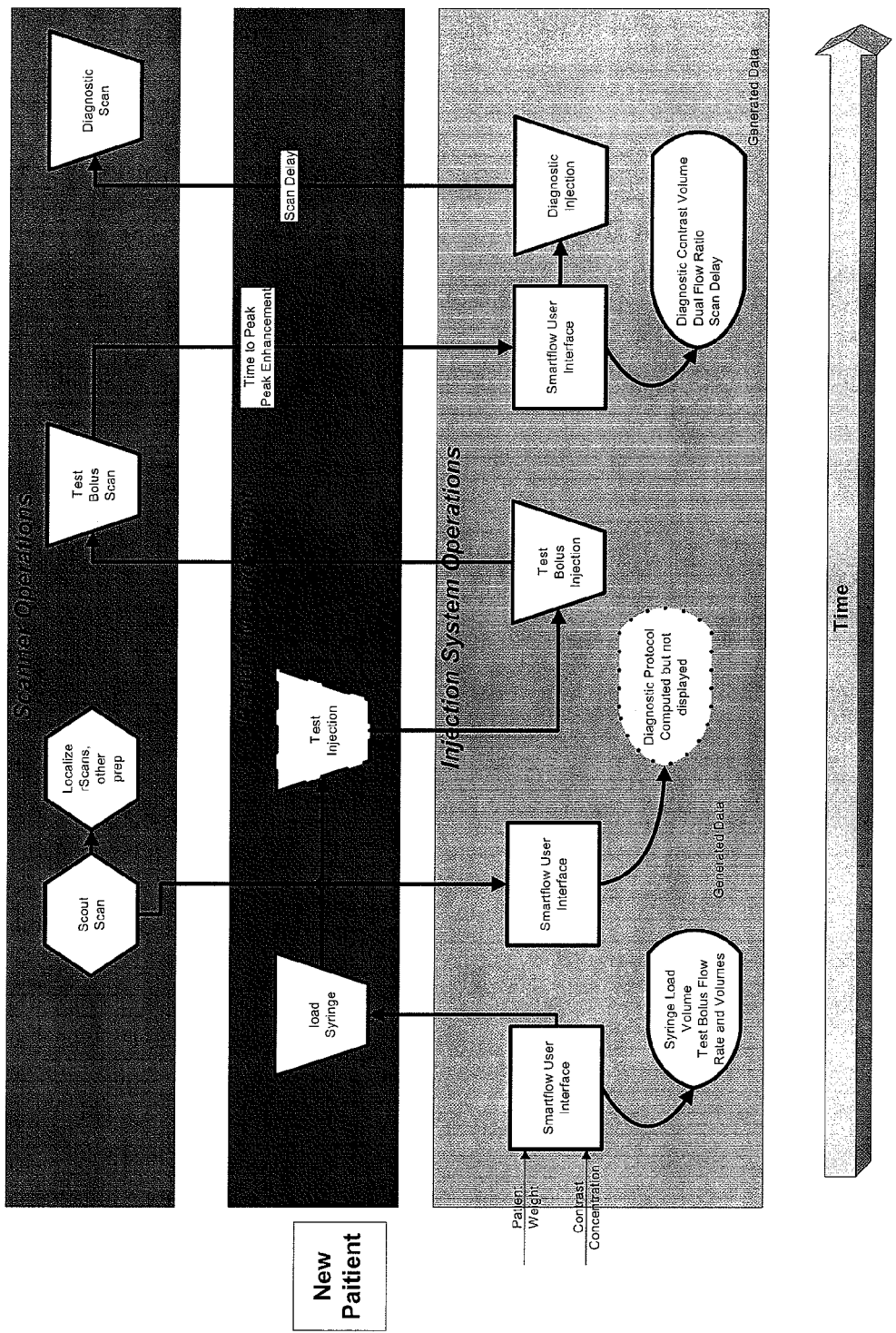
FIG. 26 illustrates an embodiment of a clinical workflow of the present invention setting forth scanner operations, patient management operations and injection system operations

FIG. 33A through 33G illustrates examples of graphical user interfaces for use with the embodiment of a protocol generation system of the present invention as described above corresponding to various points or steps along the workflow diagram set forth in FIG. 26.

Figure 33B:
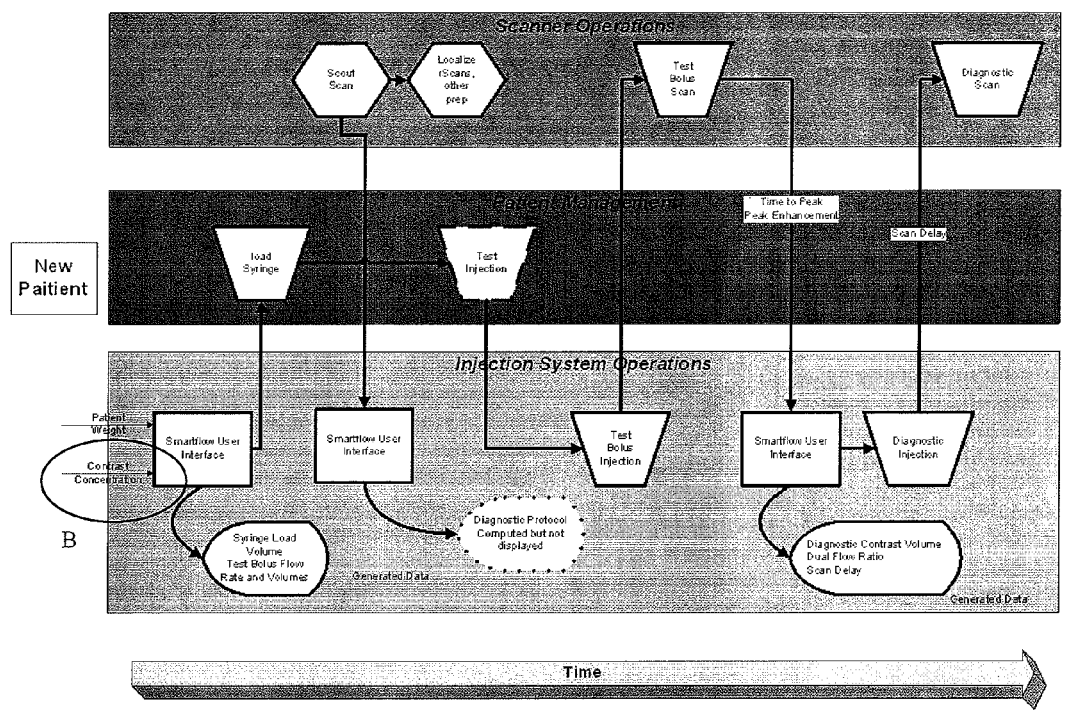
FIG. 33B illustrates the workflow diagram of FIG. 26 in which a contrast concentration input step is encircled with circle B and a corresponding graphical user interface in which contrast concentration is selected from a plurality of available choices.
Figure 33C:
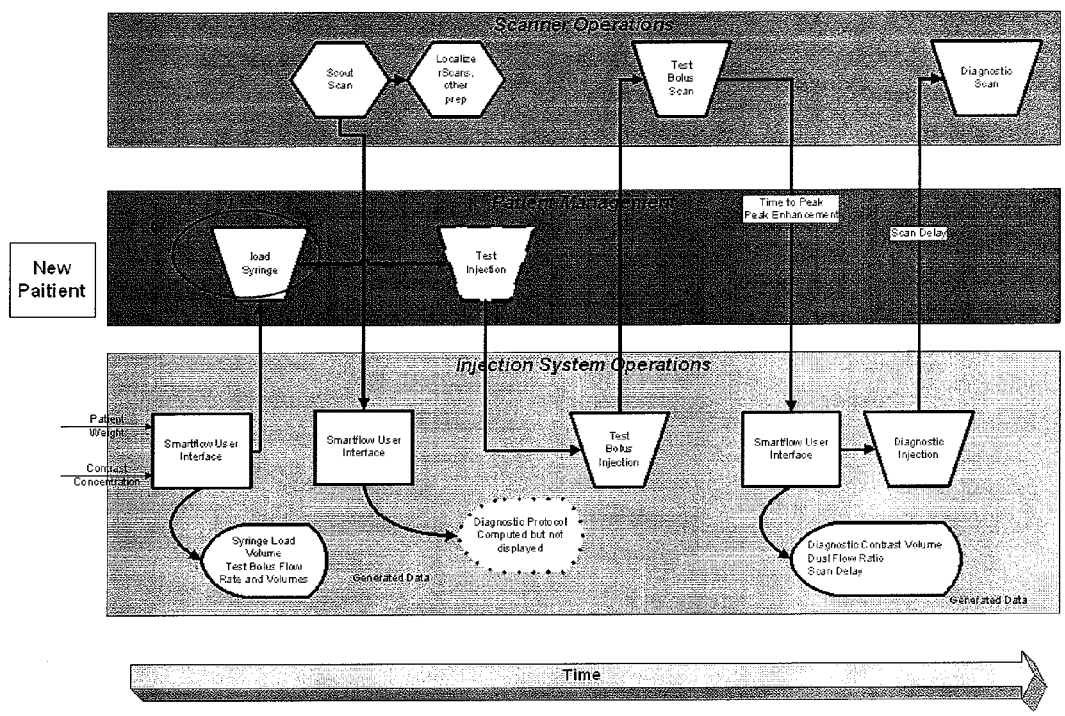
FIG. 33C illustrates the workflow diagram of FIG. 26 in which the syringe loading step is encircled with circle C and a corresponding graphical user interface or screen display in which the calculated contrast syringe and saline syringe load volumes are set forth for the user/clinician.
Figure 33D:
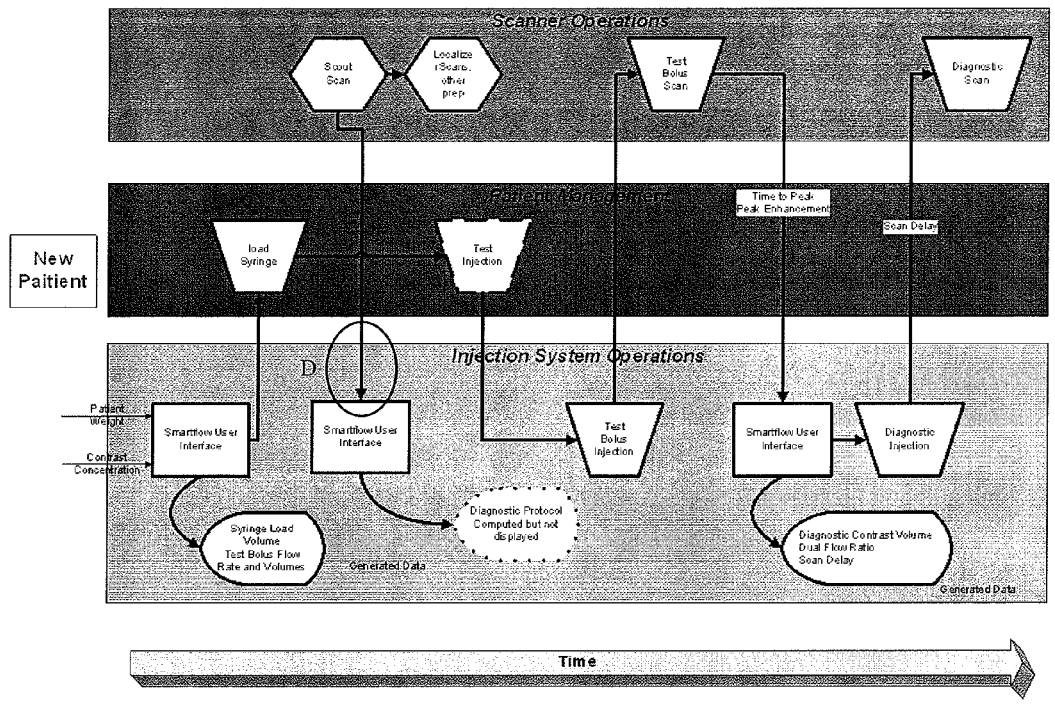
FIG. 33D illustrates the workflow diagram of FIG. 26 in which the step of data transfer from a scout scan to the protocol generation interface of the present invention is encircled with circle D and a corresponding graphical user interface for entering scan duration.

An upper portion of FIG. 33A illustrates the workflow diagram in which the step of patient weight input is encircled with circle A. A corresponding graphical user interface is illustrated in the lower portion of FIG. 33A. In this embodiment, patient weight is selected from a plurality of weight ranges. An upper portion of FIG. 33B illustrates the workflow diagram in which a contrast concentration input step is encircled with circle B. A corresponding graphical user interface is illustrated in the lower portion of FIG. 33B. In this embodiment, contrast concentration is selected from a plurality of available choices. An upper portion of FIG. 33C illustrates the workflow diagram in which the syringe loading step is encircled with circle C. A corresponding graphical user interface or screen display is illustrated in the lower portion of FIG. 33C, in which the contrast syringe and saline syringe load volumes (as calculated via the method described above) are set forth for the user/clinician. An upper portion of FIG. 33D illustrates the workflow diagram in which a data transfer step in which data from a scout scan is transferred to the interface, is encircled with circle D. A corresponding graphical user interface for entering scan duration is illustrated in the lower portion of FIG. 33D. An upper portion of FIG. 33E illustrates the workflow diagram in which an initial diagnostic protocol computation step (effected as described above) is encircled with circle E. The computed initial or preload protocol need not be displayed. A corresponding graphical user interface is illustrated in the lower portion of FIG. 33E, wherein the user is prompted to have the protocol generation system generate the protocol by, for example, pressing an OK button. An upper portion FIG. 33F illustrates the workflow diagram in which a data transfer step in which data from a test bolus is transferred to the interface is encircled with circle F. As clear to those skilled in the art, this data (for example, time to peak and peak enhancement) can be transferred via a communication link between the scanner and the injector without clinician involvement or by manual input by a clinician. A corresponding graphical user interface for manual data entry of the time to peak and peak enhancement is illustrated in the lower portion of FIG. 33F. In this embodiment, a plurality of-ranges peak enhancement is provided for choice by the clinician. An upper portion FIG. 33G illustrates the workflow diagram in which the point at which the determination of the adjusted diagnostic protocol has been completed by the interface and the diagnostic injection can be initiated is encircled with circle G. A corresponding graphical user interface for setting forth the adjusted diagnostic protocol is illustrated in the lower portion of FIG. 33D. The clinician can be provided with the opportunity to change protocol parameters.

Figure 34A:
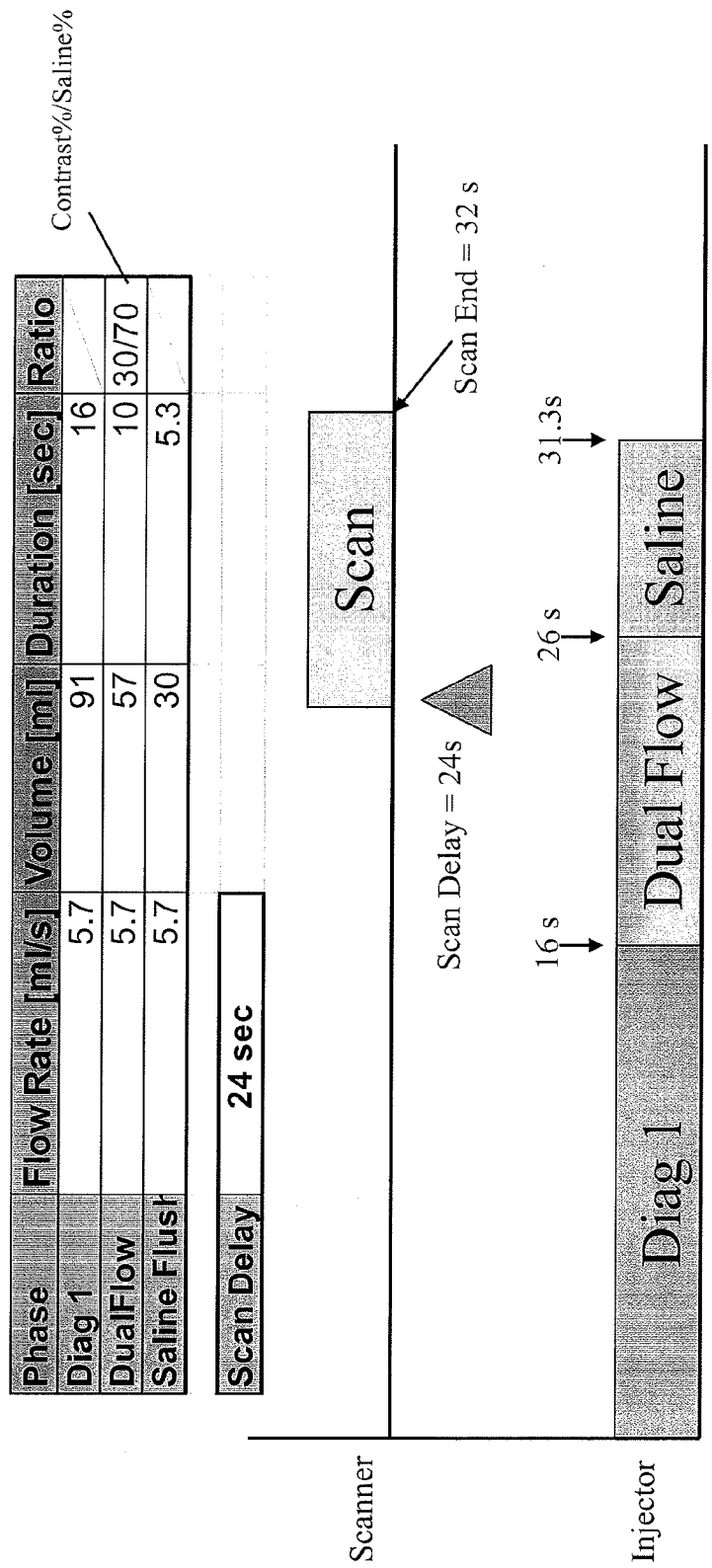
FIG. 34A illustrates an embodiment of another graphical user interface for use in connection with the present invention and a representation of an ideal contrast injection with relationship to a scan
Figure 35B:
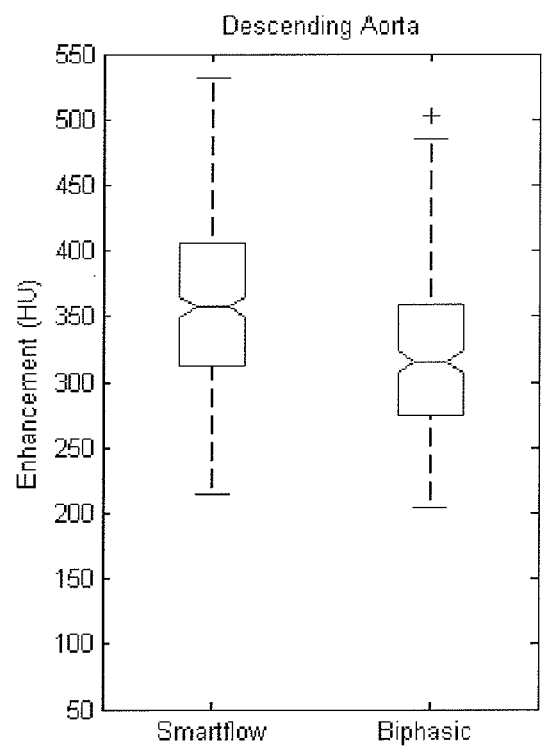
FIG. 35B illustrates enhancement results obtained in the descending aorta using a protocol generated by a protocol generation process of the present invention as compared to the results obtained using a biphasic protocol.
Figure 35C:
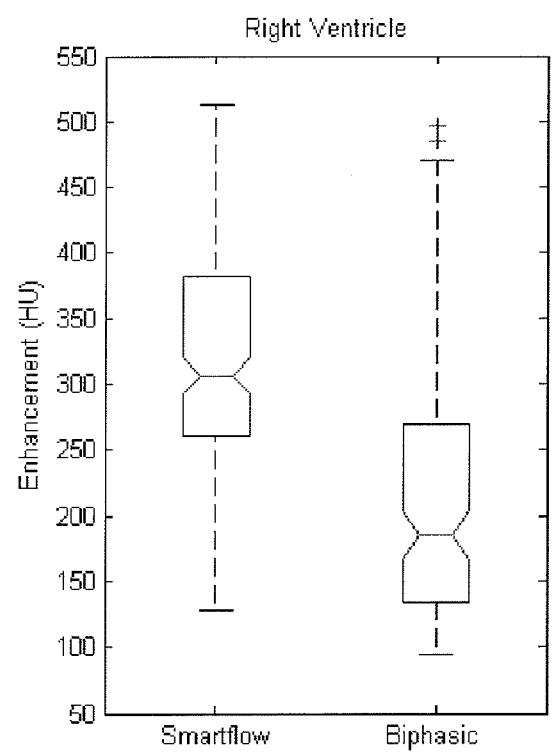
FIG. 35C illustrates enhancement results obtained in the right ventricle using a protocol generated by a protocol generation process of the present invention as compared to the results obtained using a biphasic protocol.

FIG. 34A illustrates an embodiment of a display of injector and scanner time lines for a 180 pound male patient undergoing an 8-second Cardiac CTA scan. FIG. 34B illustrates representative volumetric flow rates and iodine administration rates for a contrast only phase (phase 1) and a dual flow or admixture phase as determined by the protocol generation method.

In summary, as discussed above, a number of scan procedures such as Cardiovascular MSCT angiography are challenging as a result of decreasing acquisition periods and the challenges inherent to contrast agent delivery and use. Moreover, in the case of cardiovascular MSCT angiography cardiac structures are moving during the scan. The timing of scanner acquisition should coincide with the period when the bolus of contrast material provides maximum contrast enhancement in key anatomical structures. The protocol generation systems and methods of the present invention calculate or determine patient personalized CT contrast medium injection protocols.

In several studies of the protocol generation systems and methods of the present invention, a multi-objective optimization's goal was set at least 350 HU peak enhancement in the left heart compartment of the physiologic PK model and enhancement greater than 300 HU for at least the duration of the scan. Personalized scan delays were computed as a function of individual cardiac function (scan delay=time to peak of test bolus+4 or 6 seconds depending on patient weight and scan duration). The patient's cardiac response determined the duration and contrast to saline ratio of a dilution phase. Finally, the injection of contrast material was prohibited from extending beyond the end of the scan and, in most cases, ends 5-6 seconds prior.

It was expected that left and right heart contrast enhancement would be more consistent across subjects using the cardiac protocol generation system/method of the present invention as compared to typical methods of establishing protocol parameters. To evaluate the level and consistency of enhancement, cardiac CE CT data from a pilot study were analyzed. Two anatomic regions of interest (the descending aorta and the right ventricle) were identified in each subject's scan (reconstructed at 60% RR interval) via a semi-automatic segmentation algorithm. For every set of axial slices acquired at a single time point, the mean enhancement within each of the regions was computed, yielding time enhancement curves. The influence of a per-patient, contrast injection protocol having a dilution phase on right heart enhancement during cardiac CTA was also studied. Sufficient enhancement for assessment of the right heart allows for the assessment of right heart pathology. As illustrated in FIG. 35A, the inter-subject variability in the right heart as measured by the Standard Error of the Mean was lowest in the group in which the protocol generation system/method of the present invention was used (+/−13 HU). Standard Errors in the other groups were: uni-phasic (+/−39 HU)), bi-phasic (+/−39 HU), and fixed dilution phase (+/−28 HU). A one-way ANOVA (P<0.005) demonstrated that a significant difference existed in the mean enhancement values among the injection protocol groups (also checked with Two sample F-tests for variability, P<0.001). Left Heart Enhancement averaged 325 HU +/−80

A study of 20 patients undergoing cardiovascular CTA (Siemens Sensation 64) using injection protocols generated using the system/method of the present invention (Iopimidol 370) and 19 control subjects with a standard biphasic protocol (Iopimidol 370 contrast volume=scan duration×5 ml/s, followed by a 40 ml saline flush) was made. All values of the time enhancement curves were pooled across subjects, and the two groups were compared via unpaired t-tests. The mean enhancements for the protocols generated by the present invention and the biphasic protocols were 357±69 HU and 323±64 HU, respectively ($p=10^{-8}$). The right ventricle mean enhancements were 318±85 HU and 212±96 HU ($p=10^{-21}$). These results, illustrated in FIGS. 35B and 35C, respectively, show statistically significant differences in enhancement in both regions.

Figure 36A:
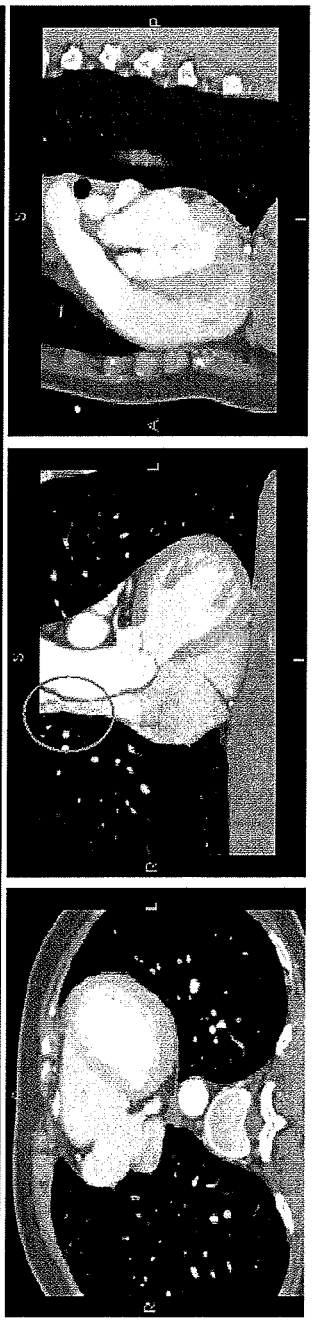
FIG. 36A illustrates CTA scan results obtained using a protocol generated by a protocol generation process of the present invention for a 139 pound female subject.
Figure 36B:
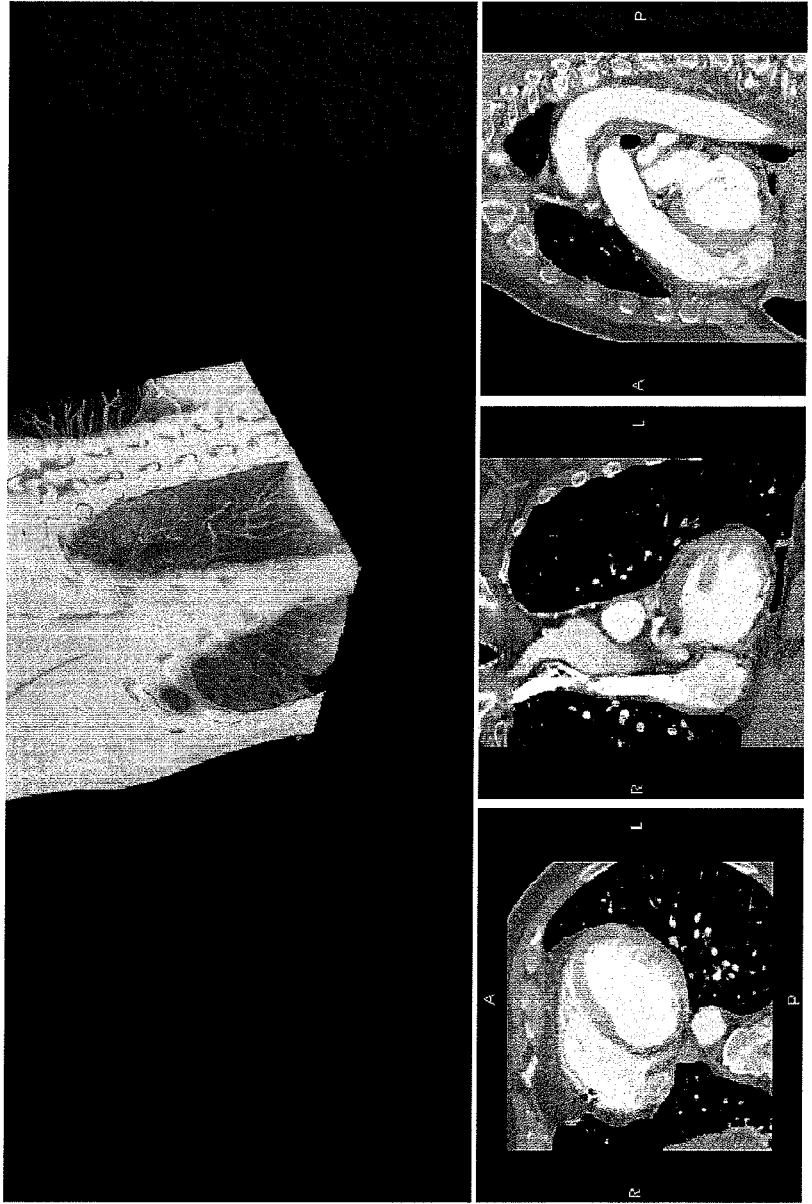
FIG. 36B illustrates CTA scan results obtained using a protocol generated by a protocol generation process of the present invention for a 202 pound male subject.

FIG. 36A illustrates scan results obtained using a protocol generated by a protocol generation process of the present invention for a 139 pound female subject while FIG. 36B illustrates scan results obtained using a protocol generated by a protocol generation process of the present invention for a 202 pound male subject. Noticeable in these images is the bright, uniform opacification of the left heart structures (left atrium, ventricle, and left anterior descending coronary artery origin). In both images there is also sufficient enhancement of the right ventricle, atrium and superior vena cava to provide for differentiation of the intraventricular septum, the margin of the myocardium. There is also sufficient opacification to provide for functional analysis of right ventricular function. Furthermore, enough contrast is present in the right heart to allow for the diagnosis of thrombo-emboli. Furthermore, visualization of the right ventricle papillary muscles, the moderator band and the tricuspid valve is possible via the presence of homogenous contrast enhancement. In both images there is a lack of streaking artifact often associated with contrast media residing in the superior vena cava, right atrium and right ventricle during CT scan acquisition (see the circle in FIG. 36A). The homogeneity of the right heart enhancement and lack of streaking artifact is a result of the administration of a personalized, dilution protocol and optimal scan timing (in relation to the propagation of contrast media in vivo) provided by the systems and methods of the present invention.

In another study of the systems and methods of the present invention, injection protocols were integrated with an injector for cardiac dual-source CT (DSCT). In a study group of 40 consecutive patients undergoing cardiac DSCT, a parameter generation system/method of the present invention as described above, which was implemented via software resident on a Medrad STELLANT injector, was prospectively evaluated for determining individualized contrast (370 mgI/ml) volume and injection parameters for a triphasic (contrast, contrast/saline and saline phase) injection protocol. The workflow procedure for the 40 patients of the study group was similar to that set forth in FIGS. 33A through 33G.

A control group of another 40 consecutive patients were injected using a standard contrast protocol and retrospectively analyzed to compare the level and homogeneity of enhancement within the aorta, coronary arteries, myocardium and ventricles. The standard protocol was a triphasic protocol in which first phase was a contrast only phase, the second phase was an admixture or dual flow phase and the third phase was a saline only phase. The flow rate was set at 6 ml/second for all phases. The dual flow phase (contrast/saline) was characterized by delivery of 50 ml of fluid including 30% contrast medium and 70% saline at 6 ml/second. The saline phase was characterized by delivery of 40 ml of saline injected at 6 ml/second. Before the triphasic diagnostic protocol of the control group, a test bolus of 20 ml of contrast medium at 6 ml/sec followed by injection of 40 ml of saline 6 ml/second was used to determine the scan delay, which was determined as the time to peak enhancement in the ascending aorta.

Figure 37:
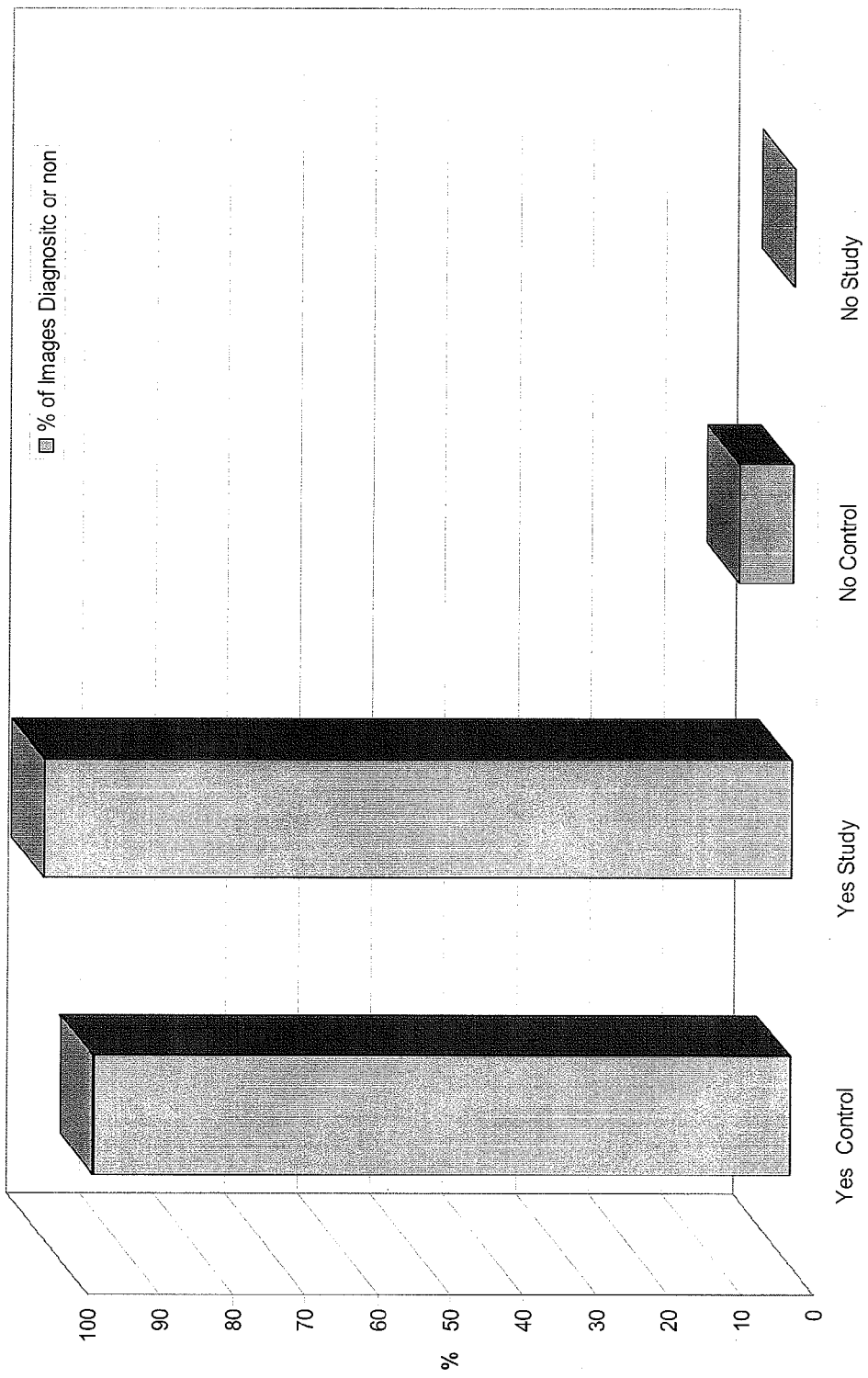
FIG. 37 illustrates a summary of answers provided by two blinded readers to the questions: "For this patient's intended diagnosis, do you believe that the contrast medium delivery protocol was sufficient to visualize anatomy and diagnose pathology?" for a study group in which the protocol was determined using a parameter generation system of the present invention and for a control group in which a standard protocol was used.

The quality of diagnostic display of cardiac anatomic landmarks was rated for each of the study group and the control group. FIG. 37 sets forth a graphical representation of answers of two blinded readers of the question: "For this patient's intended diagnosis, do you believe that the contrast medium delivery protocol was sufficient to visualize anatomy and diagnose pathology?" Yes and no responses were accumulated for each of the control group and the study group and are set forth as percent yes/diagnostic or no/non-diagnostic. As set forth in FIG. 37, the blinded readers found that the contrast medium delivery protocol generated using the parameter generation system of the present invention was sufficient to visualize anatomy and diagnose pathology in 100% of the study group patients, while the blinded readers found that the contrast medium delivery protocol generated using the standard methodology was sufficient to visualize anatomy and diagnose pathology in only 92% of the control group patients.

Figure 38:
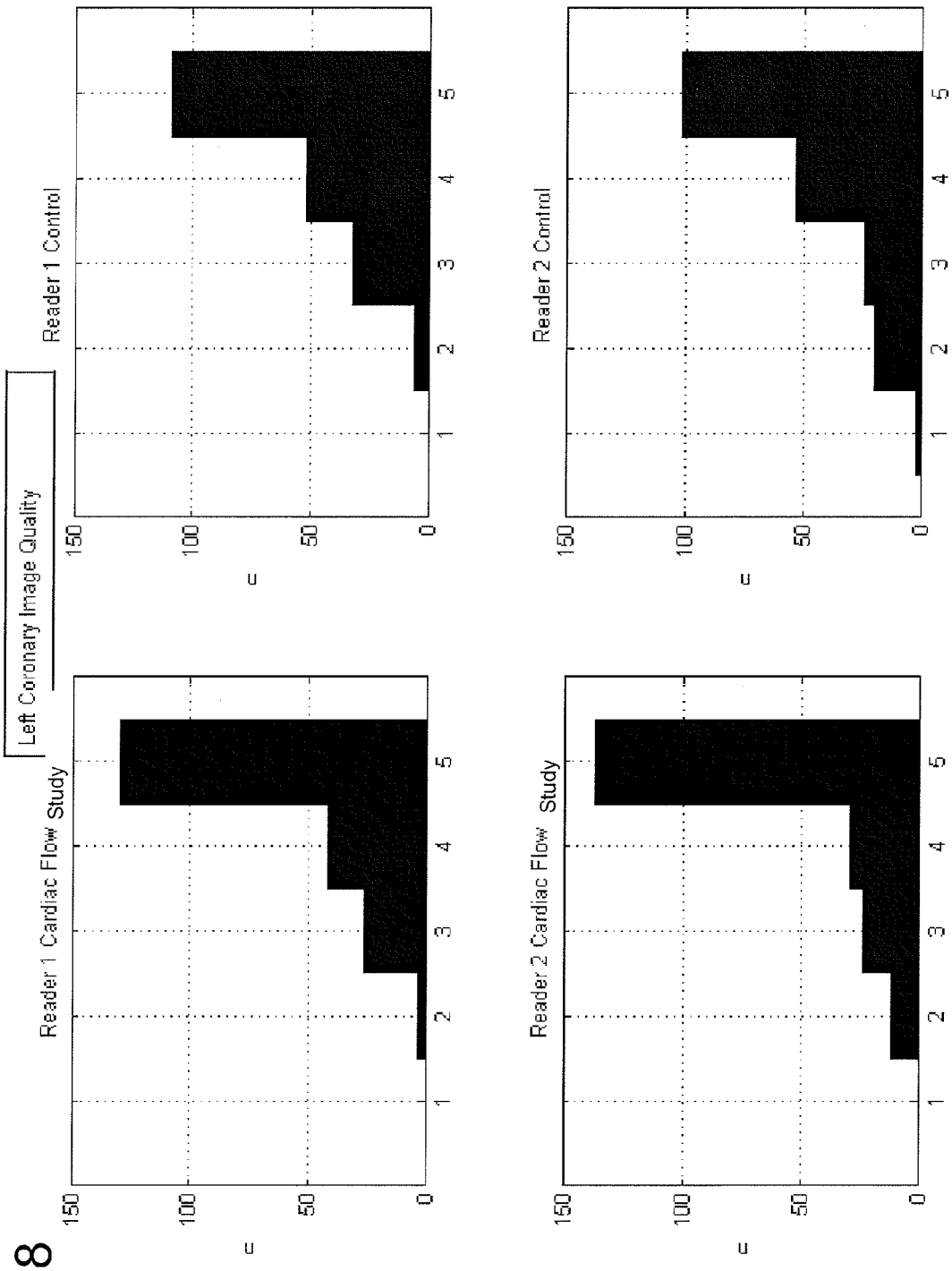
FIG. 38 illustrates a graphical representation of ratings by two blinded readers of the imaging achieved by each of a contrast medium delivery protocol generated using a parameter generation system of the present invention (study group) and a standard contrast medium delivery protocol (control group) for left coronary imaging wherein a rating or "1" corresponds to the conclusion that the structure in question was not visualized, a rating of "2" corresponds to a conclusion that the structure in question is faintly visualized, a rating of "3" corresponds to a conclusion that the structure in question is faintly visualized and delineation is limited, a rating of "4" corresponds to a conclusion that the structure in question is visualized and complete delineation is possible, a rating of "5" corresponds to a conclusion that the structure in question is excellently visualized and delineation is excellent.
Figure 39:
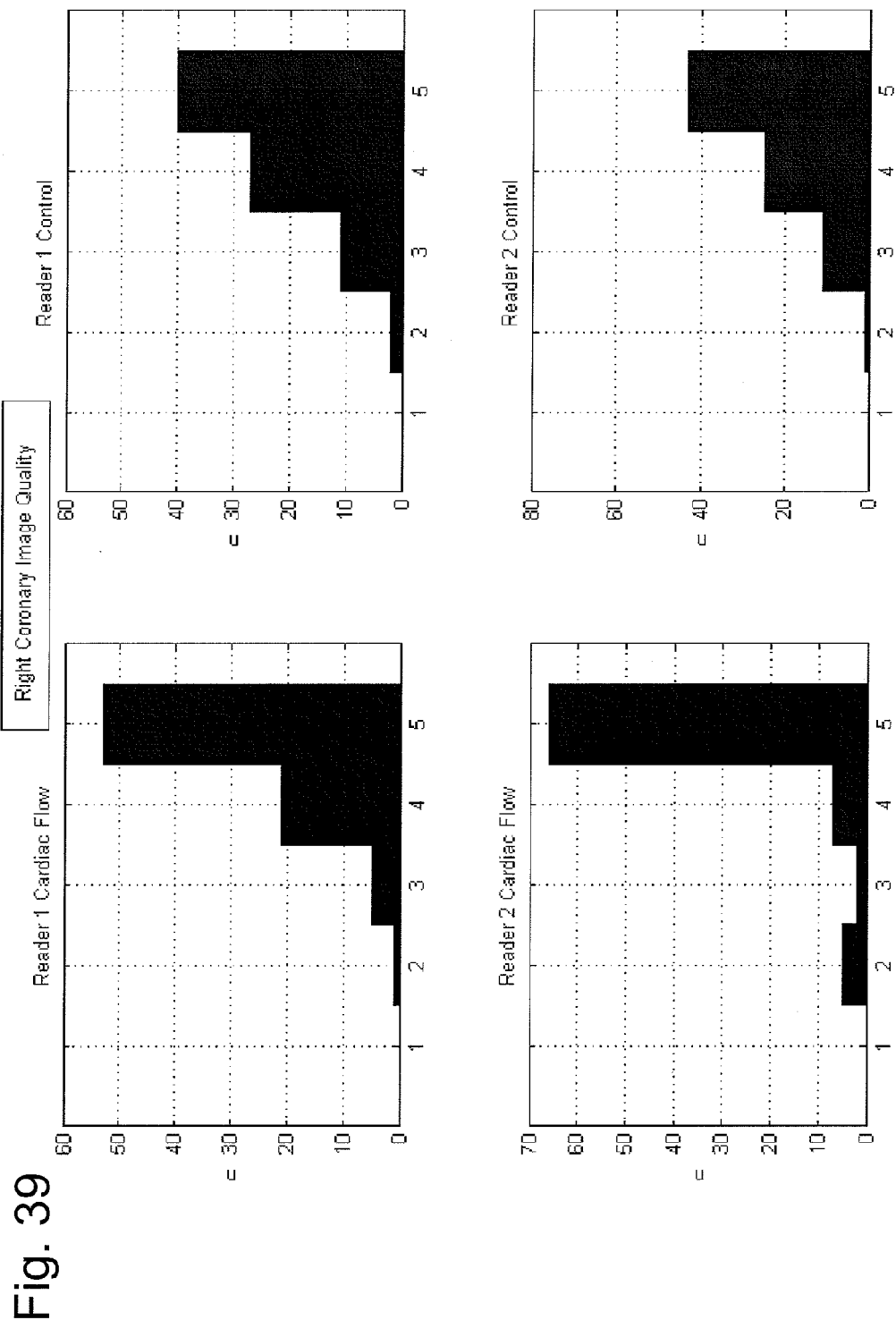
FIG. 39 illustrates an analysis similar to that of FIG. 39 for right coronary imaging.

FIG. 38 sets forth a graphical representation of ratings by the blinded readers of the imaging achieved by each of the contrast medium delivery protocol generated using the parameter generation system of the present invention (study group) and the standard contrast medium delivery protocol for left coronary imaging. In FIG. 38, a rating or "1" corresponds to the conclusion that the structure in question was not visualized, a rating of "2" corresponds to a conclusion that the structure in question is faintly visualized, a rating of "3" corresponds to a conclusion that the structure in question is faintly visualized but delineation is limited, a rating of "4" corresponds to a conclusion that the structure in question is visualized and complete delineation is possible, a rating of "5" corresponds to a conclusion that the structure in question is excellently visualized and delineation is excellent. As illustrated in FIG. 38, a statistically significant advantage is provided by the methods and systems of the present invention. FIG. 39 sets forth a similar analysis for right coronary imaging. Once again, a statistically significant advantage is provided by the methods and systems of the present invention. Similar results were observed in other anatomical structures of the heart.

Figure 40:
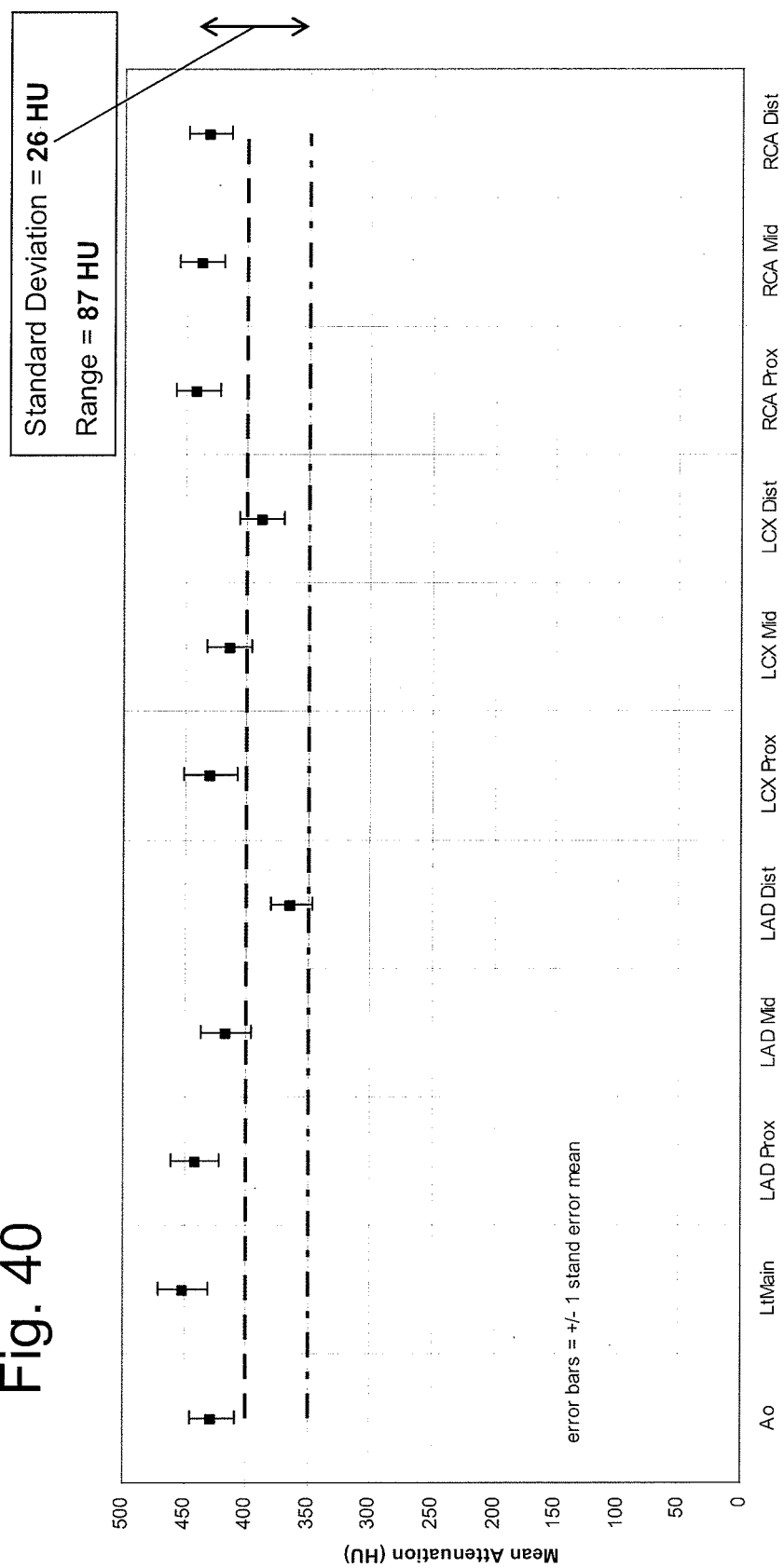
FIG. 40 illustrates mean attenuation achieved for imaging of various regions of interest for a contrast medium delivery protocol generated using a parameter generation system of the present invention (study group).
Figure 41:
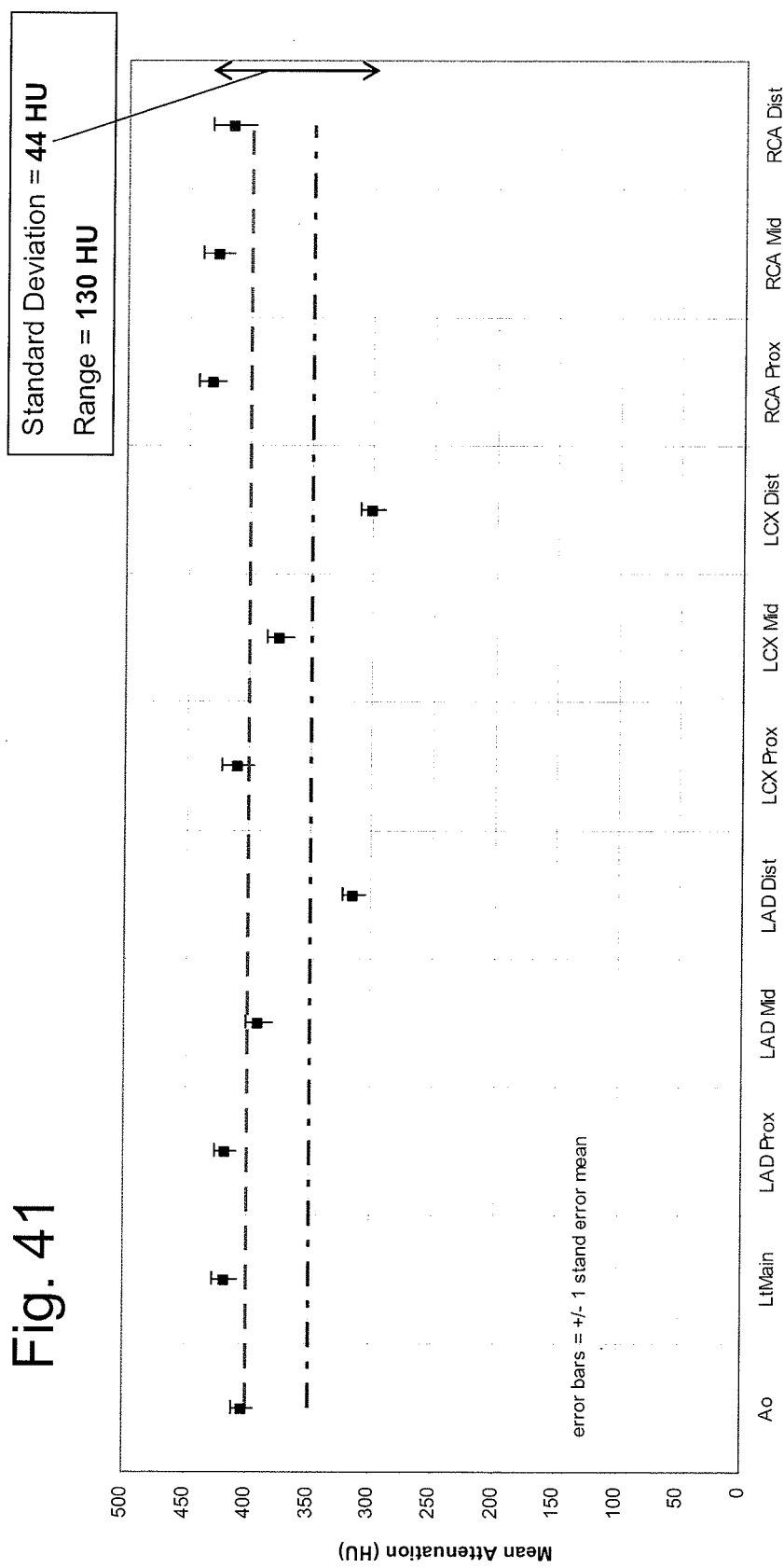
FIG. 41 illustrates mean attenuation achieved for imaging of various regions of interest for a standard contrast medium delivery protocol (control group).

As illustrated in FIGS. 40 and 41, respectively, mean coronary attenuation ranged from 359.5±17.7 to 450.6±19.9HU, and from 297.3±11.1 to 429.8±10.9HU in the study and control groups. In FIGS. 40 and 41, the abbreviation Ao refers the Ascending Aorta, the abbreviation LtMain refers to the Left Main Coronary artery, the abbreviation LAD refers to the Left Anterior Descending Coronary Artery, the abbreviation RCA refers to the Right Coronary Artery and the abbreviation LCx refers to the Circumflex Coronary Artery. The designations Prox (Proximal), Dist (Distal), and Mid refer to the distal, proximal and mid segments of each coronary artery as defined by the American Heart Association 15 segment coronary model. Mean attenuation in the distal LAD, mid and distal LCx, and the right ventricle were significantly ($p<0.05$) higher in the study group than in the control group. Intra-subject variability of vascular attenuation was significantly ($p<0.002$) lower in the study group (SD=49±19.5) than in the control group (SD=63.2±22.1). The diagnostic display of right heart structures (papillary muscles, pulmonary valve, ventricular myocardium), left main, LAD and proximal right coronary arteries were rated significantly ($P<0.05$) higher in the study group than in the control group. The patient-specific contrast protocol generated by the systems and methods of the present invention thus provided higher and more uniform coronary enhancement and improved diagnostic display of the heart in cardiac DSCT.

In still another study, enhancement in coronary arteries and ventricles using two different triphasic injection protocols with fixed parameters and one injection protocol with individually optimized injection parameters as determined by a parameter generation system/method of the present invention.

In that study, 15 patients were included in each group. In group 1, 70 ml of contrast medium (Ultravist 370, Schering) were injected with a flow-rate of 5.0 ml/second in a contrast only phase. In group 2, 80 ml of the contrast medium were injected with a flow-rate of 6.0 ml/second in a contrast only phase. For group 3 injection parameters were calculated using the parameter generation system of the present invention. Enhancement was measured in the proximal, mid and distal right coronary artery or RCA and in cranial and caudal sections of the right and left ventricle. Measurements were compared using the Mann-Whitney-U test.

In each of the control groups, group 1 and group 2, a triphasic injection protocol was used. In group 1, the flow rate throughout each of the three phases was 5 ml/second. As set forth above, 70 ml of contrast was injected in the first, contrast only phase, of group 1. In the second, dual flow, phase of group 1, 50 ml of a mixture of contrast medium and saline was injected. In the third, saline only, phase of group 1, 40 ml of saline was injected. In group 2, the flow rate throughout each of the three phases was 6 ml/second. As set forth above, 80 ml of contrast was injected in the first, contrast only phase, of group 2. In the second, dual flow, phase of group 2, 50 ml of a mixture of contrast medium and saline was injected. In the third, saline only, phase of group 2, 40 ml of saline was injected. In both of the group 1 and group 2 protocols, a test bolus was performed to determine timing/scan delay.

Figure 42:
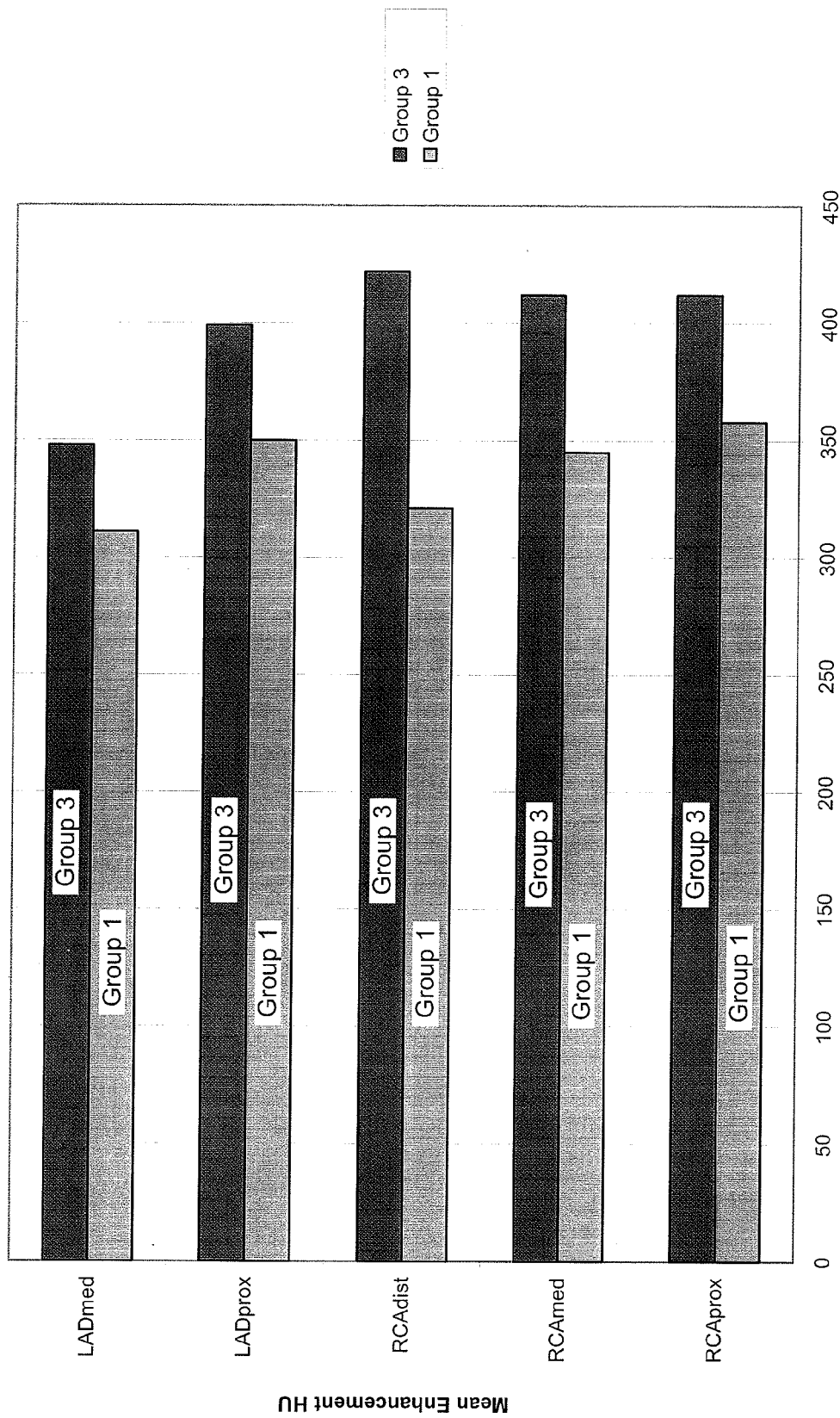
FIG. 42 illustrates mean attenuation achieved for various regions of interests (coronary arteries) for each of a standard contrast medium delivery protocol in which 70 ml of contrast medium (Ultravist 370, Schering) were injected with a flowrate of 5.0 ml/s (Group 1) and a contrast medium delivery protocol generated using a parameter generation system of the present invention (Group 3).
Figure 43:
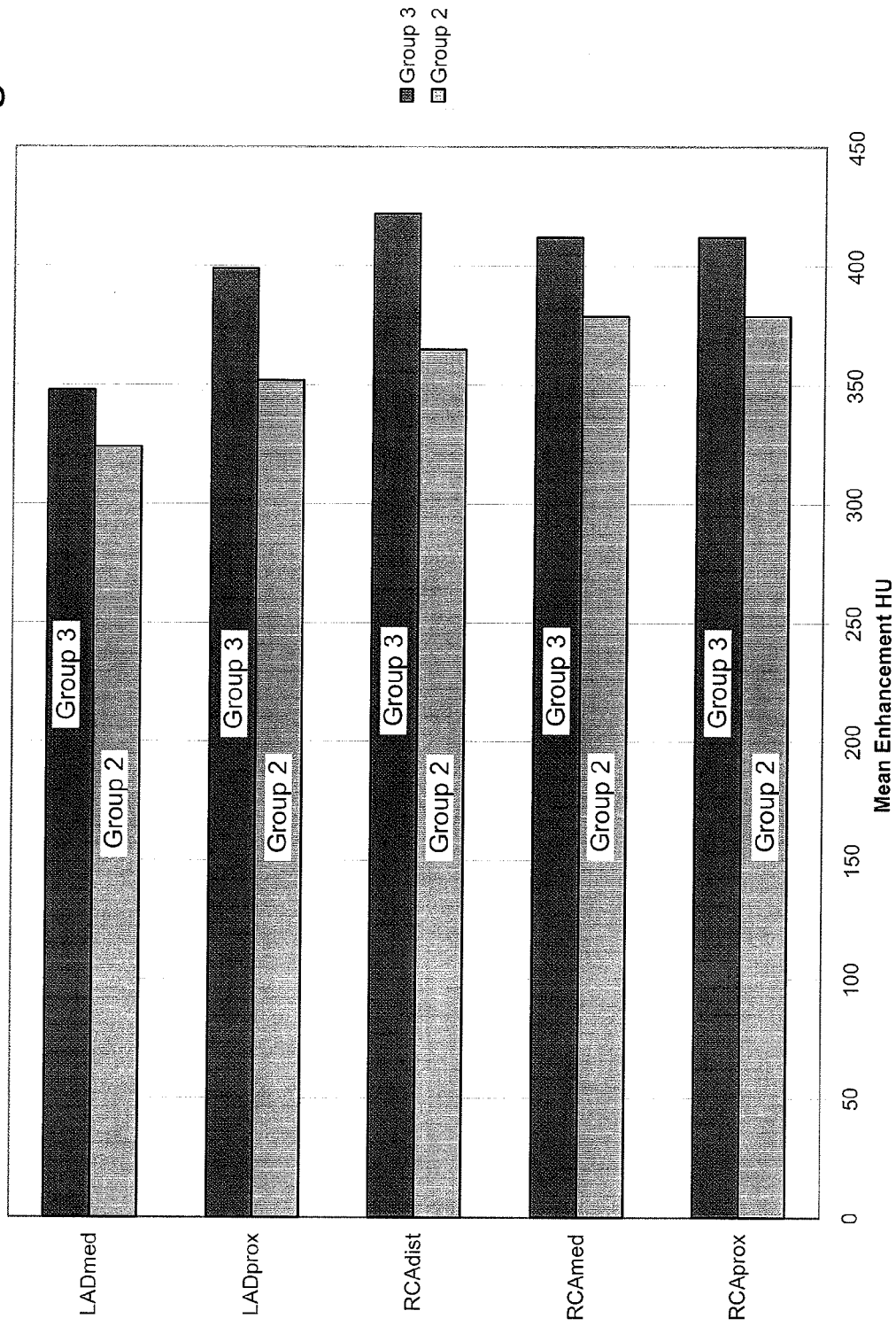
FIG. 43 illustrates mean attenuation achieved for various regions of interests (coronary arteries) for each of a standard contrast medium delivery protocol in which 80 ml of contrast medium were injected with a flow-rate of 6.0 ml/s (Group 2) and a contrast medium delivery protocol generated using a parameter generation system of the present invention (Group 3).
Figure 44:
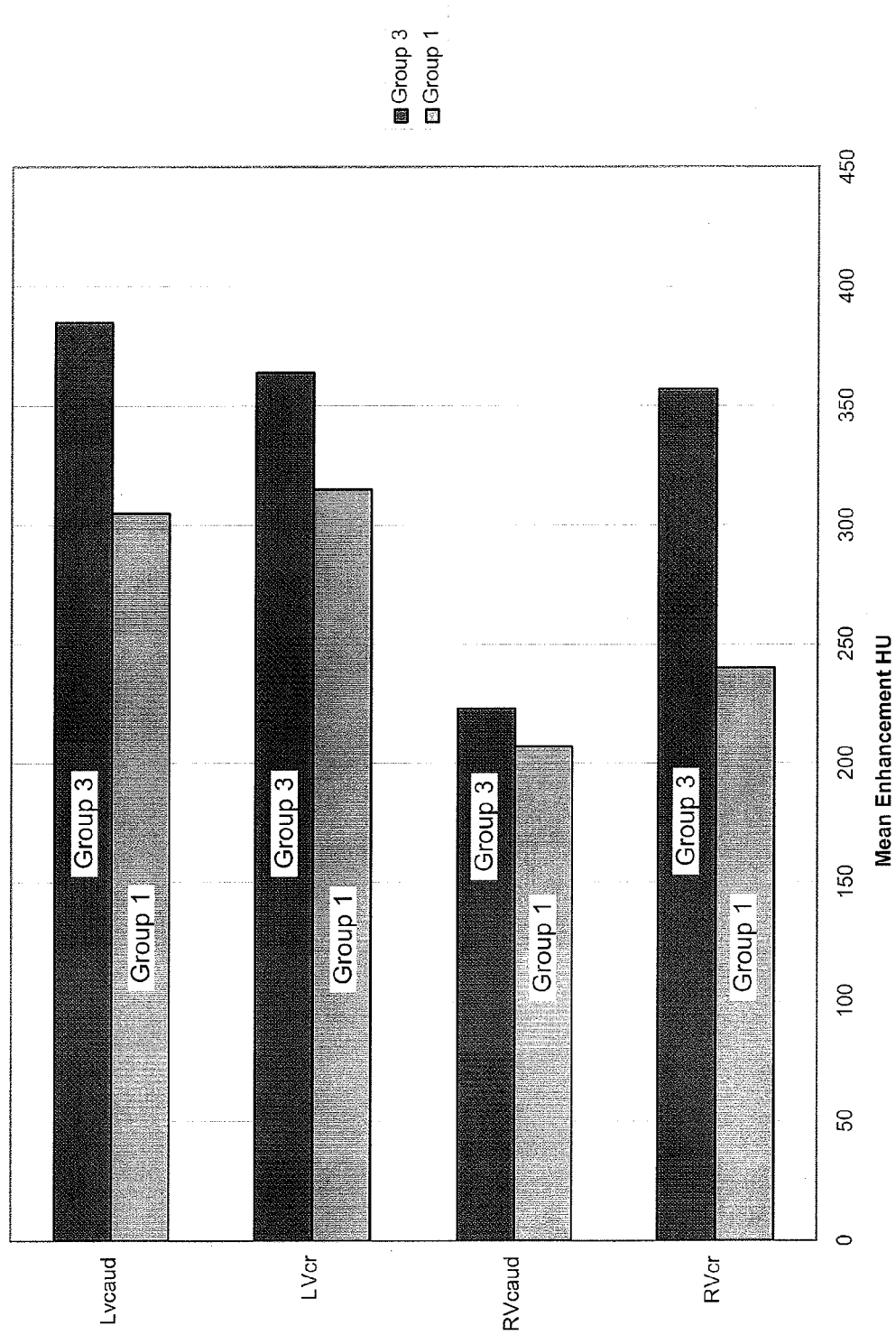
FIG. 44 illustrates mean attenuation achieved for various regions of interests (left and right ventricles) for each of a standard contrast medium delivery protocol in which 70 ml of contrast medium (Ultravist 370, Schering) were injected with a flow-rate of 5.0 ml/s (Group 1) and a contrast medium delivery protocol generated using a parameter generation system of the present invention (Group 3).
Figure 45:
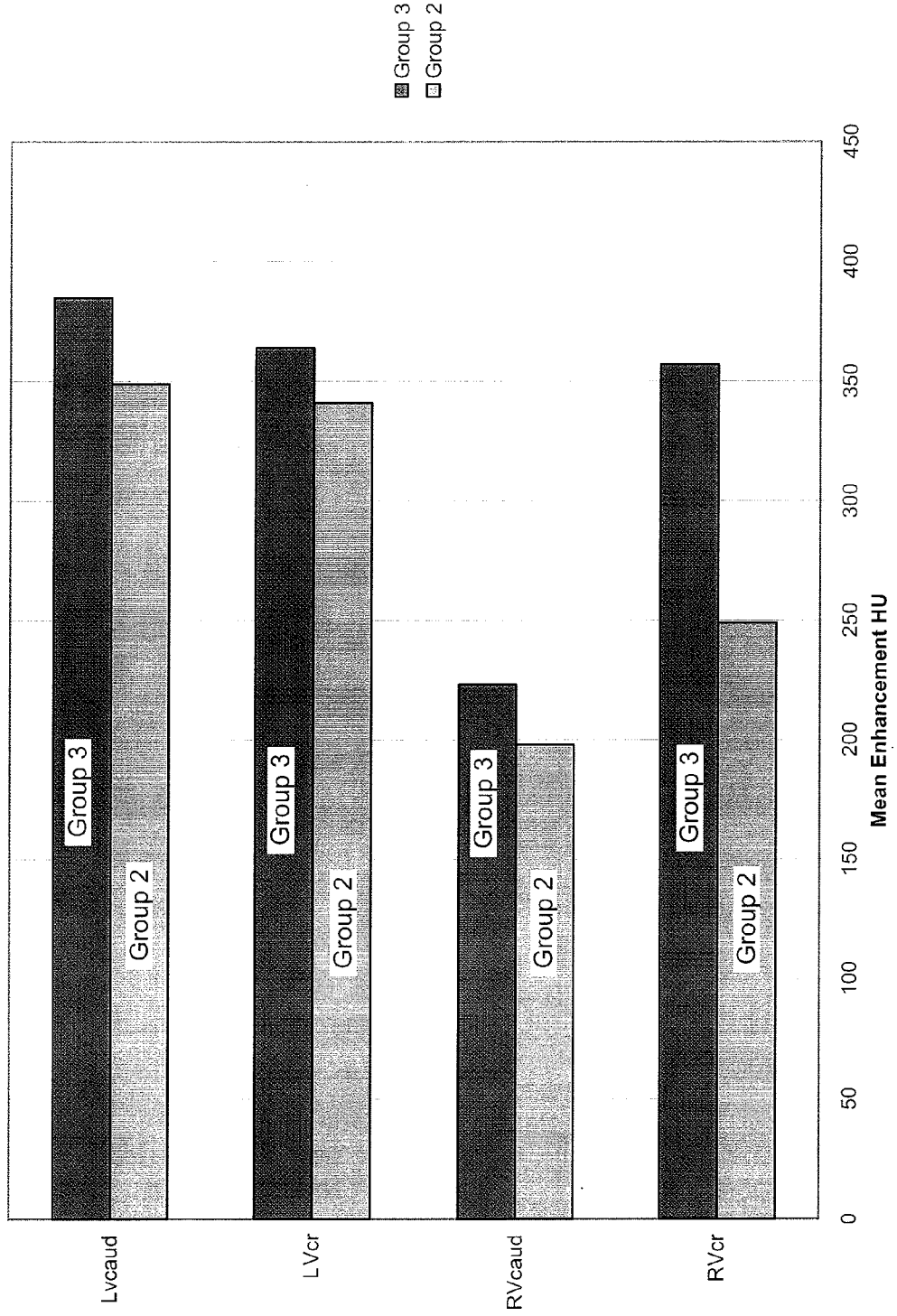
FIG. 45 illustrates mean attenuation achieved for various regions of interests (left and right ventricles) for each of a standard contrast medium delivery protocol in which 80 ml of contrast medium were injected with a flow-rate of 6.0 ml/s (Group 2) and a contrast medium delivery protocol generated using a parameter generation system of the present invention (Group 3).
Figure 46:
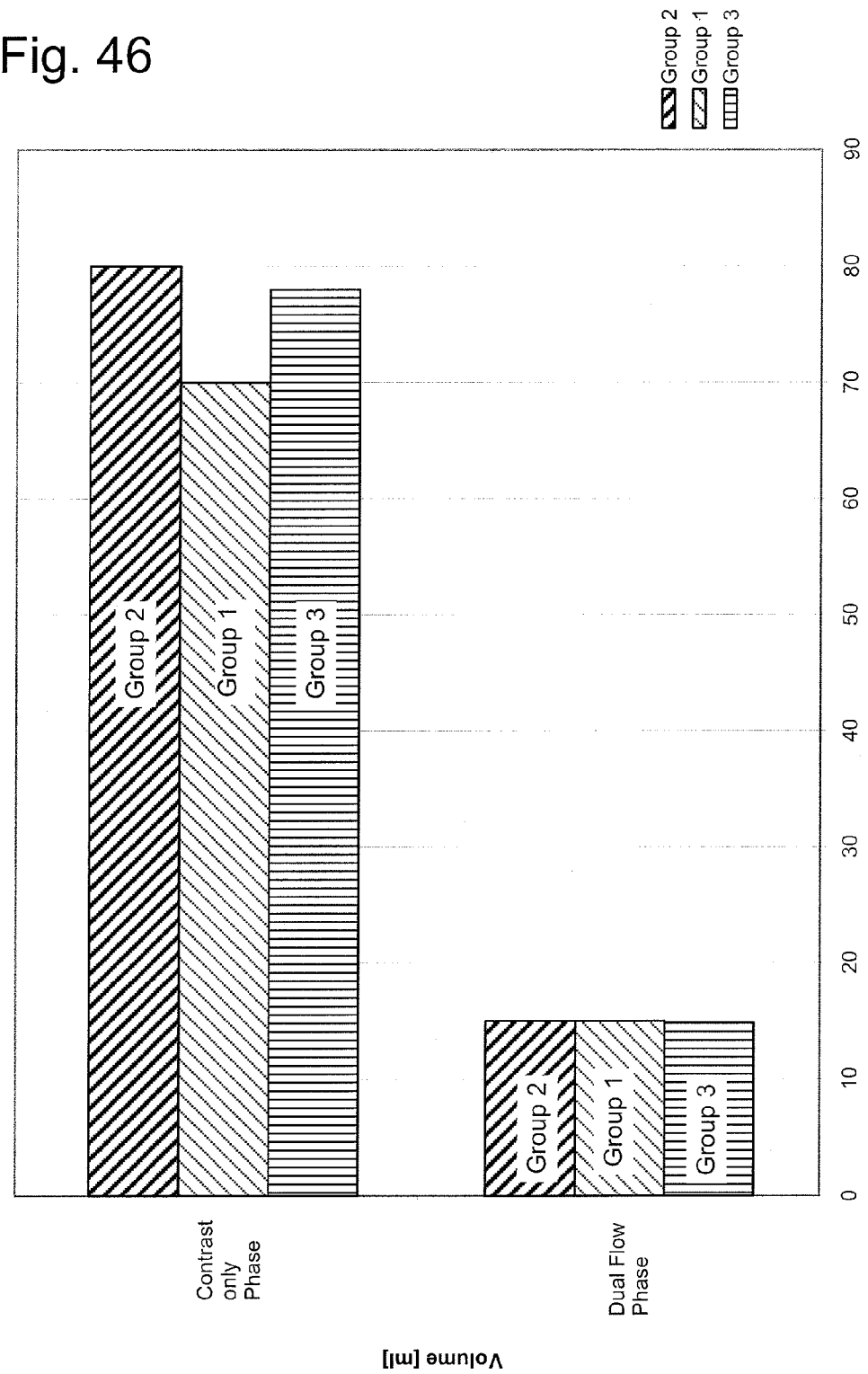
FIG. 46 illustrates a graphical representation of the volume of contrast medium injected in two phases of injection (a contrast medium only phase—volume A—and a dual flow phase—volume A/B) for each of Group 1, Group 2 and Group 3.

Data from the study are set forth in FIGS. 42 through 46. Mean scan times did not differ significantly. The mean contrast volume applied in group 3 was 77.8 ml in the contrast only phase. Enhancement in the coronary arteries is set forth for groups 1 and 3 in FIG. 42 and for groups 2 and 3 in FIG. 43. As illustrated in FIG. 42, enhancement in the RCA was significantly higher in all segments of the RCA in group 3 as compared to group 1 (412.1, 412.5 and 4220HU vs. 358.3, 345.4 and 321.8HU). As illustrated in FIG. 43, only the enhancement in the distal RCA differed significantly between group 3 and group 2. Enhancement in the left and right ventricles is set forth for groups 1 and 3 in FIG. 44 and for groups 2 and 3 in FIG. 45. In group 3 significantly higher enhancement was observed towards the end of the exam in the caudal left ventricle. Enhancement in the right ventricle did not differ significantly.

The study showed that the per-patient determined injection protocols of the present invention yielded higher enhancement, especially in the distal segments of the coronary vessels as compared to injection protocols using fixed injection parameters.

Figure 47:
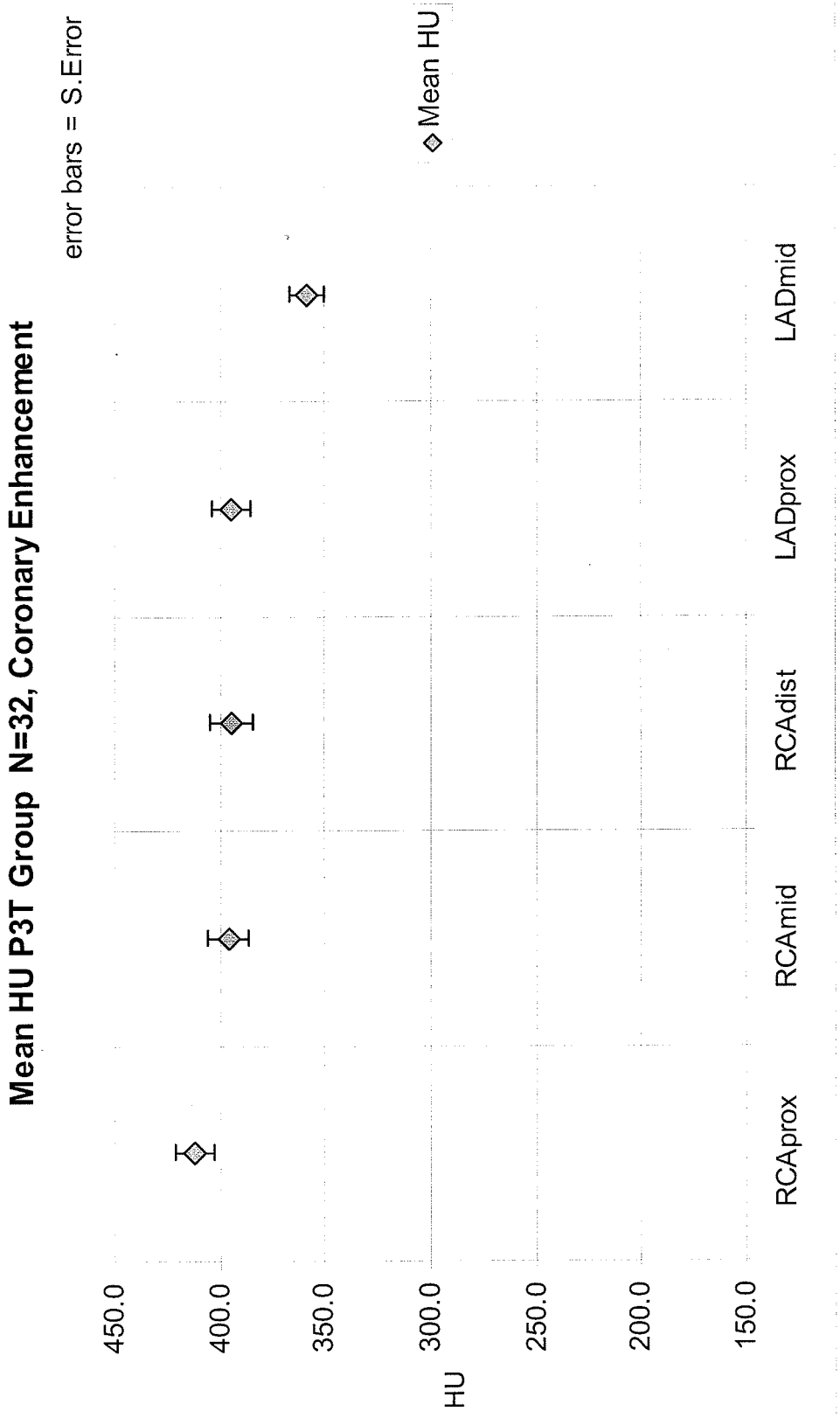
FIG. 47 illustrates mean contrast enhancement in five coronary segments across 32 subjects for another study of a parameter generation system of the present invention.
Figure 48:
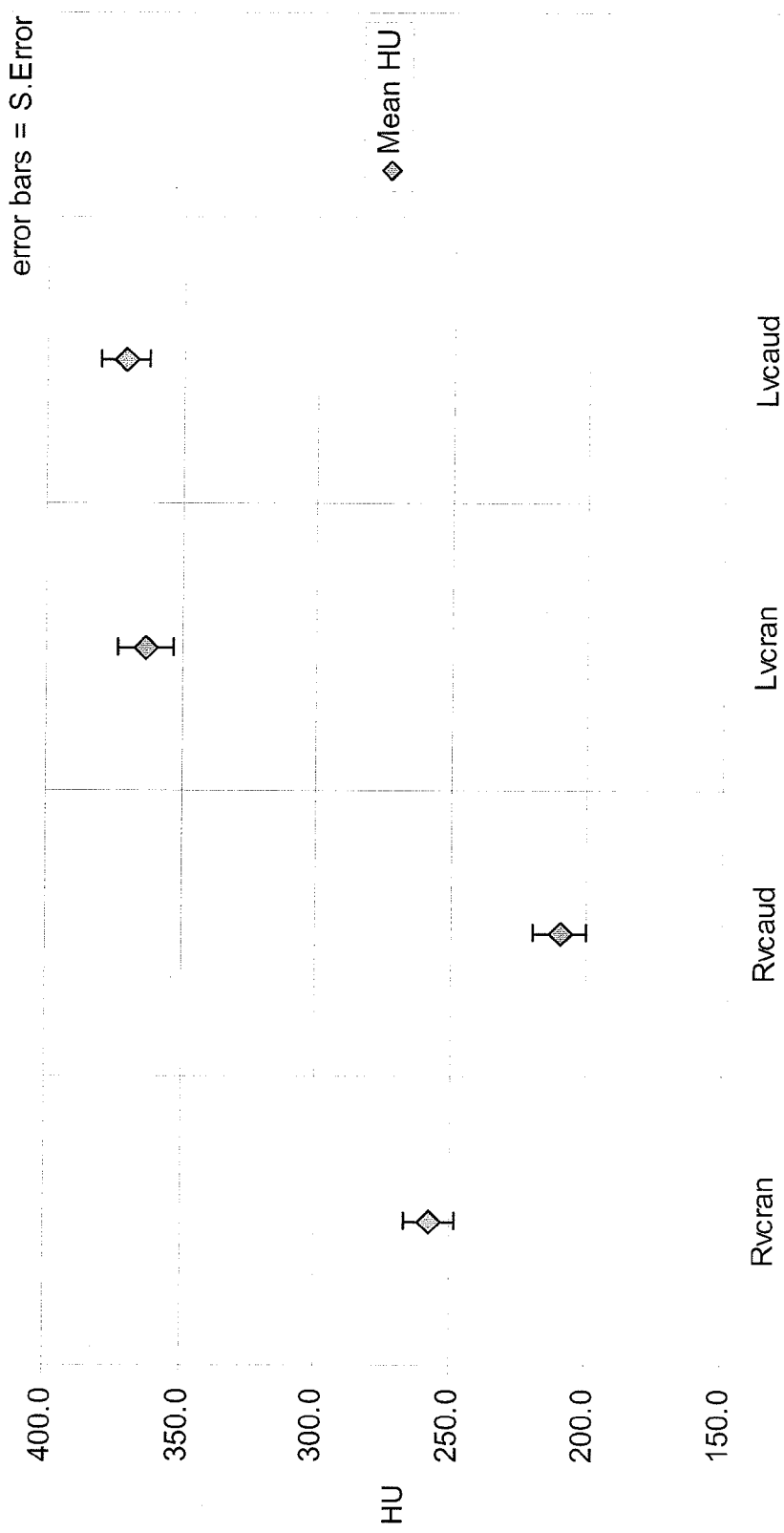
FIG. 48 illustrates mean contrast enhancement in four locations of the right and left ventricles.

FIG. 47 illustrates mean contrast enhancement in another study of five coronary segments across 32 subjects. The error bars in FIG. 47 represent the standard error of the mean. FIG. 47 illustrates achievement of various design goals of the parameter generation algorithm of the present invention used in the study. For example, a desirable level of contrast enhancement (for example, at least 350 HU) was achieved across the coronary anatomy. Further, the level of enhancement was generally consistent over the studied regions of the coronary anatomy and across subjects (as evidenced by the tight standard error of the mean). FIG. 48 illustrates mean contrast enhancement in four locations of the right and left ventricles. The measurements were made by manual placement of an ROI in a cranial (cran) and caudal (caud) section of the Right Ventricle (RV) and Left Ventricle (LV), respectively, in 32 subjects. The error bars of FIG. 48 represent plus and minus standard error of the mean. FIG. 48 illustrates the ability of the parameter generation systems of the present invention to provide desired, consistent enhancement in the Left Ventricle. Desired enhancement in the LV is typically greater than 300 HU for cardiac CTA. In CTA of the heart, one does not desire the right side of the heart to be enhanced as much as the left heart. However, some contrast enhancement is desired. In the studied embodiment, the parameter generation system achieved adequate right heart enhancement without causing streak artifacts or beam-hardening artifacts associated with some current cardiac CTA procedure. The right ventricular enhancement illustrated in FIG. 47 demonstrates adequate enhancement consistent across subjects (as evidenced by the tight standard error of the mean), and an enhancement level of at least 100 HU less than the left heart.

The representative embodiments set forth above are discussed primarily in the context of CT imaging. However, the devices, systems and methods of the present invention have wide applicability to the injection of pharmaceuticals. For example, the systems devices and methods of the present invention can be used in connection with the injection of contrast media for imaging procedures other than CT (for example, MRI, ultrasound, PET, etc.).

As briefly described above, the flow rate predicted for a phase (or time instance of an injection) can be used as an input to a system or model adapted or operable to predict the amount of pressure generated in the syringe or other container as a result of the volumetric flow rate, the fluid path characteristics (for example, the inner diameter of the catheter (gauge)), and the viscosity of the contrast agent. Generally, the viscosity of contrast medium increases geometrically with respect to the iodine concentration of the contrast medium in the case of a CT contrast. The viscosity can be calculated or retrieved from, for example, a data table. The pressure resulting from a set of values of these variables may be computed from fluid dynamics principles as known in the art or determined from prior experimental data. A discussion of pressure modeling is set forth in PCT International Patent Application No. PCT/US05/42891, which sets forth several embodiments of a model or system for predicting pressure at various points in an injection fluid path. If the predicted pressure exceeds a pressure limit or threshold set by the operator and/or a safe pressure limit determined by the manufacturer of the power injector, the operator can be warned of a possible over-pressure indication by, for example, a color coding of the flow rate entry field. Various other visual, audible and/or tactile indications of a predicted over-pressure situation can be provided.

In general, the embodiments of a parameter generation system described above determine the parameters of an initial protocol using information available prior to characterization of the cardiovascular system and propagation of a pharmaceutical therethrough. The initial protocol provides information on the volume of one or more fluids to be delivered to, for example, enable preloading of one or more syringes. Upon completion of characterization of the cardiovascular system, the parameters of the protocol are adjusted on the basis of the characterization. The parameter generation systems of the present invention were described in connection with an injection including an initial contrast only injection phase and a subsequent admixture phase. As clear to one skilled in the art, the parameter generation system of the present invention is applicable to the injection of various pharmaceuticals, with or without injection of diluent of flushing fluids, via injection protocols that can include one, two of more phases.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A system, comprising:
   a first pressurizing drive member adapted to be operably associated with at least a first fluid container, the first fluid container being adapted to contain a pharmaceutical comprising a contrast enhancing agent to be injected in an imaging procedure; and
   a controller operably associated with the first pressurizing drive member, the controller comprising a programming system to allow programming of an injection protocol via which injection of the pharmaceutical from the at least a first fluid container is controlled, the injection protocol comprising at least a first phase;
   a parameter generation system in communication with the controller and comprising a processor, a memory system and an input system, the processor executing an algorithm stored in the memory system, the algorithm determining parameters of the at least a first phase of the injection protocol based at least in part upon a type of the injection protocol identified via the input system, wherein the parameter generation system determines a volume of the pharmaceutical that is to be delivered to a patient at least partly on the basis of a concentration of the contrast enhancing agent in the pharmaceutical identified via the input system and at least partly on the basis of a function X having a value that differs depending upon a weight of the patient input via the input system.

2. The system of claim 1 wherein at least a first portion $V_1$ of the volume of the pharmaceutical to be delivered to the patient is calculated using the formula:

$$V_1 = \text{weight} * X * Y,$$

wherein Y is a function of the concentration of the contrast enhancing agent in the pharmaceutical.

3. The system of claim 2 wherein X is determined for the weight of a particular patient from an algorithm in which X is calculated as a function of weight.

4. The system of claim 2 wherein X is determined for the weight of a particular patient from a table wherein X is set forth as a function of weight.

5. The system of claim 2 further comprising:
   a second pressurizing drive member adapted to be operably associated with at least a second fluid container, the second fluid container adapted to contain a diluent fluid;
   wherein the controller is operably associated with the second pressurizing drive member, and wherein $V_1$ is the volume of the pharmaceutical to be delivered in a phase in which only the pharmaceutical is to be delivered to the patient, the parameter generation system also determining a volume $V_2$ of the pharmaceutical to be delivered in at least a second phase in which both the pharmaceutical and the diluent fluid are to be delivered to the patient.

6. The system of claim 5 wherein a flow rate of the pharmaceutical delivered in the first phase is approximately equal to a flow rate of an admixture of the pharmaceutical and the diluent fluid delivered in the second phase.

7. The system of claim 6 wherein the flow rate of the pharmaceutical is calculated by dividing $V_1$ by an injection duration of the first phase.

8. The system of claim 7 wherein the injection duration of the first phase is determined by adding a factor K to a scan duration of an imaging system.

9. The system of claim 8 wherein K ranges from 0 to 10 seconds.

10. The system of claim 9 wherein a minimum for the injection duration of the first phase can be input into the parameter generation system.

11. The system of claim 10 wherein the flow rate of the pharmaceutical delivered in the first phase is calculated by dividing $V_1$ by the injection duration of the first phase.

12. The system of claim 6 wherein the volume $V_2$ of the pharmaceutical to be delivered to the patient in the second phase is calculated based at least in part on a parameter of the patient selected from the group consisting of weight, body mass index, body surface area, and cardiac output.

13. The system of claim 12 wherein the parameter generation system determines whether a total volume of the pharmaceutical to be delivered to the patient in all phases exceeds an available volume of the pharmaceutical available for delivery to the patient, the parameter generation system further comprising rules to reduce the total volume of the pharmaceutical if the total volume exceeds the available volume.

14. The system of claim 5 wherein a total volume of the pharmaceutical to be delivered to the patient in all phases is determined.

15. The system of claim 14 wherein an initial protocol determined by the parameter generation system to determine the total volume of the pharmaceutical to be delivered to the patient is adjusted based upon a characterization of a cardiovascular system of the patient.

16. The system of claim 15 wherein a test bolus of the pharmaceutical is performed to characterize the cardiovascular system of the patient.

17. The system of claim 16 wherein the initial protocol is adjusted at least in part on the basis of a time to peak enhancement of the test bolus.

18. The system of claim 16 wherein the initial protocol is adjusted at least in part on the basis of a time to peak enhancement of the test bolus and a level of enhancement of the peak enhancement.

19. The system of claim 2 wherein X decreases nonlinearly with increasing weight of the patient.

* * * * *

UNITED STATES PATENT AND TRADEMARK OFFICE
CERTIFICATE OF CORRECTION

PATENT NO. : 9,302,044 B2  
APPLICATION NO. : 12/519213  
DATED : April 5, 2016  
INVENTOR(S) : Kalafut et al.

It is certified that error appears in the above-identified patent and that said Letters Patent is hereby corrected as shown below:

IN THE SPECIFICATION:

Column 18, Line 17, delete "$T_{scan\_end}$" and insert -- $t_{scan\_end}$ --, therefor.
Column 31, Line 26, delete "lopimidol" and insert -- (Iopamidol --, therefor.
Column 31, Line 28, delete "lopimidol" and insert -- (Iopamidol --, therefor.

Signed and Sealed this
Twenty-eighth Day of June, 2016

Michelle K. Lee
*Director of the United States Patent and Trademark Office*